(12) United States Patent
Saadat

(10) Patent No.: US 10,307,200 B2
(45) Date of Patent: Jun. 4, 2019

(54) APPARATUS AND METHODS FOR TREATING RHINITIS

(71) Applicant: Arrinex, Inc., Redwood City, CA (US)

(72) Inventor: Vahid Saadat, Atherton, CA (US)

(73) Assignee: Arrinex, Inc., Redwood City, CA (US)

(*) Notice: Subject to any disclaimer, the term of this patent is extended or adjusted under 35 U.S.C. 154(b) by 0 days.

(21) Appl. No.: 15/982,537

(22) Filed: May 17, 2018

(65) Prior Publication Data

US 2018/0263678 A1 Sep. 20, 2018

Related U.S. Application Data

(60) Continuation of application No. 15/693,216, filed on Aug. 31, 2017, now Pat. No. 10,028,781, which is a
(Continued)

(51) Int. Cl.
*A61B 18/14* (2006.01)
*A61B 18/02* (2006.01)
(Continued)

(52) U.S. Cl.
CPC ............. *A61B 18/02* (2013.01); *A61B 1/233* (2013.01); *A61B 17/24* (2013.01);
(Continued)

(58) Field of Classification Search
CPC ................ A61B 18/02; A61B 18/1485; A61B 2018/00327; A61B 2018/00434;
(Continued)

(56) References Cited

U.S. PATENT DOCUMENTS 4,887,605 A 12/1989 Angelsen et al.
5,348,008 A 9/1994 Bornn et al.
(Continued)

FOREIGN PATENT DOCUMENTS

EP 2532300 12/2012
EP 2662027 11/2013
(Continued)

OTHER PUBLICATIONS

Anggard, "The Effects of Parasympathetic Nerve Stimulation on the Microcirculation and Secretion in the Nasal Musosa of the Cat", Acta Oto-Laryngologica, vol. 78, Issue 1-6, Jul. 8, 2009, pp. 98-105.
(Continued)

*Primary Examiner* — Michael F Peffley
*Assistant Examiner* — Samantha M Good
(74) *Attorney, Agent, or Firm* — McDonnell Boehnen Hulbert & Berghoff LLP

(57) ABSTRACT

Apparatus and methods for treating conditions such as rhinitis are disclosed herein where a distal end of a probe shaft is introduced through the nasal cavity where the distal end has an end effector with a first configuration having a low-profile which is shaped to manipulate tissue within the nasal cavity. The distal end may be positioned into proximity of a tissue region having a post nasal nerve associated with a middle or inferior nasal turbinate. Once suitably positioned, the distal end may be reconfigured from the first configuration to a second configuration which is shaped to contact and follow the tissue region and the post nasal nerve may then be ablated via the distal end. Ablation may be performed using various mechanisms, such as cryotherapy, and optionally under direct visualization.

27 Claims, 45 Drawing Sheets

Related U.S. Application Data division of application No. 15/242,362, filed on Aug. 19, 2016, now Pat. No. 9,763,723, which is a continuation of application No. 14/503,060, filed on Sep. 30, 2014, now Pat. No. 9,687,288.

(60) Provisional application No. 62/015,468, filed on Jun. 22, 2014, provisional application No. 61/884,547, filed on Sep. 30, 2013.

(51) Int. Cl.
  A61B 1/233 (2006.01)
  A61B 17/24 (2006.01)
  A61N 7/02 (2006.01)
  A61B 18/00 (2006.01)
  A61B 90/00 (2016.01)
  A61N 7/00 (2006.01)

(52) U.S. Cl.
  CPC ............ *A61B 18/1485* (2013.01); *A61N 7/02* (2013.01); *A61N 7/022* (2013.01); *A61B 2018/0022* (2013.01); *A61B 2018/00327* (2013.01); *A61B 2018/00434* (2013.01); *A61B 2018/00577* (2013.01); *A61B 2018/00714* (2013.01); *A61B 2018/00791* (2013.01); *A61B 2018/00982* (2013.01); *A61B 2018/0212* (2013.01); *A61B 2018/0268* (2013.01); *A61B 2018/143* (2013.01); *A61B 2018/1475* (2013.01); *A61B 2090/378* (2016.02); *A61B 2218/002* (2013.01); *A61N 2007/003* (2013.01)

(58) Field of Classification Search
  CPC . A61B 2018/00577; A61B 17/24; A61B 1/01; A61B 1/233; A61N 7/02; A61N 7/022
  See application file for complete search history.

(56) References Cited

U.S. PATENT DOCUMENTS

| | | | |
|---|---|---|---|
| 5,527,351 | A | 6/1996 | Friedman |
| 5,533,499 | A | 7/1996 | Johnson |
| 5,542,916 | A | 8/1996 | Hirsch et al. |
| 5,611,796 | A | 3/1997 | Kamami |
| 5,624,439 | A | 4/1997 | Edwards et al. |
| 5,674,191 | A | 10/1997 | Edwards et al. |
| 5,707,349 | A | 1/1998 | Edwards |
| 5,718,702 | A | 2/1998 | Edwards |
| 5,728,094 | A | 3/1998 | Edwards |
| 5,730,719 | A | 3/1998 | Edwards |
| 5,733,280 | A | 3/1998 | Avitall |
| 5,738,114 | A | 4/1998 | Edwards |
| 5,743,870 | A | 4/1998 | Edwards |
| 5,743,904 | A | 4/1998 | Edwards |
| 5,746,224 | A | 5/1998 | Edwards |
| 5,800,429 | A | 9/1998 | Edwards |
| 5,807,306 | A | 9/1998 | Shapland et al. |
| 5,816,095 | A | 10/1998 | Nordell et al. |
| 5,817,049 | A | 10/1998 | Edwards |
| 5,820,580 | A | 10/1998 | Edwards et al. |
| 5,823,197 | A | 10/1998 | Edwards |
| 5,827,277 | A | 10/1998 | Edwards |
| 5,843,021 | A | 12/1998 | Edwards et al. |
| 5,843,077 | A | 12/1998 | Edwards |
| 5,846,235 | A | 12/1998 | Pasricha et al. |
| 5,879,349 | A | 3/1999 | Edwards |
| 5,899,898 | A | 5/1999 | Arless et al. |
| 5,899,899 | A | 5/1999 | Arless et al. |
| 5,938,659 | A | 8/1999 | Tu et al. |
| 5,971,979 | A | 10/1999 | Joye et al. |
| 6,045,549 | A | 4/2000 | Smethers et al. |
| 6,063,079 | A | 5/2000 | Hovda et al. |
| 6,096,033 | A | 8/2000 | Tu et al. |
| 6,102,907 | A | 8/2000 | Smethers et al. |
| 6,106,518 | A | 8/2000 | Wittenberger et al. |
| 6,109,268 | A | 8/2000 | Thapliyal et al. |
| 6,126,657 | A | 10/2000 | Edwards et al. |
| 6,131,579 | A | 10/2000 | Thorson et al. |
| 6,139,546 | A | 10/2000 | Koenig et al. |
| 6,152,143 | A | 11/2000 | Edwards |
| 6,165,173 | A | 12/2000 | Kamdar et al. |
| 6,179,803 | B1 | 1/2001 | Edwards et al. |
| 6,210,355 | B1 | 4/2001 | Edwards et al. |
| 6,228,079 | B1 | 5/2001 | Koenig |
| 6,231,569 | B1 | 5/2001 | Bek et al. |
| 6,270,476 | B1 | 8/2001 | Santoianni et al. |
| 6,283,959 | B1 | 9/2001 | Lalonde et al. |
| 6,293,941 | B1 | 9/2001 | Strul et al. |
| 6,309,386 | B1 | 10/2001 | Bek |
| 6,355,029 | B1 | 3/2002 | Joye et al. |
| 6,371,926 | B1 | 4/2002 | Thorson et al. |
| 6,375,654 | B1 | 4/2002 | McIntyre |
| 6,383,181 | B1 | 5/2002 | Johnston et al. |
| 6,391,028 | B1 | 5/2002 | Fanton et al. |
| 6,416,491 | B1 | 7/2002 | Edwards et al. |
| 6,425,151 | B2 | 7/2002 | Barnett |
| 6,428,534 | B1 | 8/2002 | Joye et al. |
| 6,431,174 | B1 | 8/2002 | Knudson et al. |
| 6,432,102 | B2 | 8/2002 | Joye et al. |
| 6,451,013 | B1 | 9/2002 | Bays et al. |
| 6,502,574 | B2 | 1/2003 | Stevens et al. |
| 6,514,245 | B1 | 2/2003 | Williams et al. |
| 6,517,533 | B1 | 2/2003 | Swaminathan |
| 6,517,535 | B2 | 2/2003 | Edwards |
| 6,537,271 | B1 | 3/2003 | Murray et al. |
| 6,551,310 | B1 | 4/2003 | Ganz et al. |
| 6,562,036 | B1 | 5/2003 | Ellman et al. |
| 6,575,966 | B2 | 6/2003 | Lane et al. |
| 6,575,969 | B1 | 6/2003 | Rittman et al. |
| 6,589,235 | B2 | 7/2003 | Wong et al. |
| 6,595,988 | B2 | 7/2003 | Wittenberger et al. |
| 6,602,276 | B2 | 8/2003 | Dobak, III et al. |
| 6,648,879 | B2 | 11/2003 | Joye et al. |
| 6,659,106 | B1 | 12/2003 | Hovda et al. |
| 6,666,858 | B2 | 12/2003 | Lafontaine |
| 6,673,066 | B2 | 1/2004 | Werneth |
| 6,685,732 | B2 | 2/2004 | Kramer |
| 6,736,809 | B2 | 5/2004 | Capuano et al. |
| 6,786,900 | B2 | 9/2004 | Joye et al. |
| 6,786,901 | B2 | 9/2004 | Joye et al. |
| 6,811,550 | B2 | 11/2004 | Holland et al. |
| 6,875,209 | B2 | 4/2005 | Zvuloni et al. |
| 6,905,494 | B2 | 6/2005 | Yon et al. |
| 6,908,462 | B2 | 6/2005 | Joye et al. |
| 6,911,027 | B1 | 6/2005 | Edwards et al. |
| 6,949,096 | B2 | 9/2005 | Davison et al. |
| 6,972,015 | B2 | 12/2005 | Joye et al. |
| 6,978,781 | B1 | 12/2005 | Jordan |
| 6,989,009 | B2 | 1/2006 | Lafontaine |
| 6,991,631 | B2 | 1/2006 | Woloszko et al. |
| 7,001,378 | B2 | 2/2006 | Yon et al. |
| 7,055,523 | B1 | 6/2006 | Brown |
| 7,060,062 | B2 | 6/2006 | Joye et al. |
| 7,081,112 | B2 | 7/2006 | Joye et al. |
| 7,101,368 | B2 | 9/2006 | Lafontaine |
| 7,104,984 | B2 | 9/2006 | Ryba |
| 7,114,495 | B2 | 10/2006 | Lockwood, Jr. |
| 7,189,227 | B2 | 3/2007 | Lafontaine |
| 7,288,089 | B2 | 10/2007 | Yon et al. |
| 7,291,144 | B2 | 11/2007 | Dobak, III et al. |
| 7,300,433 | B2 | 11/2007 | Lane et al. |
| 7,322,993 | B2 | 1/2008 | Metzger et al. |
| 7,354,434 | B2 | 4/2008 | Zvuloni et al. |
| 7,416,550 | B2 | 8/2008 | Protsenko et al. |
| 7,418,292 | B2 | 8/2008 | Shafer |
| 7,442,190 | B2 | 10/2008 | Abboud et al. |
| 7,442,191 | B2 | 10/2008 | Hovda et al. |
| 7,449,018 | B2 | 11/2008 | Kramer |
| 7,527,622 | B2 | 5/2009 | Lane et al. |
| 7,641,679 | B2 | 1/2010 | Joye et al. |
| 7,648,497 | B2 | 1/2010 | Lane et al. |
| 7,678,069 | B1 | 3/2010 | Baker et al. |
| 7,727,191 | B2 | 6/2010 | Mihalik et al. |

(56) References Cited

U.S. PATENT DOCUMENTS

| | | |
|---|---|---|
| 7,727,228 B2 | 6/2010 | Abboud et al. |
| 7,740,627 B2 | 6/2010 | Gammie et al. |
| 7,769,442 B2 | 8/2010 | Shafer |
| 7,780,730 B2 | 8/2010 | Saidi |
| 7,794,455 B2 | 9/2010 | Abboud et al. |
| 7,824,394 B2 | 11/2010 | Manstein |
| 7,842,031 B2 | 11/2010 | Abboud et al. |
| 7,850,683 B2 | 12/2010 | Elkins et al. |
| 7,862,557 B2 | 1/2011 | Joye et al. |
| 7,892,230 B2 | 2/2011 | Woloszko |
| 8,043,283 B2 | 10/2011 | Dobak, III et al. |
| 8,043,351 B2 | 10/2011 | Yon et al. |
| 8,088,127 B2 | 1/2012 | Mayse et al. |
| 8,137,345 B2 | 3/2012 | Mcnall et al. |
| 8,142,424 B2 | 3/2012 | Swanson |
| 8,157,794 B2 | 4/2012 | Dobak, III et al. |
| 8,177,779 B2 | 5/2012 | Joye et al. |
| 8,187,261 B2 | 5/2012 | Watson |
| 8,231,613 B2 | 7/2012 | Baxter et al. |
| 8,235,976 B2 | 8/2012 | Lafontaine |
| 8,292,887 B2 | 10/2012 | Woloszko et al. |
| 8,298,217 B2 | 10/2012 | Lane et al. |
| 8,317,781 B2 | 11/2012 | Owens et al. |
| 8,317,782 B1 | 11/2012 | Ellman et al. |
| 8,333,758 B2 | 12/2012 | Joye et al. |
| 8,382,746 B2 | 2/2013 | Williams et al. |
| 8,382,747 B2 | 2/2013 | Abboud et al. |
| 8,388,600 B1 | 3/2013 | Eldredge |
| 8,394,075 B2 | 3/2013 | Ansarinia |
| 8,425,456 B2 | 4/2013 | Mihalik et al. |
| 8,425,457 B2 | 4/2013 | John et al. |
| 8,439,906 B2 | 5/2013 | Watson |
| 8,465,481 B2 | 6/2013 | Mazzone et al. |
| 8,475,440 B2 | 7/2013 | Abboud et al. |
| 8,480,664 B2 | 7/2013 | Watson et al. |
| 8,491,636 B2 | 7/2013 | Abboud et al. |
| 8,512,324 B2 | 8/2013 | Abboud et al. |
| 8,545,491 B2 | 10/2013 | Abboud et al. |
| 8,591,504 B2 | 11/2013 | Tin |
| 8,617,149 B2 | 12/2013 | Lafontaine et al. |
| 8,632,529 B2 | 1/2014 | Bencini |
| 8,663,211 B2 | 3/2014 | Fourkas et al. |
| 8,672,930 B2 | 3/2014 | Wittenberger |
| 8,676,324 B2 | 3/2014 | Simon et al. |
| 8,679,104 B2 | 3/2014 | Abboud et al. |
| 8,679,105 B2 | 3/2014 | Wittenberger et al. |
| 8,715,274 B2 | 5/2014 | Watson |
| 8,715,275 B2 | 5/2014 | Burger et al. |
| 8,747,401 B2 | 6/2014 | Gonzalez et al. |
| 8,764,740 B2 | 7/2014 | Watson |
| 8,771,264 B2 | 7/2014 | Abboud et al. |
| 8,827,952 B2 | 9/2014 | Subramaniam et al. |
| 8,900,222 B2 | 12/2014 | Abboud et al. |
| 8,911,434 B2 | 12/2014 | Wittenberger |
| 8,926,602 B2 | 1/2015 | Pageard |
| 8,936,594 B2 | 1/2015 | Wolf et al. |
| 8,945,107 B2 | 2/2015 | Buckley et al. |
| 8,986,293 B2 | 3/2015 | Desrochers |
| 8,986,301 B2 | 3/2015 | Wolf et al. |
| 8,996,137 B2 | 3/2015 | Ackermann et al. |
| 9,050,073 B2 | 6/2015 | Newell et al. |
| 9,050,074 B2 | 6/2015 | Joye et al. |
| 9,060,754 B2 | 6/2015 | Buckley et al. |
| 9,060,755 B2 | 6/2015 | Buckley et al. |
| 9,066,713 B2 | 6/2015 | Turovskiy |
| 9,072,597 B2 | 7/2015 | Wolf et al. |
| 9,084,590 B2 | 7/2015 | Wittenberger et al. |
| 9,084,592 B2 | 7/2015 | Wu et al. |
| 9,089,314 B2 | 7/2015 | Wittenberger |
| 9,101,346 B2 | 8/2015 | Burger et al. |
| 9,125,677 B2 | 9/2015 | Sobol et al. |
| 9,168,079 B2 | 10/2015 | Lalonde |
| 9,168,081 B2 | 10/2015 | Williams et al. |
| 9,179,964 B2 | 11/2015 | Wolf et al. |
| 9,179,967 B2 | 11/2015 | Wolf et al. |
| 9,211,393 B2 | 12/2015 | Hu et al. |
| 9,220,556 B2 | 12/2015 | Lalonde et al. |
| 9,237,924 B2 | 1/2016 | Wolf et al. |
| 9,241,752 B2 | 1/2016 | Nash et al. |
| 9,254,166 B2 | 2/2016 | Aluru et al. |
| 9,265,956 B2 | 2/2016 | Ackermann et al. |
| 9,333,023 B2 | 5/2016 | Wittenberger |
| 9,414,878 B1 | 8/2016 | Wu et al. |
| 9,415,194 B2 | 8/2016 | Wolf et al. |
| 9,433,463 B2 | 9/2016 | Wolf et al. |
| 9,439,709 B2 | 9/2016 | Duong et al. |
| 9,445,859 B2 | 9/2016 | Pageard |
| 9,452,010 B2 | 9/2016 | Wolf et al. |
| 9,452,087 B2 | 9/2016 | Holm et al. |
| 9,480,521 B2 | 11/2016 | Kim et al. |
| 9,486,278 B2 | 11/2016 | Wolf et al. |
| 9,522,030 B2 | 12/2016 | Harmouche et al. |
| 9,526,571 B2 | 12/2016 | Wolf et al. |
| 9,555,223 B2 | 1/2017 | Abboud et al. |
| 9,572,536 B2 | 2/2017 | Abboud et al. |
| 9,687,288 B2 | 6/2017 | Saadat |
| 9,687,296 B2 | 6/2017 | Wolf et al. |
| 9,763,723 B2 | 9/2017 | Saadat |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 2002/0016588 A1 | 2/2002 | Wong et al. |
| 2002/0049464 A1 | 4/2002 | Donofrio et al. |
| 2002/0128641 A1 | 9/2002 | Underwood et al. |
| 2003/0144659 A1 | 7/2003 | Edwards |
| 2003/0208194 A1 | 11/2003 | Hovda et al. |
| 2003/0225403 A1 | 12/2003 | Woloszko et al. |
| 2004/0024412 A1 | 2/2004 | Clements et al. |
| 2004/0054366 A1 | 3/2004 | Davison et al. |
| 2004/0186535 A1 | 9/2004 | Knowlton |
| 2004/0220644 A1 | 11/2004 | Shalev et al. |
| 2005/0020901 A1 | 1/2005 | Belson et al. |
| 2005/0119643 A1 | 6/2005 | Sobol et al. |
| 2005/0222565 A1 | 10/2005 | Manstein |
| 2005/0234439 A1 | 10/2005 | Underwood |
| 2006/0235377 A1 | 10/2006 | Earley et al. |
| 2006/0235474 A1 | 10/2006 | Demarais |
| 2006/0253117 A1 | 11/2006 | Hovda et al. |
| 2006/0276817 A1 | 12/2006 | Vassallo et al. |
| 2006/0276852 A1 | 12/2006 | Demarais et al. |
| 2007/0066944 A1 | 3/2007 | Nyte |
| 2007/0073282 A1 | 3/2007 | Mcgaffigan et al. |
| 2007/0173899 A1 | 7/2007 | Levin et al. |
| 2007/0219600 A1 | 9/2007 | Gertner et al. |
| 2007/0265687 A1 | 11/2007 | Deem et al. |
| 2007/0299433 A1 | 12/2007 | Williams et al. |
| 2008/0009851 A1 | 1/2008 | Wittenberger et al. |
| 2008/0009925 A1 | 1/2008 | Abboud et al. |
| 2008/0027423 A1 | 1/2008 | Choi et al. |
| 2008/0027480 A1 | 1/2008 | van der Burg et al. |
| 2008/0082090 A1 | 4/2008 | Manstein |
| 2008/0119693 A1 | 5/2008 | Makower et al. |
| 2008/0312644 A1 | 12/2008 | Fourkas et al. |
| 2009/0018485 A1 | 1/2009 | Krespi et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0143821 A1 | 6/2009 | Stupak |
| 2009/0182318 A1 | 7/2009 | Abboud et al. |
| 2009/0234345 A1 | 9/2009 | Hon |
| 2009/0292358 A1 | 11/2009 | Saidi |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0144996 A1 | 6/2010 | Kennedy et al. |
| 2010/0152730 A1 | 6/2010 | Makower et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0174283 A1 | 7/2010 | Mcnall et al. |
| 2010/0191112 A1 | 7/2010 | Demarais et al. |

(56) References Cited

U.S. PATENT DOCUMENTS

| | | | |
|---|---|---|---|
| 2010/0241114 A1* | 9/2010 | Privitera | A61B 18/02 606/21 |
| 2011/0009737 A1 | 1/2011 | Manstein | |
| 2011/0152855 A1 | 6/2011 | Mayse et al. | |
| 2011/0184402 A1 | 7/2011 | Baust et al. | |
| 2011/0282268 A1 | 11/2011 | Baker et al. | |
| 2012/0029493 A1 | 2/2012 | Wittenberger et al. | |
| 2012/0039954 A1 | 2/2012 | Cupit et al. | |
| 2012/0078377 A1 | 3/2012 | Gonzales et al. | |
| 2012/0143130 A1 | 6/2012 | Subramaniam et al. | |
| 2012/0197245 A1 | 8/2012 | Burnett et al. | |
| 2012/0298105 A1 | 11/2012 | Osorio | |
| 2012/0316473 A1 | 12/2012 | Bonutti et al. | |
| 2012/0316557 A1 | 12/2012 | Sartor et al. | |
| 2012/0323227 A1 | 12/2012 | Wolf et al. | |
| 2012/0323232 A1 | 12/2012 | Wolf et al. | |
| 2013/0006326 A1 | 1/2013 | Ackermann et al. | |
| 2013/0018366 A1 | 1/2013 | Wu et al. | |
| 2013/0218151 A1 | 8/2013 | Mihalik et al. | |
| 2013/0218158 A1 | 8/2013 | Danek et al. | |
| 2013/0253387 A1 | 9/2013 | Bonutti et al. | |
| 2013/0310822 A1 | 11/2013 | Mayse et al. | |
| 2013/0324989 A1 | 12/2013 | Leung et al. | |
| 2013/0345700 A1 | 12/2013 | Hlavka et al. | |
| 2014/0058369 A1 | 2/2014 | Hon | |
| 2014/0088463 A1 | 3/2014 | Wolf et al. | |
| 2014/0114233 A1 | 4/2014 | Deem et al. | |
| 2014/0186341 A1 | 7/2014 | Mayse | |
| 2014/0207130 A1 | 7/2014 | Fourkas et al. | |
| 2014/0236148 A1 | 8/2014 | Hlavka et al. | |
| 2014/0257271 A1 | 9/2014 | Mayse et al. | |
| 2014/0276792 A1 | 9/2014 | Kaveckis et al. | |
| 2014/0277429 A1 | 9/2014 | Kuzma et al. | |
| 2014/0316310 A1 | 10/2014 | Ackermann et al. | |
| 2014/0316396 A1 | 10/2014 | Wolf et al. | |
| 2014/0371812 A1 | 12/2014 | Ackermann et al. | |
| 2015/0011843 A1 | 1/2015 | Toth et al. | |
| 2015/0031946 A1 | 1/2015 | Saadat et al. | |
| 2015/0045781 A1 | 2/2015 | Abboud et al. | |
| 2015/0073395 A1 | 3/2015 | Wolf et al. | |
| 2015/0080870 A1 | 3/2015 | Wittenberger | |
| 2015/0119868 A1 | 4/2015 | Lalonde et al. | |
| 2015/0126986 A1 | 5/2015 | Kelly et al. | |
| 2015/0157382 A1 | 6/2015 | Avitall et al. | |
| 2015/0157395 A1 | 6/2015 | Wolf et al. | |
| 2015/0164401 A1 | 6/2015 | Toth et al. | |
| 2015/0164571 A1 | 6/2015 | Saadat | |
| 2015/0190188 A1 | 7/2015 | Lalonde | |
| 2015/0196345 A1 | 7/2015 | Newell et al. | |
| 2015/0196740 A1 | 7/2015 | Mallin et al. | |
| 2015/0202003 A1 | 7/2015 | Wolf et al. | |
| 2015/0223860 A1 | 8/2015 | Wittenberger et al. | |
| 2015/0238754 A1 | 8/2015 | Loudin et al. | |
| 2015/0250524 A1 | 9/2015 | Moriarty et al. | |
| 2015/0265329 A1 | 9/2015 | Lalonde et al. | |
| 2015/0265812 A1 | 9/2015 | Lalonde | |
| 2015/0272663 A1 | 10/2015 | Wolf et al. | |
| 2015/0297285 A1 | 10/2015 | Wolf et al. | |
| 2015/0313661 A1 | 11/2015 | Wu et al. | |
| 2016/0015450 A1 | 1/2016 | Wolf et al. | |
| 2016/0022992 A1 | 1/2016 | Franke et al. | |
| 2016/0038212 A1 | 2/2016 | Ryba et al. | |
| 2016/0045277 A1 | 2/2016 | Lin et al. | |
| 2016/0066975 A1 | 3/2016 | Fourkas et al. | |
| 2016/0074090 A1 | 3/2016 | Lalonde et al. | |
| 2016/0089200 A1 | 3/2016 | Wolf et al. | |
| 2016/0114163 A1 | 4/2016 | Franke et al. | |
| 2016/0114172 A1 | 4/2016 | Loudin et al. | |
| 2016/0012118 A1 | 5/2016 | Sirer et al. | |
| 2016/0143683 A1 | 5/2016 | Aluru et al. | |
| 2016/0158548 A1 | 6/2016 | Ackermann et al. | |
| 2016/0166305 A1 | 6/2016 | Nash et al. | |
| 2016/0166306 A1 | 6/2016 | Pageard | |
| 2016/0220295 A1 | 8/2016 | Wittenberger | |
| 2016/0287315 A1 | 10/2016 | Wolf et al. | |
| 2016/0317794 A1 | 11/2016 | Saadat | |
| 2016/0331433 A1 | 11/2016 | Wu et al. | |
| 2016/0331459 A1 | 11/2016 | Townley et al. | |
| 2016/0354134 A1 | 12/2016 | Pageard | |
| 2016/0354135 A1 | 12/2016 | Saadat | |
| 2016/0354136 A1 | 12/2016 | Saadat | |
| 2016/0361112 A1 | 12/2016 | Wolf et al. | |
| 2017/0007316 A1 | 1/2017 | Wolf et al. | |
| 2017/0014258 A1 | 1/2017 | Wolf et al. | |
| 2017/0042601 A1 | 2/2017 | Kim et al. | |
| 2017/0056087 A1 | 3/2017 | Buckley et al. | |
| 2017/0056632 A1 | 3/2017 | Jenkins et al. | |
| 2017/0095288 A1 | 4/2017 | Wolf et al. | |
| 2017/0209199 A1 | 7/2017 | Wolf et al. | |
| 2017/0231651 A1 | 8/2017 | Dinger et al. | |
| 2017/0245924 A1 | 8/2017 | Wolf et al. | |
| 2017/0252089 A1 | 9/2017 | Hester et al. | |
| 2017/0252100 A1 | 9/2017 | Wolf et al. | |
| 2017/0360494 A1 | 12/2017 | Saadat | |
| 2017/0360495 A1 | 12/2017 | Wolf et al. | |
| 2018/0000535 A1 | 1/2018 | Wolf et al. | |
| 2018/0133460 A1 | 5/2018 | Townley et al. | |
| 2018/0177542 A1 | 6/2018 | Wolf et al. | |
| 2018/0177546 A1 | 6/2018 | Dinger et al. | |
| 2018/0185085 A1 | 7/2018 | Wolf et al. | |
| 2018/0228533 A1 | 8/2018 | Wolf et al. | |
| 2018/0317993 A1 | 11/2018 | Saadat | |
| 2018/0344378 A1 | 12/2018 | Wolf et al. | |

FOREIGN PATENT DOCUMENTS

| | | |
|---|---|---|
| EP | 2662046 | 11/2013 |
| EP | 2662116 | 11/2013 |
| WO | 99020185 | 4/1999 |
| WO | 9927862 | 6/1999 |
| WO | 9930655 | 6/1999 |
| WO | 00009053 | 2/2000 |
| WO | 0047118 | 8/2000 |
| WO | 0054684 | 9/2000 |
| WO | 0143653 | 6/2001 |
| WO | 0164145 | 9/2001 |
| WO | 01095819 | 12/2001 |
| WO | 0204042 | 1/2002 |
| WO | 0207628 | 4/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2004108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |
| WO | 2007037895 | 4/2007 |
| WO | 2007134005 | 11/2007 |
| WO | 2007145759 | 12/2007 |
| WO | 2008000065 | 1/2008 |
| WO | 2008042890 | 4/2008 |
| WO | 2008046183 | 4/2008 |
| WO | 2008051918 | 5/2008 |
| WO | 2008157042 | 12/2008 |
| WO | 2009114701 | 9/2009 |
| WO | 2009146372 | 12/2009 |
| WO | 2010077980 | 7/2010 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |

(56) References Cited

FOREIGN PATENT DOCUMENTS

| WO | 2012012868 | 2/2012 |
|---|---|---|
| WO | 2012012869 | 2/2012 |
| WO | 2012015636 | 2/2012 |
| WO | 2012019156 | 2/2012 |
| WO | 2012051697 | 4/2012 |
| WO | 2012027641 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 02069862 | 9/2012 |
| WO | 2012174161 | 12/2012 |
| WO | 2013035192 | 3/2013 |
| WO | 2013110156 | 8/2013 |
| WO | 2013173481 | 11/2013 |
| WO | 2013163325 | 2/2014 |
| WO | 2014113864 | 7/2014 |
| WO | 2014138866 | 9/2014 |
| WO | 2014138867 | 9/2014 |
| WO | 2015038523 | 3/2015 |
| WO | 2015047863 | 4/2015 |
| WO | 2015048806 | 4/2015 |
| WO | 2015061883 | 5/2015 |
| WO | 2015081420 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |

OTHER PUBLICATIONS

Arora et al., "Cryodestruction of Vidian Nerve Branches", Indian Journal of Otolaryngology, vol. 32, No. 3, Sep. 1980, pp. 80-82.
Bicknell, "CryoSurrgery for Allergic and Vasomotor Rhinitis", The Journal of Laryngology and Otology, vol. 93, Feb. 1979, pp. 143-146.
Bluestone et al., "Intranasal Freezing for Severe Epistaxis", Arch Otolaryng, vol. 85, Apr. 1967, pp. 119-121.
Buckley et al., "High-Resolution Spatial Mapping of Shear Properties in Cartilage", J Biomech, vol. 43, No. 4, Nov. 5, 2009, pp. 796-800.
Buckley et al., "Mapping the Depth Dependence of Shear Properties in Articular Cartilage", Journal of Biomechanics, vol. 41, Issue 11, Aug. 7, 2008, pp. 2430-2437.
Bumsted, "Cryotherapy for Chronic Vasomotor Rhinitis: Technique and Patient Selection for Improved Results", Laryngoscope, vol. 94, Apr. 1984, pp. 539-544.
Cole et al., "Biophysics of Nasal Airflow: A Review.", American Journal of Rhinology & Allergy, vol. 14, Issue 4, Jul. 1, 2000, pp. 245-249.
Cole et al., "The Four Components of the Nasal Valve", American Journal of Rhinology & Allergy, vol. 17, Issue. 2, Mar.-Apr. 2003, pp. 107-110.
Costa et al., "Radiographic and Anatomic Characterization of the Nasal Septal Swell Body", Arch Otolaryngol Head Neck Surg., vol. 136, No. 11, Nov. 15, 2010, 4 pages.
Girdhar-Gopal et al., "An Assessment of Postganglionic Cryoneurolysls for Managing Vasomotor Rhinitis", American Journal of Rhinology, vol. 8, No. 4, Jul.-Aug. 1994, pp. 157-164.
Golhar et al., "The effect of Cryodestruction of Vidian Nasal Branches on Nasal Mucus Flow in Vasomotor Rhinitis", Indian Journal of Otolaryngology, vol. 33, No. 1, Mar. 1981, pp. 12-14.
Goode, "A Liquid Nitrogen Turbinate Probe for Hypertrophic Rhinitis", Arch Otolaryngol., vol. 103, 1977, p. 431.
Griffin et al., "Effects of Enzymatic Treatments on the Depth-Dependent Viscoelastic Shear Properties of Articular Cartilage.", Journal of Orthopaedic Research, vol. 32, Issue12, Dec. 2014, pp. 1652-1657.
Gurelik et al., "The Effects of the Electrical Stimulation of the Nasal Mucosa on Cortical Cerebral Blood Flow in Rabbits", Neuroscience Letters, vol. 365, Jan. 13, 2004, pp. 210-213.
Kjærgaard et al., "Relation of Nasal Air Flow to Nasal Cavity Dimensions", Arch Otolaryngol Head Neck Surg, vol. 135, No. 6, Jun. 2009, pp. 565-570.
Mehra et al., "Cryosurgery in Vasomotor Rhinitis—An Analysis of 156 Patients", Indian Journal of Otolaryngology, vol. 42, No. 3, Sep. 1990, pp. 95-98.
Ozenberger, "Cryosurgery for the Treatment of Chronic Rhinitis", Laryngoscope, vol. 83, No. 4, 1973, pp. 508-516.
Ozenberger, "Cryosurgery in Chronic Rhinitis", The Laryngoscope, vol. 80, No. 5, May 1970, pp. 723-734.
Principato, "Chronic Vasomotor Rhinitis: Cryogenic and Other Surgical Modes of Treatment", The Laryngoscope, vol. 89, 1979, pp. 619-638.
Rao, "Cryosurgery on Inferior turbinate hypertrophy under topical anaesthesia—is it boon in electricity deprived places", National Journal of Otorhinolaryngology and Head & Neck Surgery, vol. 1 (10), No. 1, Apr. 2013, pp. 7-9.
Sanu et al., "Postnasal Drip Syndrome : Two Hundred Years of Controversy Between UK and USA", Rhinology, vol. 46, 2008, pp. 86-91.
Schwartz, "Autonomix Neurophysiologic Sensing Technology", Autonomix Medical, Inc. Paper, Aug. 1, 2016, 4 pages.
Settipane et al., "Update on Nonallergic Rhinitis", Annals of Allergy Asthma & Immunology, vol. 86, Issue 5, May 2001, pp. 494-508.
Silverberg et al., "Structure-Function Relations and Rigidity Percolation in the Shear Properties of Articular Cartilage", Biophysical Journal, vol. 107, No. 7, Oct. 7, 2014, pp. 1721-1730.
Stewart et al., "Development and validation of the Nasal Obstruction Symptom Evaluation (NOSE) scale", Otolaryngology—Head and Neck Surgery, vol. 130, No. 2, Feb. 2004, pp. 157-163.
Strome, "A long-term assessment of cryotherapy for treating vasomotor instability", vol. 69, No. 12, Available Online at http://apps.webofknowledge.com.laneproxy.stanford.edu/OutboundServic...marked_list_candidates=1&excludeEvent.Config=ExcludeIfFromFullRecPage, Dec. 1990, pp. 839-842.
Stupak, "Endonasal Repositioning of the Upper Lateral Cartilage and the Internal Nasal Valve", Annals of Otology, Rhinology & Laryngology, vol. 120, No. 2, Feb. 2011, pp. 88-94.
Terao et al., "Cryosurgery on Postganglionic Fibers (Posterior Nasal Branches) of the Pterygopalatine Ganglion for Vasomotor Rhinitis", Acta Otolaryngol., vol. 96, 1983, pp. 139-148.
Bleier, B. et al., "Endoscopic anatomy of the postganglionic pterygopalatine innervation of the posterolateral nasal mucosa", International Forum of Allergy & Rhinology, vol. 1, No. 2, Mar./Apr. 2011, 5 pages.

* cited by examiner

View A-A

View B-B

Section A-A

Section B-B

APPARATUS AND METHODS FOR TREATING RHINITIS

CROSS-REFERENCES TO RELATED APPLICATIONS

The present application is a Continuation of U.S. application Ser. No. 15/693,216 filed Aug. 31, 2017, which is now U.S. Pat. No. 10,028,781; which is a Divisional of U.S. application Ser. No. 15/242,362 filed Aug. 19, 2016, which is now U.S. Pat. No. 9,763,723; which is a Continuation of U.S. application Ser. No. 14/503,060 filed Sep. 30, 2014, which is now U.S. Pat. No. 9,687,288; which claims priority to U.S. Provisional Application Ser. No. 61/884,547 filed Sep. 30, 2013; and 62/015,468 filed Jun. 22, 2014; the full disclosures which are incorporated herein by reference in their entirety for all purposes.

FIELD OF THE INVENTION

The present invention is related to devices and methods for ablating regions of tissue. More particularly, the present invention is related to devices and methods for ablating regions of tissue such as through cryogenic ablation of tissue regions within the nasal cavity for treating conditions such as rhinitis.

BACKGROUND OF THE INVENTION

The human nose is responsible for warming, humidifying and filtering inspired air. The nose is mainly formed of cartilage, bone, mucous membranes and skin. The right and left nasal cavities extend back to the soft palate, where they merge to form the posterior choanae. The posterior choanae opens into the nasopharynx. The roof of the nose is formed, in part, by a bone known as the cribriform plate. The cribriform plate contains numerous tiny 20 perforations through which sensory nerve fibers extend to the olfactory bulbs. The sensation for smell occurs when inhaled odors contact a small area of mucosa in the superior region of the nose, stimulating the nerve fibers that lead to the olfactory bulbs.

The nasal turbinates are three bony processes that extend inwardly from the lateral walls of the nose and are covered with mucosal tissue. These turbinates serve to increase the interior surface area of the nose and to impart warmth and moisture to air that is inhaled through the nose. The mucosal tissue that covers the turbinates is capable of becoming engorged with blood and swelling or becoming substantially devoid of blood and shrinking, in response to changes in physiologic or environmental conditions. The curved edge of each turbinate defines a passage way known as a meatus. For example, the interior meatus is a passageway that passes beneath the inferior turbinate. Ducts, knows as the nasolacrimal ducts, drain tears from the eyes into the nose through openings located within the interior meatus. The middle meatus is a passageway that extends inferior to the middle turbinate. The middle meatus contains the semilunar hiatus, with openings or Ostia leading into the maxillary, frontal, and anterior ethmoid sinuses. The superior meatus is located between the superior and medial turbinates.

The turbinates are autonomically innervated by nerves arising from the Vidian nerve which contains sympathetic and parasympathetic afferents that can modulate the function of the turbinates to either increase (parasympathetic) or decrease (sympathetic) activity of the submucosal layer. The pterygoid canal carries both parasympathetic and sympathetic fibers, namely the vidian nerve, to the sphenopalatine ganglion. Exclusive of the sphenopalatine foramen (SPF) contents, additional posterolateral neurovascular rami project from the sphinopaletine ganglion via multiple individual postganglionic rams to supply the nasal mucosa. The most common locations for these rami are within 1 cm posterosuperior to the horizontal attachment of the inferior turbinate, within 5 mm anteroinferior to this attachment, and the palatine bone via a foramen distinct from the SPF. Also, Blier et al. showed that interfascicle anastomotic loops in some cases, are associated with at least 3 accessory nerves. Based on Blier et al., work each accessory nerve could be proximally traced directly to the PPG or greater palatine nerve.

Rhinitis is defined as inflammation of the membranes lining the nose, characterized by nasal symptoms, including itching, rhinorrhea, and/or nasal congestion. Chronic Rhinitis affects tens of millions of people in the US and is a leading cause for patients to seek medical care. Medical treatment has been shown to have limited effects for chronic rhinitis sufferers and requires daily medication use or onerous allergy treatments and up to 20% of patients may be refractory.

In addition to the medications turbinate reduction surgery (RF and micro-debridement) both have temporary duration of effect of 1-2 years and can result in complications including mucosal sloughing, acute pain and swelling, overtreatment and bone damage. Additionally, turbinate reduction does not treat the symptom of rhinorrhea. It is thought that parasympathetic effect of the vidian nerve predominates so that, on transecting it, the result is decreased rhinitis and congestion. This pathophysiology has been confirmed as surgical treatment of the vidian nerve has been tried with great success; however, the procedure is invasive, time consuming and potentially can result in dry eyes due to autonomic fibers in the vidian nerve that supply the lacrimal glands.

Golding-Wood, who recommended cutting the parasympathetic nerve fibers in the vidian canal to decrease the parasympathetic tone to the nasal mucosa, introduced a different approach for the treatment of hypersecretion in 1961. Various approaches to the vidian canal were subsequently developed, and the method was widely employed in the 1970s. However, the original technique was abandoned at the beginning of the 1980s because of its irreversible complications such as dry eyes.

Recent studies have shown that selectively interrupting the Post Nasal Nerves (PNN) in patients with chronic rhinitis improves their symptoms while avoiding the morbidities associated with vidian neurectomy.[1] The study by Ikeda et. al suggests that the effect of an anticholinergic drug on nasal symptoms resembled that of PNN resection in patients with chronic rhinitis. Based on his study the glandular mucosal acinar cells were significantly reduced after the PNN resection. The reduction in glandular cells may be explained by decreased secretion of the nerve growth factor or epidermal growth factor regulated by acetylcholine, a major neurotransmitter of parasympathetic systems.

Posterior nasal neurectomy, initially developed by Kikawada in 1998 and later modified by Kawamura and Kubo, is an alternative method in which neural bundles are selectively cut or cauterized from the sphenopalatine foramen. Autonomic and sensory nerve fibers that pass through the foramen anatomically branch into the middle and inferior turbinate and are distributed around the mucosal layer of the nose, Therefore, selective neurectomy at this point enables physicians to theoretically avoid surgical complications such as inhibition of lacrimal secretion.

BRIEF SUMMARY OF THE INVENTION

The Posterior Nasal Nerves (PNN) innervate, inferior, middle, and inferior turbinates. Ablating these nerves leads to a decrease in or interruption of parasympathetic nerve signals that contribute to congestion and rhinorrhea in patients with chronic rhinitis (allergic or vasomotor). The devices and methods described herein are configured to be used for ablating one or more of these branches to reduce or eliminate rhinitis, e.g., ablating the Posterior Nasal Nerves (PNN).

Generally, several various apparatus and methods may be used to ablate the PNN as described below. One method for treating the tissue region within a nasal cavity in proximity to the PNN may be comprised of introducing a distal end of a probe shaft through the nasal cavity, wherein the distal end has an end effector with a first configuration having a low-profile which is shaped to manipulate tissue within the nasal cavity. The distal end may be positioned into proximity of the tissue region having the PNN associated with a middle or inferior nasal turbinate. Once suitably positioned, the distal end may be reconfigured from the first configuration to a second configuration, which is shaped to contact and follow the tissue region. The distal end may then be used to ablate the PNN within the tissue region utilizing a number of different tissue treatment mechanisms, e.g., cryotherapy, as described herein.

In treating the tissue region in one variation, the distal end may be positioned specifically into proximity of the tissue region which is surrounded by the middle nasal turbinate, inferior nasal turbinate, and lateral wall forming a cul-de-sac and having the PNN associated with the middle or inferior nasal turbinate. The distal end may be reconfigured to treat the tissue region accordingly.

Various configurations for the distal end may be utilized in treating the tissue region so long as the distal end is configured for placement within the narrowed confines of the nasal cavity and more specifically within the confines of the cul-de-sac defined by the tissue region surrounding the middle nasal turbinate, inferior nasal turbinate, and lateral nasal tissue wall.

One example of a surgical probe configured for ablating the tissue region within such narrowed confines includes a surgical probe apparatus having a surgical probe shaft comprising an elongated structure with a distal end and a proximal end, an expandable structure attached to the distal end of the probe shaft, the expandable structure having a deflated configuration and an expanded configuration. A lumen may be defined through the shaft in fluid communication with an interior of the expandable structure. A member may be attached to the distal end and extend within the expandable structure which encloses the member such that the member is unattached to the interior of the expandable structure. Moreover, the member may define an atraumatic shape, which is sized for pressing against and manipulating through the expandable structure the lateral nasal wall or other tissue proximate to the PNN.

An example of utilizing such a structure in treating the tissue region may generally comprise advancing the distal end of the surgical probe shaft through the nasal cavity and into proximity of the tissue region having PNN associated with a middle or inferior nasal turbinate and introducing a cryogenic fluid into the expandable structure attached to the distal end of the probe shaft such that the expandable structure inflates from a deflated configuration into an expanded configuration against the tissue region.

As described above, a position of the member relative to the tissue region may be adjusted where the member is attached to the distal end of the probe shaft and extends within the expandable structure, which encloses the member such that the member is unattached to an interior of the expandable structure. The practitioner may apply a pressure against the distal end such that the member is pressed against the interior of the expandable structure which in turn is pressed against the tissue region having the PNN, wherein the member defines an atraumatic shape which is sized for pressing against and manipulating the tissue region. The member may be maintained against the interior of the expandable structure and the tissue region until the tissue region is cryogenically ablated.

Any of the ablation devices herein can be used to ablate a single nerve branch or multiple nerve branches.

One aspect of this invention is a surgical probe configured for ablating, the posterior nasal nerve associated with a nasal turbinate. The surgical probe, in one example, comprises a surgical shaft with a proximal end and a distal end, a surgical hand piece disposed on the proximal end, and a coiled spring-like structure disposed on the distal end. The coiled spring-like structure is a hollow structure comprising a closely pitched wire coil forming a central lumen, and an outer surface. The surgical hand piece comprises a pressurized liquid cryogen reservoir and a user actuated liquid cryogen flow control valve. There is at least one liquid cryogen path through the probe shaft in fluidic communication with the liquid flow control valve within the hand piece, and the spring-like coiled structure.

The pressurized cryogen liquid reservoir contains a liquid cryogen, e.g., nitrous oxide, but may also be another cryogenic liquid such as liquid carbon dioxide, or a liquid chlorofluorocarbon compound, etc. The distal spring-like structure may be configured as a liquid cryogen evaporator, either as a closed liquid cryogen evaporator, or as an open liquid cryogen evaporator.

In the closed evaporator configuration the inner central lumen of the spring-like structure is lined with a polymeric liner. Liquid cryogen is introduced into the central lumen through liquid cryogen supply line that is connected to the liquid cryogen reservoir in the handle, and runs coaxially through the probe shaft. The evaporated liquid cryogen may be vented to the room, e.g., through the probe shaft to a vent port in the hand piece, or in the vicinity of the proximal end of the probe shaft. No liquid or gas cryogen is introduced into the patient's nasal cavity.

In the open liquid cryogen evaporator configuration, the evaporated cryogen may exit the central lumen of the spring-like structure between the wire coils, and into the nasal cavity of the patient. Precautions to prevent the patient from inhaling the cryogen gas may be taken. As an example, a distal occlusion balloon may be used to occlude the distal nasal passageway.

The surgical probe may be configured so that the surgeon can press the distal spring like structure against the lateral nasal wall proximate to the target posterior nasal nerve. The spring-like structure is configured to conform to the morphology of the lateral nasal wall and to evenly engage the lateral nasal wall with a substantially uniform contact pressure. The probe shaft may have a length between, e.g., approximately 4 cm and 10 cm, and a diameter between, e.g., approximately 1 mm and 4 mm. The distal spring-like structure may have an outer diameter that approximates the diameter of the probe shaft, or may be larger or smaller in diameter. The extended length of the spring-like structure may be between, e.g., approximately 0.5 cm and 1.5 cm.

The surgical probe may be supplied with the distal spring-like structure configured straight and coaxial with the probe shaft. In another embodiment, the distal spring like. structure is supplied with a lateral curve with the proximal end of the spring-like structure in a tangential relationship with the distal end of the probe shaft. In another embodiment, the surgical probe may be supplied with the distal spring-like structure in a loop configuration where both ends of the spring-like structure are in a substantially tangential relationship with the distal end of the probe shaft.

The distal spring-like structure is substantially flexible along its axis; however, the structure may also be at least partly malleable and configured for form shaping, by the user. Form shaping of the spring-like structure may be done manually by the surgeon, or alternatively the surgical probe may be supplied with the distal spring like structure in various predetermined/factory configurations. Various lengths, shapes, and diameters of the spring-like structure of the surgical probe may be produced and supplied to the end user.

In one embodiment, the distal spring-like structure is configured as a cryogenic liquid, evaporator, where cryogenic liquid is delivered to the central lumen of the distal spring like structure. The liquid then evaporates at a low temperature, which causes the outer surface of the spring-like structure to reach a temperature that is sufficiently cold to ablate surrounding tissue and the function of the target posterior nasal nerve. The surgical probe may be configured so that the temperature of the outer surface of the spring-like structure is between −20 Deg. C. and −50 Deg. C. during liquid cryogen evaporation.

The surgical hand piece may comprise a factory filled liquid cryogen reservoir, and a user actuated cryogen flow control valve. The surgical hand piece may be configured so that it is held by the user like a pistol having a pistol grip where the cryogen flow valve actuator is configured like a pistol trigger. In an alternate embodiment, the surgical hand piece is configured for the surgeon to grip it substantially like a writing utensil, with a button located in the vicinity of the index finger configured to actuate the cryogen flow control valve. In a third embodiment, the surgical hand piece may be configured to be held by the surgeon substantially like a pistol or a writing utensil, with a pistol like trigger configured to actuate a cryogen flow control valve, and a button in the vicinity of the index finger configured to actuate the same or a second cryogen control valve.

In another embodiment of this invention, the distal spring-like structure is encompassed by an expandable membranous structure. The expandable membranous structure may be a hollow bulbous structure with a single ostium configured for pressure tight bonding to the distal end of the probe shaft. The expandable membranous structure may be configured as a liquid cryogen evaporation chamber. Liquid cryogen is introduced into the expandable membranous structure from the encompassed spring-like structure.

The evaporated cryogen may be exhausted into the room through the probe shaft to a vent port in the hand piece, or in the vicinity of the proximal end of the probe shaft. The surgical probe is configured so that the expandable membranous structure expands to a predetermined, shape in response to liquid cryogen evaporation. The pressure within the expandable membranous structure during cryogen evaporation may be regulated. The regulation means may comprise a pressure relief valve disposed in the gas exhaust path. The expandable membranous structure may be formed from an elastomeric material such as silicone rubber, or a urethane rubber. Alternatively, the expandable membranous structure may be formed from a substantially non-elastomeric material such as polyurethane or PET. The expandable membranous structure is configured so the shape and the size of the structure matches the shape and the size of the cul-de-sac of the lateral nasal wall defined by the tail of the middle turbinate, lateral nasal wall and the inferior turbinate, which is the target location for the ablation of the posterior nasal nerves for the treatment of rhinitis. Matching the size and shape of the expandable membranous structure to the size and shape of the target anatomy facilitates optimal tissue freezing and ablation of posterior nasal nerves. The expandable membranous structure may have an expanded diameter between approximately 3 mm and 12 mm in one radial axis, and may be configured such that the expanded diameter in one radial axis is different than another radial axis.

The probe shaft may be straight and rigid, or alternatively may be substantially malleable and configured for form shaping by the user. The probe shaft may be straight and rigid in the proximal region, and substantially malleable in the distal region and configured for form shaping by the user.

The surgical probe may be configured with a camera and a light source disposed in the vicinity of the distal end of the probe shaft. The camera and light source may be configured to provide the surgeon with images of the nasal anatomy in order to identify anatomical landmarks for guiding the surgical placement of the distal spring-like structure against the lateral nasal wall proximate to the target posterior nasal nerve. The camera and light source may be further configured to image tissue freezing to provide the surgeon with visual feedback on the progress of a cryo-ablation of the nasal tissue innervated by posterior nasal nerves.

The surgical probe may also be configured with at least one temperature sensor disposed in the vicinity of the distal end. The temperature sensor may be configured to sense a temperature indicative of cryogen evaporation temperature, or a temperature indicative of a tissue temperature of surgical interest. Signals from the at least one temperature sensor may be used to servo-control the flow of cryogen in order to control a tissue temperature or to control the evaporation temperature. A temperature sensor may also be used in an informational display, or for system alarms or interlocks.

The surgical probe may be configured to automatically adjust the flow rate of liquid cryogen in response to one or more of the following parameters: evaporator temperature, evaporator pressure, tissue temperature, evaporator exhaust gas temperature, or elapsed cryogen flow time. The flow rate may be adjusted in a continuous analog manner, or by an alternating on/off flow modulation.

Another aspect of this invention is a method for treating rhinitis by ablating posterior nasal nerves associated with a middle or inferior nasal turbinate. The method may comprise inserting the distal end of a surgical probe configured for cryoneurolysis into a nostril of a patient with the surgical probe comprising a hollow probe shaft that is, e.g., substantially rigid. The surgical hand piece disposed on the proximal end of the probe shaft may comprise a liquid cryogen reservoir and, e.g., a user actuated liquid cryogen flow control valve. A cryogen liquid evaporator comprising, e.g., a spring-like structure configured as a liquid cryogen evaporator, may be disposed on the distal end of the probe shaft. The distal spring-like structure may be positioned against the lateral nasal wall proximate to a target posterior nasal nerve and then a flow of liquid cryogen to the spring-like structure may be activated for a period of time sufficient to cryo-ablate a target area in the nose containing posterior nasal nerves.

The method may further involve the targeting of at least one additional posterior nasal nerve, either within the ipsilateral nasal cavity, or a posterior nasal nerve in a contralateral nasal cavity.

The method may comprise the use of a surgical probe which has an expandable membranous or non-membranous structure that encompasses the distal spring-like structure and which is configured as an expandable liquid cryogen evaporation chamber. The expandable membranous structure may be configured to be a predetermined size and shape that matches the size and shape of the nasal wall anatomy proximate to the target posterior nasal nerve. The surgical probe may be configured so the expandable membranous structure expands to its predetermined size and shape in response to liquid cryogen evaporation within.

The method may comprise controlling the flow of the liquid cryogen into the evaporation chamber based on at least one predetermined parameter, which may comprise one or more of the following parameters: cryogenic liquid flow rate, cryogenic liquid flow elapsed time, cryogenic liquid evaporation pressure, cryogenic liquid evaporation temperature, cryogenic gas exhaust temperature, visual determination of tissue freezing, ultrasonic determination of tissue freezing, or the volume of cryogenic liquid supplied by the cryogenic liquid reservoir.

The method may comprise determining the location of the target posterior nasal nerve, which may involve one or more of the following targeting techniques: endoscopic determination based on the nasal anatomical landmarks, electrical neuro-stimulation of the target posterior nasal nerve while observing the physiological response to the stimulation, electrical neuro-blockade, while observing the physiological response to the blockade, or identification of the artery associated with the target posterior nasal nerve using, e.g., ultrasonic or optical doppler flow techniques.

Yet another aspect comprises an embodiment of a surgical probe which is configured for ablation where the surgical probe comprises a surgical probe shaft comprising an elongated structure with a distal end and a proximal end, an expandable structure attached to the distal end of the probe shaft, the expandable structure having a deflated configuration and an expanded configuration, a member attached to the distal end and extending within the expandable structure such that the member is unattached to an interior of the expandable structure, wherein the member defines a flattened shape which is sized for placement against a lateral nasal wall proximate to a posterior nasal nerve, and a lumen in fluid communication with the interior of the expandable structure.

In use, such a surgical probe may be used for treating a tissue region within a nasal cavity, generally comprising advancing a distal end of a surgical probe shaft through the nasal cavity and into proximity of the tissue region having a posterior nasal nerve associated with a middle or inferior nasal turbinate, introducing a cryogenic liquid into an expandable structure attached to the distal end of the probe shaft such that the expandable structure inflates from a deflated configuration into an expanded configuration against the tissue region, positioning a member relative to the tissue region, wherein the member is attached to the distal end of the probe shaft and extends within the expandable structure such that the member is unattached to an interior of the expandable structure, and wherein the member defines a flattened shape which is sized for placement against the tissue region proximate to the posterior nasal nerve, and maintaining the member against the tissue region until the posterior nasal nerve is cryogenically ablated.

One aspect of the invention is a cryosurgical probe apparatus for ablation of PNN function comprising a handle at the proximal end, a probe shaft with a spatula shaped cryo-ablation element mounted in vicinity of the distal end of the shaft, whereby the handle is configured for housing a cryogen source, and controlling the flow of the cryogen to the cryo-ablation element, and the geometric parameters of the probe shaft and cryo-ablation element are optimally configured for cryo-ablation of nasal mucosa containing PNN according to the surgical methods disclosed here within.

One embodiment of this invention is a cryosurgical probe apparatus for ablation of nasal mucosa innervated by PNN comprise a handle at the proximal end, a probe shaft with a bullet shaped cryo-ablation element mounted in vicinity of the distal end of the shaft, whereby the handle is configured for housing a cryogen source, and controlling the flow of the cryogen to the cryo-ablation element, and the geometric parameters of the probe shaft and cryo-ablation element are optimally configured for cryo-ablation of PNN according to the surgical methods disclosed here within.

Another embodiment of this invention is a cryo-surgical probe apparatus for ablation of PNN function comprising a handle at the proximal end, a probe shaft with a bullet shaped cryo-ablation element mounted in vicinity of the distal end of the shaft, whereby the handle is configured for housing a cryogen source, and controlling the flow of the cryogen to the cryo-ablation element, wherein the probe shaft is configured with user operable deflectable distal segment, and the geometric parameters of the probe shaft and cryo-ablation element are optimally configured for cryo-ablation of PNN according to the surgical methods disclosed here within.

Another embodiment of this invention is a cryo-surgical probe apparatus for ablation of PNN comprising a handle at the proximal end, a probe shaft with a cylindrically shaped cryo-ablation element mounted in vicinity of the distal end of the shaft, whereby the handle is configured for housing a cryogen source, and controlling the flow of the cryogen to the cryo-ablation element, wherein the cryo-ablation element comprises a linear segmented cryo-ablation element, and the geometric parameters of the probe shaft and cryo-ablation element are optimally configured for cryo-ablation of PNN according to the surgical methods disclosed here within.

Another embodiment of this invention is a cryosurgical probe apparatus for ablation of PNN comprising a handle at the proximal end, a probe shaft with a cylindrically shaped cryo-ablation element mounted in vicinity of the distal end of the shaft, whereby the handle is configured for housing a cryogen source, and controlling the flow of the cryogen to the cryo-ablation element, wherein the cryo-ablation element comprises a semi-circular cryo-ablation element, and the geometric parameters of the probe shaft and cryo-ablation element are optimally configured for cryo-ablation of target tissue containing PNN according to the surgical methods disclosed here within.

Another embodiment of this invention is a cryosurgical probe apparatus for ablation of PNN function comprising a handle at the proximal end, a probe shaft with a cylindrically shaped cryo-ablation element mounted in vicinity of the distal end of the shaft, whereby the handle is configured for housing a cryogen source, and controlling the flow of the cryogen to the cryo-ablation element, wherein the cryo-ablation element comprises a spiraled cryo-ablation element, and the geometric parameters of the probe shaft and cryo-ablation element are optimally configured for cryo-ablation of target nasal tissue containing PNN according to the surgical methods disclosed here within.

Another embodiment of this invention is a cryo-surgical probe apparatus for ablation of PNN comprising a proximal end, a probe shaft with a cryo-ablation element comprising a balloon mounted in vicinity of the distal end of the shaft, whereby the proximal end is configured for receiving a cryogen from a cryogen source with the cryogen source comprising a means controlling the flow of the cryogen to the cryo-ablation element, and the geometric parameters of the probe shaft and cryo-ablation element are optimally configured for cryo-ablation of PNN according to the surgical methods disclosed here within.

Another embodiment of this invention is a cryo-surgical probe apparatus for ablation of PNN comprising a handle at the proximal end, a probe shaft with a cylindrically shaped cryo-ablation element comprising a balloon mounted in vicinity of the distal end of the shaft, whereby the handle is configured for housing a cryogen source, and controlling the flow of the cryogen to the cryo-ablation element, and the geometric parameters of the probe shaft and cryo-ablation element are optimally configured for cryo-ablation of target nasal tissue containing PNN according to the surgical methods disclosed here within.

Another embodiment of this invention is a cryo-surgical probe apparatus for ablation of PNN comprising a handle at the proximal end, a probe shaft with a cylindrically shaped cryo-ablation element mounted comprising a balloon with two lateral chambers disposed in the vicinity of the distal end of the shaft, whereby the handle is configured for housing a cryogen source, and controlling the flow of the cryogen to the cryo-ablation element, wherein one chamber of the balloon is configured as a cryogen expansion chamber, and the second chamber is configured as a thermal insulation chamber, and the geometric parameters of the probe shaft and cryo-ablation element are optimally configured for cryo-ablation of PNN according to the surgical methods disclosed here within.

Another embodiment of this invention is a cryosurgical probe apparatus for ablation of PNN comprising a handle at the proximal end, a probe shaft with a "T" shaped cryo-ablation element comprising a balloon mounted in vicinity of the distal end of the shaft, whereby the handle is configured for housing a cryogen source, and controlling the flow of the cryogen to the cryo-ablation element, and the geometric parameters of the probe shaft and cryo-ablation element are optimally configured for cryo-ablation of PNN according to the surgical methods disclosed here within.

Another embodiment of this invention is a cryo-surgical probe apparatus for ablation of PNN function comprising a handle at the proximal end, a probe shaft with a "J" shaped cryo-ablation element comprising a balloon mounted in vicinity of the distal end of the shaft, whereby the handle is configured for housing a cryogen source, and controlling the flow of the cryogen to the cryo-ablation element, and the geometric parameters of the probe shaft and cryo-ablation element are optimally configured for cryo-ablation of PNN according to the surgical methods disclosed here within.

Another embodiment of this invention is a cryo-surgical probe apparatus for ablation of PNN comprising a handle at the proximal end, a probe shaft with a cryo-ablation element mounted in vicinity of the distal end of the shaft, whereby the handle is configured for housing a cryogen source, and controlling the flow of the cryogen to the cryo-ablation element, wherein a suction means associated with the cryo-ablation element is configured for stabilizing the position of the cryo-ablation element against the target tissue, and the geometric parameters of the probe shaft and cryo-ablation element are optimally configured for cryo-ablation of PNN according to the surgical methods disclosed here within.

One aspect of this is a method for cryo-surgical ablation of PNN comprising placing a film of oil or gel on the surface of a cryo-ablation element, then pressing the cryo-ablation element against the lateral wall of a nasal cavity adjacent to a PNN, then ablating the function of the PNN with the cryo-ablation element, whereby the oil or gel prevents frozen nasal tissue from adhering to the cryo-ablation element.

In another aspect of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector in the vicinity of the handle configured to connect the RF ablation element to a source of radiofrequency energy, whereby the geometric parameters of the probe shaft and RF ablation element are optimally configured for RF ablation of PNN function according to the surgical methods disclosed here within.

One embodiment of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, and a fluid connector disposed in the vicinity of the handle to connect at least one fluid port associated with the RF ablation element with a source of pressurized liquid, whereby the geometric parameters of the probe shaft and RF ablation element are optimally configured for RF ablation of PNN according to the surgical methods disclosed here within.

Another embodiment of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according to the surgical methods disclosed here within, wherein the RF ablation element comprises a monopolar electrosurgical configuration comprising one or more electrodes.

Another embodiment of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according to the surgical methods disclosed here within, wherein the RF ablation element comprises a bi-polar electrosurgical configuration comprising two or more electrodes.

Another embodiment of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element, to a source of radiofrequency energy, whereby the geometric parameters of the probe shaft and RF ablation element are optimally configured for RF ablation of PNN according to the surgical methods disclosed here within, wherein the RF ablation element is disposed in the vicinity of the distal end of the shaft on a cylindrical, "J" shaped, "U" shaped or "T" shaped structure.

Another embodiment of this invention is an electrosurgical probe apparatus for ablation of PNN function comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according to the surgical methods disclosed here within, wherein the RF ablation element is configured in a lateral or radial arrangement.

Another embodiment of this invention is n electrosurgical probe apparatus for ablation of PNN function comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according, to the surgical methods disclosed here within, wherein the RF ablation element comprises a circular array of domed electrodes disposed on a flat electrically insulative surface, with the domed electrodes optionally associated with a fluid irrigation port.

Another embodiment of this invention is an electrosurgical probe for ablation of PNN function comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according to the surgical methods disclosed here within, wherein the RF ablation element comprises a linear array of domed electrodes disposed on a flat electrically insulative surface, with the domed electrodes optionally associated with a fluid irrigation port, and a needle configured for injecting a liquid into a sub-mucosal space.

Another embodiment of this invention is an electrosurgical probe apparatus for ablation of PNN comprising a handle at the proximal end, a probe shaft with a radiofrequency (RF) ablation element comprising at least one radiofrequency (RF) electrode mounted in the vicinity of the distal end of the shaft, an electrical connector disposed in the vicinity of the handle configured to connect the RF ablation element to a source of radiofrequency energy, whereby the geometric parameters of the probe shaft and RF ablation element are optimally configured for RF ablation of PNN according to the surgical methods disclosed here within, wherein the RF ablation element comprises at least one needle configured for interstitial RF ablation.

Another embodiment of this invention is an electrosurgical probe apparatus for ablation of PNN comprising a handle at the proximal end, a probe shaft comprising a distal and proximal end, and an integrated circuit comprising an RF generator disposed in the vicinity of the handle and an RF ablation element disposed in the vicinity of the distal end of the shaft, whereby the geometric parameters of the probe shaft and RF ablation element are optimally configured for RF ablation of PNN according to the surgical methods disclosed here within.

In another aspect of this invention is an ultrasonic energy emitting probe apparatus for ablation of PNN comprising, a handle at the proximal end, a probe shaft with an ultrasonic energy ablation element comprising at least one ultrasonic energy emitter mounted in the vicinity of the distal end of the shaft, an electrical connector in the vicinity of the handle configured to connect the ultrasonic energy emitter to an ultrasonic energy generator, whereby the geometric parameters of the probe shaft and ultrasonic energy emitter are optimally configured for ultrasonic energy ablation of PNN according to the surgical methods disclosed here within.

In another embodiment of this invention is an ultrasonic energy emitting probe apparatus for ablation of PNN comprising a handle at the proximal end, a probe shaft with an ultrasonic energy ablation element comprising at least one ultrasonic energy emitter mounted in the vicinity of the distal end of the shaft, an electrical connector in the vicinity of the handle configured to connect the ultrasonic energy emitter to an ultrasonic energy generator; at least one fluid path in communication between at least one fluid connector in the vicinity of the handle and the ultrasonic energy emitter configured to cool the ultrasonic energy emitter during ultrasonic energy emission, whereby the geometric parameters of the probe shaft and ultrasonic energy emitter are optimally configured for ultrasonic energy ablation of PNN according to the surgical methods disclosed here within.

DETAILED DESCRIPTION OF THE INVENTION

Figure 1:
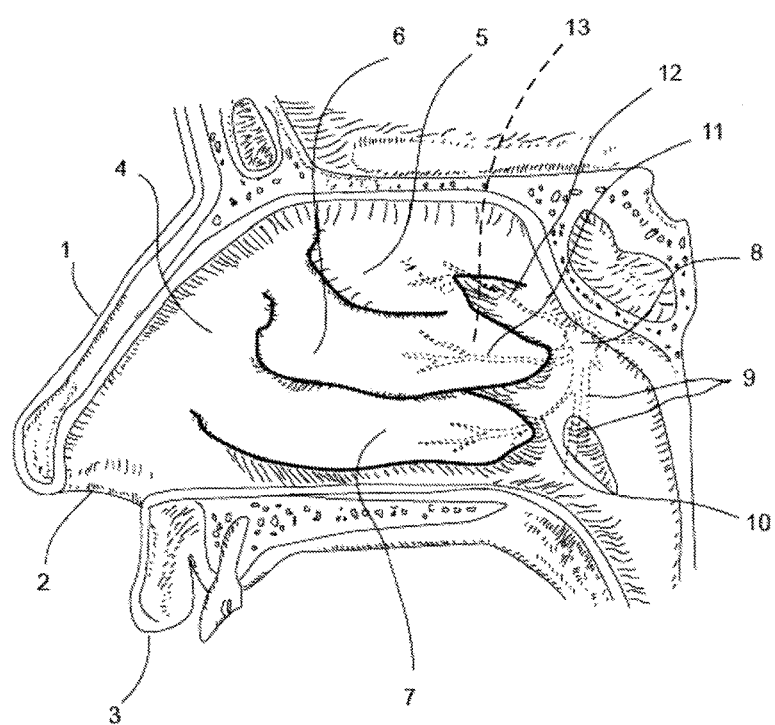
FIG. 1 is an internal lateral view of the nasal canal showing the relevant nasal anatomy and the targeted region of the lateral nasal wall for cryo-ablation of posterior nasal nerve function.

FIG. 1 is an internal view of the nasal cavity showing the relevant nasal anatomy. Shown for orientation is the lateral nasal cavity wall 4, the nose 1, nostril 2, and the upper lip 3. The superior turbinate 5, middle turbinate 6, and inferior turbinate 7 are depicted along with the associated nerves relevant to this invention shown in dashed lines. The posterior nasal nerves 10, 11 and 12 are responsible for the parasympathetic control of the nasal mucosa including turbinates. These posterior nasal nerves (PNNs) originate from the sphenopalatine ganglion. At times other accessory posterior nasal nerves (APNNs) may originate from the greater palatine nerve or from the bony plate underneath the mucosa.

Figure 2:
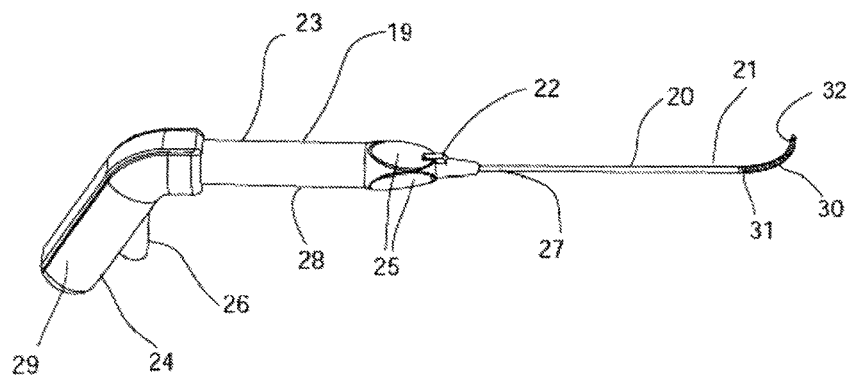
FIG. 2 is a schematic illustration of a surgical probe configured for cryo-ablation of posterior nasal nerve function for the treatment of rhinitis.

FIG. 2 is a schematic illustration of surgical probe 29, which is configured for cryo-ablation of posterior nasal nerve function for the treatment of rhinitis. Surgical probe 29 comprises: probe shaft 20, with shaft distal end 21 and shaft proximal end 27; surgical hand piece 23, e.g., with pistol grip 24, finger grip 25, pistol trigger flow control valve actuator 26, button flow control flow valve actuator 22, finger grip barrel 28, cryogen reservoir housing 29; and distal end effector 30 (e.g., spring-like structure) with end effector proximal end 31, and end effector distal end 32. Surgical probe shaft 20 is between, e.g., approximately 1 mm and 4 mm in diameter and between, e.g., approximately 4 cm and 10 cm in length. Surgical probe shaft 20 may be fabricated from various biocompatible materials such as a surgical grade stainless steel hypodermic tube, or may alternatively be fabricated from a polymeric extrusion. Surgical probe shaft 20 comprises at least one liquid cryogen delivery channel between shaft distal end 21 and shaft proximal end 27. Probe shaft 20 is substantially rigid in one variation, and may also be configured to be malleable and shape formable by the user. The distal end effector 30 is shown having, multiple variations described herein and may be optionally interchanged depending upon which particular embodiment is utilized by a practitioner.

Although probe shaft 20 is depicted to be straight, it is well within the scope of this invention probe shaft 20 may be manufactured with at least one curved segment. Surgical hand piece 23 is disposed on the proximal end 22 of probe shaft 20. Surgical hand piece 23 comprises a liquid cryogen reservoir, not shown, that may be conventionally supplied with liquid cryogen and configured for a single patient use. Alternatively, surgical hand piece 23 may be configured for use with a user replaceable liquid cryogen reservoir in the form of a cartridge. Liquid cryogen cartridges are readily commercially available from many sources. In yet another alternative, a reservoir separate from the device may be fluidly coupled to the hand piece 23. Surgical hand piece 23 may further comprise a liquid cryogen flow control valve, not shown, that may be disposed in fluidic communication with the liquid cryogen reservoir and the liquid cryogen channel in probe shaft 20.

Surgical device 29 may be configured to be held like a pistol by the surgeon or practitioner using pistol grip 24, or the surgeon or practitioner may hold surgical device 29 like a writing utensil using finger grips 25, with finger grip barrel 28 residing between the thumb and index finger of the surgeon. Surgical device 29 may be configured with, e.g., two or more liquid cryogen flow control valve actuators comprising pistol trigger liquid cryogen flow control actuator 26, which may be used to control the flow of liquid cryogen when the surgeon holds surgical device 29 using pistol grip 24. Liquid cryogen flow control actuator button 22 may be used to control the flow of liquid cryogen when the surgeon holds surgical device 29 by finger grips 25. Probe shaft 20 may be configured to be rotatably coupled to the surgical device 29 to facilitate positioning of distal end effector 30 (e.g., spring-like structure) without having to rotate the surgical device 29 excessively. Distal end effector 30 (e.g., spring-like structure), with end effector proximal end 31, and end effector distal end 32 is disposed on the distal end 21 of probe shaft 20 as shown. Distal end effector 30 (e.g., spring-like structure) is configured as a liquid cryogen evaporator, and is configured to be pressed against the lateral nasal wall within the cul-de-sac described above for cryo-ablation of at least one posterior nasal nerve. The construction and the function of distal end effector 30 (e.g., spring-like structure), and alternative embodiments are described in detail below.

Surgical device 29 may be configured as a simple mechanical device that is void of electronics as shown. Alternatively, surgical device 29 may be configured with at least one electronic function. In one embodiment, a temperature sensor may be disposed in the vicinity of distal end effector 30 (e.g., spring-like structure) and used to measure, display, or control a temperature of surgical interest. A temperature sensor may be configured to sense the temperature of evaporating cryogen within distal end effector 30 (e.g., spring-like structure). A temperature sensor may also be configured to sense the temperature of a tissue of surgical interest. The liquid cryogen control valve 22 may also optionally comprise a servo mechanism configured to respond to a sensed temperature to modulate the flow of cryogen in order to control a desired surgical parameter.

In addition to a temperature sensing capability, surgical device 29 may be configured with a camera and/or a light source disposed in the vicinity of distal end 21 of probe shaft 20. The camera and light source may be used, e.g., to identify nasal anatomical landmarks, and may be used to guide the placement of distal end effector 30 (e.g., spring-like structure) against the lateral nasal wall for a cryo-ablation of the function of a target posterior nasal nerve. An ultrasonic or optical doppler flow sensor may also be disposed in the vicinity of distal end 21 of probe shaft 20 and be used, e.g., to locate the major artery associated with the target posterior nasal nerve, as a means for locating the target posterior nasal nerve. In addition, one or more electrodes may be disposed in the vicinity of distal end 21 of probe shaft 20, which may be used for electrical stimulation or electrical blockade of the function of a target posterior nasal nerve using the observed physiological response to the stimulation or blockade to confirm correct surgical positioning of distal end effector 30 (e.g., spring-like structure) prior to a cryo-ablation and/or to confirm effectiveness of a cryo-ablation by the determination of a change in the physiological response from before and after a cryo-ablation.

Any number of temperature sensing, endoscopic instruments, servo controlled cryogen control valves, ultrasonic or optical doppler flow detection, and/or electrical nervous stimulation and blockade mechanisms may be optionally incorporated into the devices described herein. Also, providing a surgical probe as described here with a liquid cryogen reservoir that is external to the probe hand piece is also within the scope of this invention.

Figure 3A:
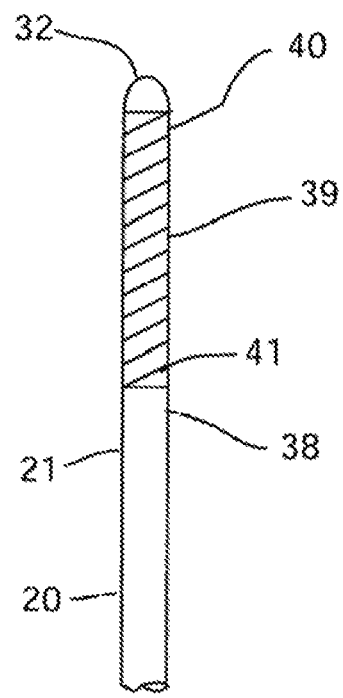
FIG. 3A is a view of the distal end of a surgical probe shaft with the spring-like structure coaxial to the surgical probe shaft.
Figure 3B:
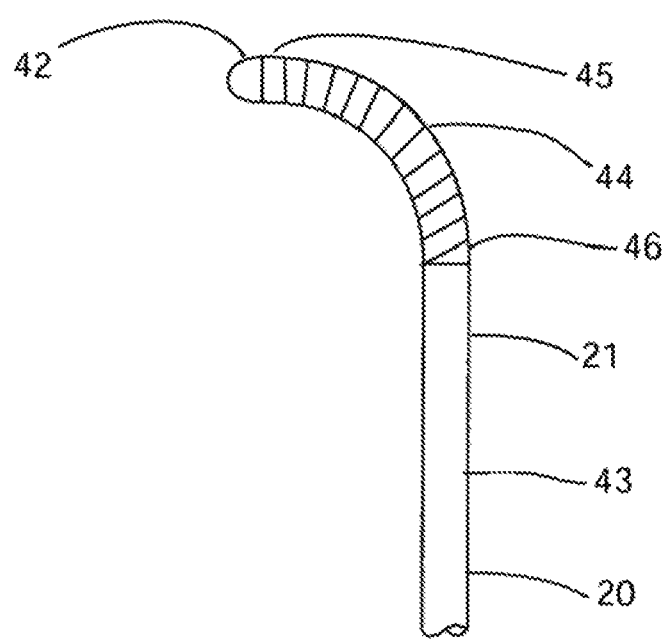
FIG. 3B is a view of the distal end of a surgical probe shaft with the spring-like structure comprising a lateral curve in a tangential relationship with the surgical probe shaft.
Figure 3C:
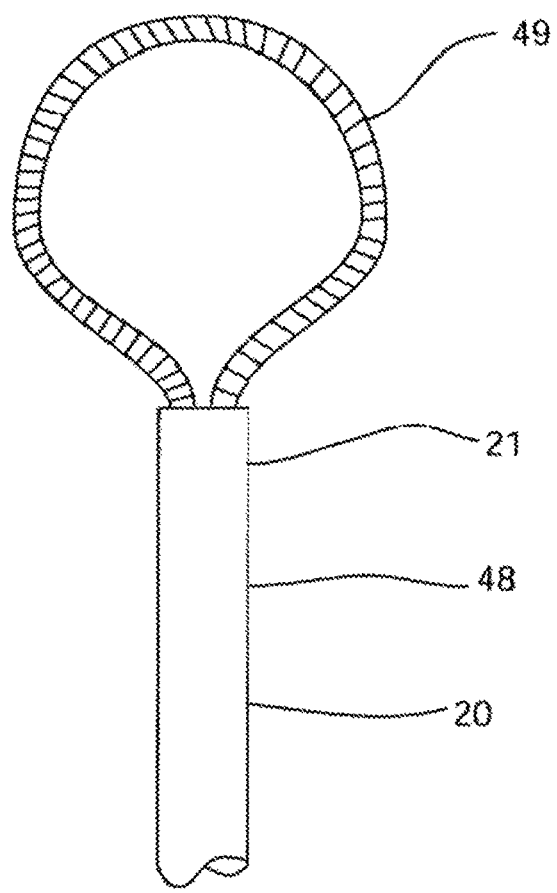
FIG. 3C is a view of the distal end of a surgical probe shaft with the spring-like structure comprising a loop or a continuous structure.

FIG. 3A is a schematic illustration of an alternative end effector embodiment, which comprises spring-like structure 39 which is configured in a coaxial arrangement with probe shaft 20. FIG. 3B is a schematic illustration of the distal end of an alternative embodiment surgical probe 43 which comprises spring-like structure 44, which is configured with a lateral curve as shown with proximal end 46 in a tangential relationship with the distal end 21 of probe shaft 20. FIG. 3C is a schematic illustration of the distal end of an alternative embodiment surgical probe 48, with spring-like structure 49 configured as a loop structure as shown, with both ends of spring-like structure 49 in a substantially tangential relationship with distal end 21 of probe shaft 20. The three alternate spring-like structure embodiments 39, 44, and 49 depicted in FIGS. 3A, 3B, and 3C are configured as liquid cryogen evaporators, where the outer surface of each spring-like structure may achieve a temperature between, approximately −20 Deg. C to −90 Deg. C., in response to liquid cryogen evaporation within. As previously described, the end effector described here may be optionally replaced by any of the other end effector embodiments described herein.

Spring-like structures 39, 44, and 49 are substantially flexible and are configured to conform to the morphology of a lateral nasal wall proximate to a target posterior nasal nerve with a substantially uniform contact pressure. Spring-like structures 39, 44, and 49 may be configured to be partially malleable and form shapeable by the user, while retaining a spring-like resilience during use. Spring-like structures 39 and 44 comprise distal end 40 and 45 respectively, and proximal end 41 and 46 respectively. Spring-like structures 39 and 44 comprise end cap 38, which functions as a pressure bulkhead defining the distal end of the liquid cryogen evaporator that resides within, which is described in detail below. Spring-like structures 39, 44, and 49 comprise a tightly coiled wire that forms a central chamber, and an outer surface. A thin polymeric liner is disposed on the inner surface of the central chamber and functions to contain the evaporating cryogen within the central chamber. Cryogen is introduced into the central chamber through a liquid cryogen supply line, which runs through probe shaft 20, and is in fluidic communication with the liquid cryogen flow control valve and the liquid cryogen reservoir previously described. Evaporated cryogen gas may be vented into the room out of the central chamber, through probe shaft 20, then out of a vent port disposed in the vicinity of proximal end 22 of probe shaft 20, not shown, or disposed in the surgical hand piece, also not shown. The construction and function of the disclosed embodiments of the spring-like structures is described in detail below.

Figure 4A:
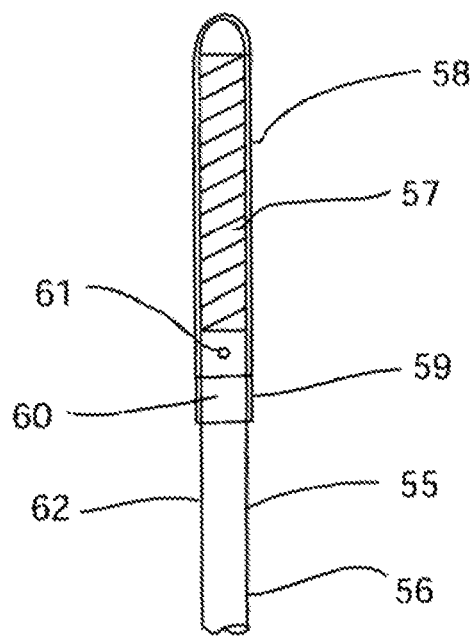
FIG. 4A is a side view of the distal end of the surgical probe shaft with the spring-like structure coaxial to the surgical probe shaft encompassed by an expandable membranous structure in an unexpanded state.
Figure 4B:
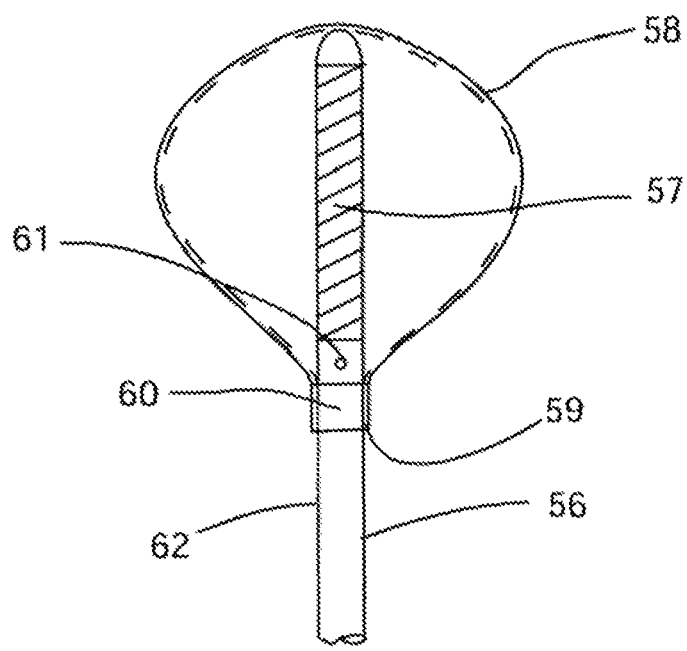
FIG. 4B is a view of the distal end of the surgical probe shaft with the spring-like structure coaxial to the surgical probe shaft encompassed by an expandable membranous structure in an expanded state.

FIG. 4A is a schematic illustration of a side view of the distal end of alternative embodiment surgical probe 55 comprising expandable membranous structure 58 encompassing, spring-like structure 57 in an un-expanded state. FIG. 4B is a schematic illustration of a side view of the distal end of surgical probe 55 with expandable structure or expandable membranous structure in an expanded state. In the depicted embodiment, expandable membranous structure 58 is configured as a liquid cryogen evaporation chamber. Liquid cryogen is introduced into the interior of expandable membranous structure 58 from spring-like structure 57. Surgical probe 55 is configured so expandable membranous structure 58 expands to a predetermined size and shape in response to liquid cryogen evaporation within. While structure 58 may be expandable to a predetermined size and shape, the structure 58 may be comprised of a non-distensible material while in other variations, structure 58 may alternatively be comprised of a distensible material which allows for the expanded size and shape to vary depending upon the volume of cryogen introduced. Surgical probe 55 is configured such that the outer surface of expandable membranous structure 58 will be between approximately –20 Deg. C to –90 Deg. C. during cryogen evaporation within. The expanded size or shape of expendable membranous structure 58 is configured to substantially contact the surface of the cul-de-sac (element 13 in FIG. 1 which indicates the region of tissue region defined and surrounded by the middle nasal turbinate, inferior nasal turbinate, and lateral wall) when pressed against the lateral nasal wall be the surgeon. Expandable membranous structure 58 may be configured to form a hollow bulbous structure in its expanded state, and comprises a single ostium 59 configured for adhesive bonding to distal end 62 of probe shaft 56 using adhesive bond 60. Cryogen exhaust vent 61 comprises at least one fenestration in distal end 62 of probe shaft 40, which is in fluidic communication with a proximal vent port, not shown, and the room. A pressure relief valve, not shown, may be disposed in the fluid path between the interior of expandable membranous structure 58 and the room to control the pressure within expandable membranous structure 58, and the degree of expansion during liquid cryogen evaporation. The construction and functionality of surgical probe embodiments comprising an expandable membranous structure are described in detail below.

Figure 5A:
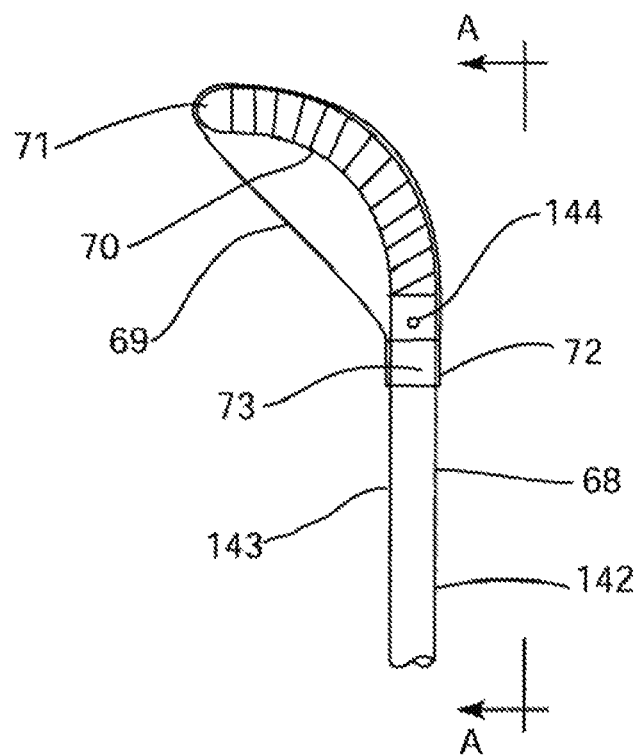
FIG. 5A is a side view of the distal end of a surgical probe shaft with the spring-like structure comprising a lateral curve in a tangential relationship with the surgical probe shaft encompassed by an expandable membranous structure in an unexpanded state.
Figure 5B:
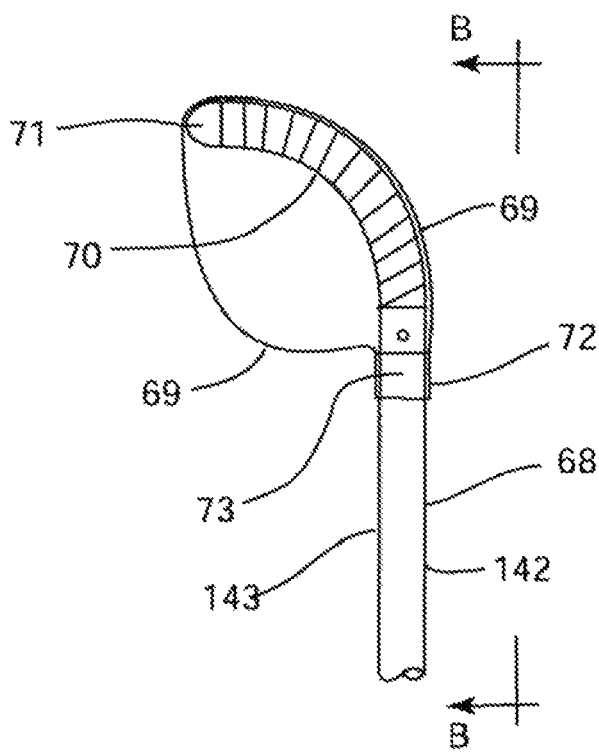
FIG. 5B is a view of the distal end of the surgical probe shaft with the spring-like structure comprising a lateral curve in a tangential relationship with the surgical probe shaft encompassed by an expandable membranous structure in an expanded state.
Figure 5C:
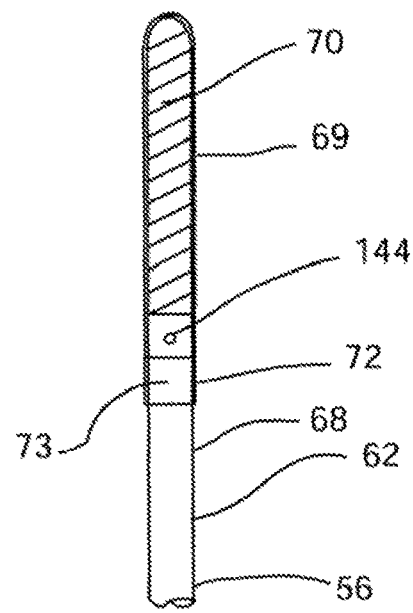
FIG. 5C is a side view that is 90 degrees from the first side view of FIG. 5A.
Figure 5D:
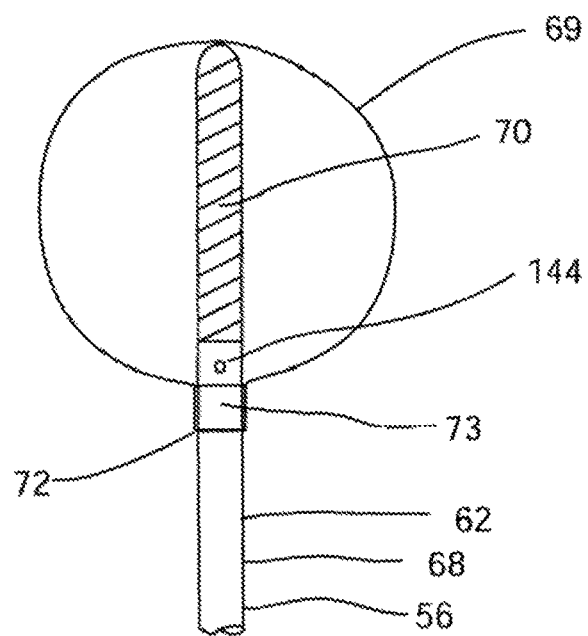
FIG. 5D is a view that is 90 degrees from the first side view of FIG. 5B.

FIG. 5A is a schematic illustration of a side view of the distal end of alternate embodiment of surgical probe 68 comprising expandable membranous structure 69 encompassing spring-like structure 70. Spring-like structure 70 is configured with a lateral bend as depicted. Expandable membranous structure 69 is depicted in its un-expanded state. FIG. 5B is a schematic illustration of the same side view in FIG. 5A of alternate embodiment surgical probe 68 with expandable membranous structure 69 in its expandable state. FIG. 5C is a schematic side view illustration taken at view A-A from FIG. 5A. FIG. 5D is a schematic side view illustration taken at view B-B from FIG. 5B. Surgical probe 68 is configured with expandable membranous structure 69 functioning as a liquid cryogen evaporation chamber as depicted in FIGS. 4A and 4B. Liquid cryogen enters the interior of expandable membranous structure 69 from encompassed spring-like structure 70. Evaporated cryogen gas exits the interior of expandable membranous structure 69 through fenestration(s) 144 in distal end 143 of probe shaft 141 and exits surgical probe 68 proximally into the room. Spring-like structure 70 is configured to pre-tension membranous structure 69 in one radial axis to a greater extent than a second radial axis in a manner that causes expansion to be constrained in the radial axis with greatest pre-tensioning. In FIGS. 5A and 5B, spring-like structure 70 is configured to pre-tension expandable membranous structure 69 to a greater extent in the radial axis that is normal to the view axis. In FIGS. 5C and 5D, spring-like structure 70 is configured to pre-tension expandable membranous structure 69 to a greater extent in the radial axis that is parallel to the view axis. FIG. 5A and FIG. 5C depict surgical probe 68 with expandable membranous structure 69 in its un-expanded state. FIGS. 5B and 5D depict surgical probe 68 with expandable membranous structure 69 in its expanded state. Pre-tensioning of expandable membranous structure 69 provides a means for achieving a predetermined expanded shape for optimal matching of the morphology of the target area of the lateral nasal wall.

Figure 6A:
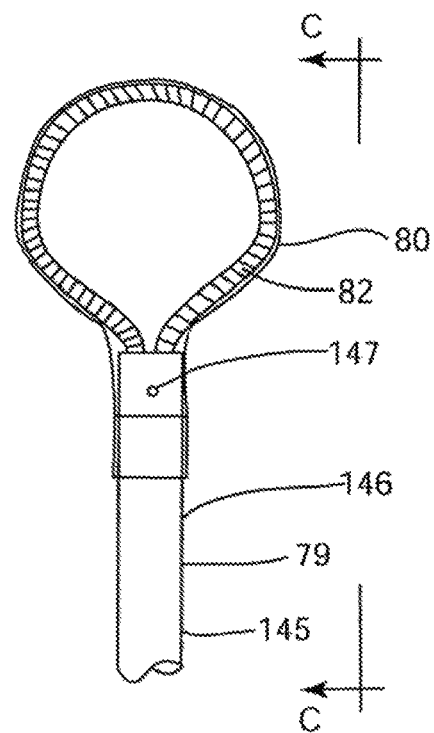
FIG. 6A is a view of the distal end of a surgical probe shaft with the spring-like structure comprising, a loop encompassed by an expandable membranous structure in an unexpanded state.
Figure 6B:
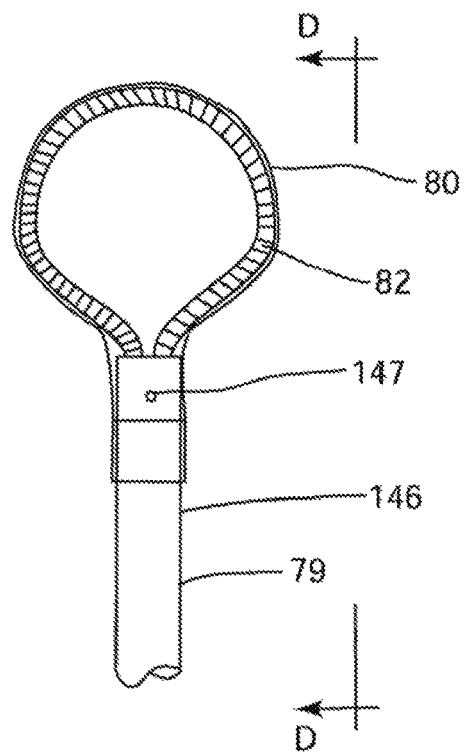
FIG. 6B is a view of the distal end of the surgical probe shaft with the spring-like structure comprising a loop encompassed by an expandable membranous structure in an expanded state.
Figure 6C:
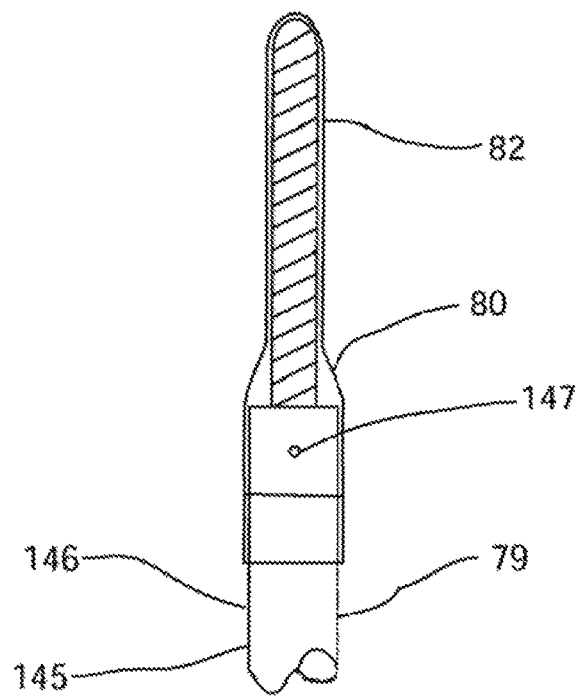
FIG. 6C is a view that is 90 degrees from the first side view of FIG. 6A.
Figure 6D:
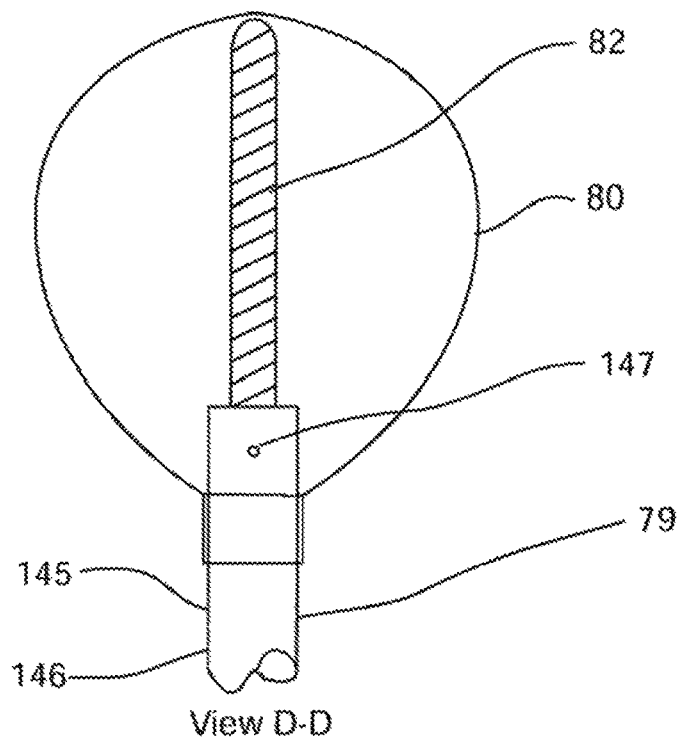
FIG. 6D is a view that is 90 degrees from the first side view of FIG. 6B.

FIG. 6A is a schematic illustration of a side view of the distal end of alternate embodiment of surgical probe 79 comprising expandable membranous structure 80 encompassing spring-like structure 82. Spring-like structure 82 is configured as a loop structure as depicted. Expandable membranous structure 80 is depicted in its un-expanded state. FIG. 68 is a schematic illustration of the same side view in FIG. 6A of alternate embodiment surgical probe 79 with its expandable membranous structure 80 in its expandable state. FIG. 6C is a schematic side view illustration taken at view C-C from FIG. 6A. FIG. 6D is a schematic side view illustration taken at view D-D from FIG. 6B. Surgical probe 79 is configured with expandable membranous structure 80 functioning as a liquid cryogen evaporation chamber as depicted in FIGS. 4A and 4B. Liquid cryogen enters the interior of expandable membranous structure 80 from encompassed spring-like structure 82. Evaporated cryogen gas exits the interior of expandable membranous structure 69 through fenestration(s) 147 in distal end 146 of probe shaft 145 and exits surgical probe 79 proximally into the room. Spring-like structure 82 is configured to pre-tension expandable membranous structure 80 in one radial axis to a greater extent than a second radial axis in a manner that causes expansion to be constrained in the radial axis with greatest pre-tensioning. In FIGS. 6A and 6B, spring-like structure 82 is configured to pre-tension membranous structure 80 to a greater extent in the radial axis that is normal to the view axis. In FIGS. 6C and 6D, spring-like structure 82 is configured to pre-tension expandable membranous structure 80 to a greater extent in the radial axis that is parallel to the view axis. FIG. 6A and FIG. 6C depict surgical probe 79 with expandable membranous structure 80 in its un-expanded state. FIGS. 6B and 6D depict surgical probe 79 with expandable membranous structure 80 in its expanded state. Pre-tensioning of expandable membranous structure 80 provides a means for achieving a predetermined expanded shape for optimal matching of the morphology of the target area of the lateral nasal wall.

Figure 6E:
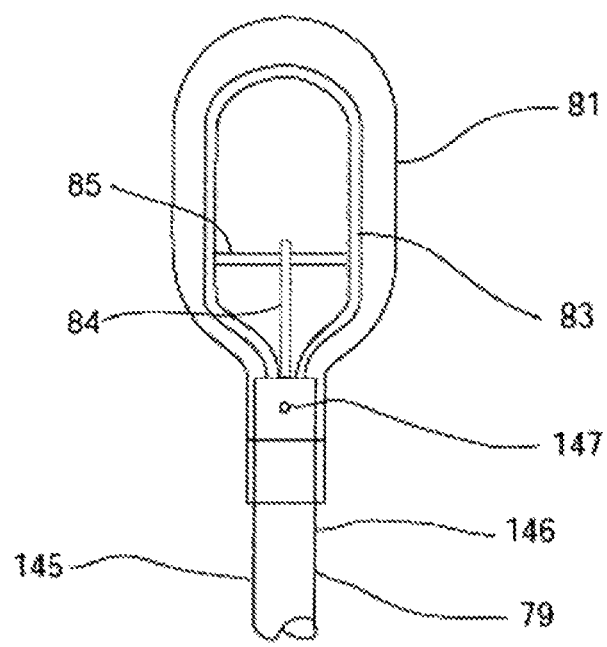
FIG. 6E is a view of the distal end of a surgical probe shaft with the structure comprising a continuous member encompassed by a non-distensible structure.

Another alternative embodiment is illustrated in the side view of FIG. 6E which shows a structure or member 83 which is formed into a looped and elongated structure having arcuate edges for presenting, an atraumatic surface. Rather than being formed as a spring like structure, the structure 83 may be formed of a relatively rigid wire or member instead which maintains its configuration when pressed against a tissue surface. Structure 83 may form a continuous structure which defines an opening there through such as a looped or elongated and looped member which is open through the loop. The structure 83 may be contained entirely within the expandable structure 81 which may be formed to have a predefined shape which is distensible or non-distensible when inflated by the cryogen. Moreover, the expandable structure 81 may be formed to surround the structure 83 entirely without being supported by or attached to the structure 83 itself. Such a structure 83 may provide a configuration which presents a low-profile as the device is advanced into and through the nasal cavity and between the nasal turbinate tissues. Yet because of the relatively flattened shape and rigidity and integrity of the structure 83, the structure 83 may be used to manipulate, move, or otherwise part the tissues of the nasal cavity without having to rely upon the expandable structure 81. Additionally, the low-profile enables the structure 83 to be positioned desirably within the narrowed confines of e.g., the cul-de-sac in proximity to the posterior nasal nerves (as shown by cul-de-sac 13 shown in FIG. 1). When the expandable structure 81 is in its deflated state, it may form a flattened shape and when inflated, the expandable structure 81 may inflate into a configuration which remains unsupported by or attached to the structure 83. Because the structure 83 may be formed of a member which solid along its length, the cryogen may be introduced directly into the expandable structure 81 through a distal opening defined in the probe shaft 145.

Alternatively, structure 83 may be formed of a hollow tubular member which itself is formed into the continuous or looped shape. In such an embodiment, the cryogen may be optionally introduced through the hollow tubular member and dispersed within the interior of the expandable structure 81 through one or more openings which may be defined along the tubular member. In yet another alternative, the structure 83 may be formed into a flattened shape rather than a looped shape. In this configuration, the structure may be either solid or hollow such that that cryogen may be introduced through the structure and into the interior of the expandable structure 81 via one or more openings defined along the structure.

The structure 83 may extend and remain attached to the probe shaft 145, but the remainder of the structure 83 which extends within the expandable structure 81 may remain unattached or unconnected to any portion of the expandable structure 81. Hence, once the expandable structure 81 is inflated by the cryogen, the structure 83 may be adjusted in position or moved via manipulating the probe shaft 145 relative to the interior of the expandable structure 81 to enable the targeted positioning and cooling of the tissue region when in contact against the outer surface of the expandable structure 81. For instance, the structure 83 may press laterally upon a particular region of the underlying tissue to stretch or thin out the contacted tissue region to facilitate the cryogenic treatment. When the structure 83 is adjusted in position relative to the expandable structure 81, the expandable structure 81 may remain in a static position against a contacted tissue region allowing for limited repositioning of the structure 83 within.

Alternatively in other variations, the structure 83 may be attached along the interior of the expandable structure 81 partially at particular portions of the structure 83 or along the entirety of the structure 83. For instance, structure 83 may be attached, adhered, or otherwise coupled over its entirety to expandable structure 81 while in other variations, a distal portion of structure 83 may be attached, adhered, or otherwise coupled to a distal portion of the expandable structure 81 while in yet other variations, portions of the structure 83 may be attached, adhered, or otherwise coupled to the expandable structure 81 along its side portions. Any of these variations may be optionally utilized depending upon the desired interaction and treatment between the structure 83, expandable structure 81, and underlying tissue region to be treated.

In yet another alternative variation, the lumen 84 for introducing the cryogen into the interior of the expandable structure 81 may be extended past the distal end of the probe shaft such that the cryogen is released, within the interior at a more distal location. As shown, the cryogen lumen 84 may be supported along the structure 83, e.g., via a bar or member 85 which extends across the structure 83. This particular variation may allow for the cryogen to be introduced into the distal portion of the interior of the expandable member 81. Either this variation or the variation where the cryogen is released from an opening of the probe shaft may be utilized as desired.

Figure 6F:
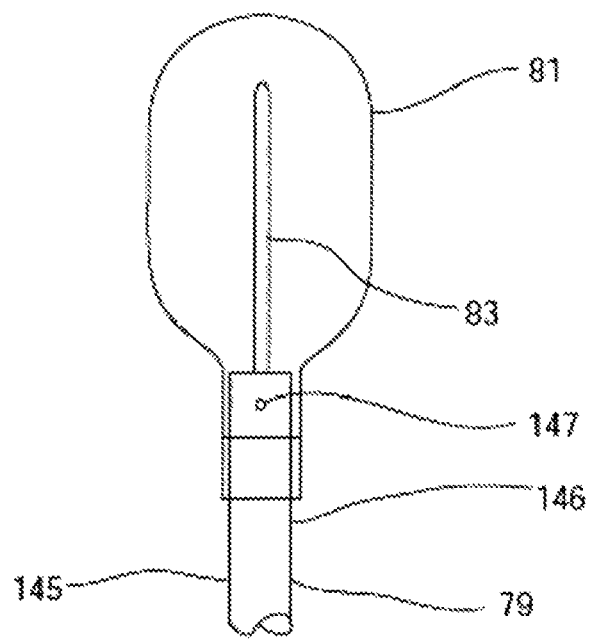
FIG. 6F is a view that is 90 degrees from the first side view of FIG. 6E.
Figure 6G:
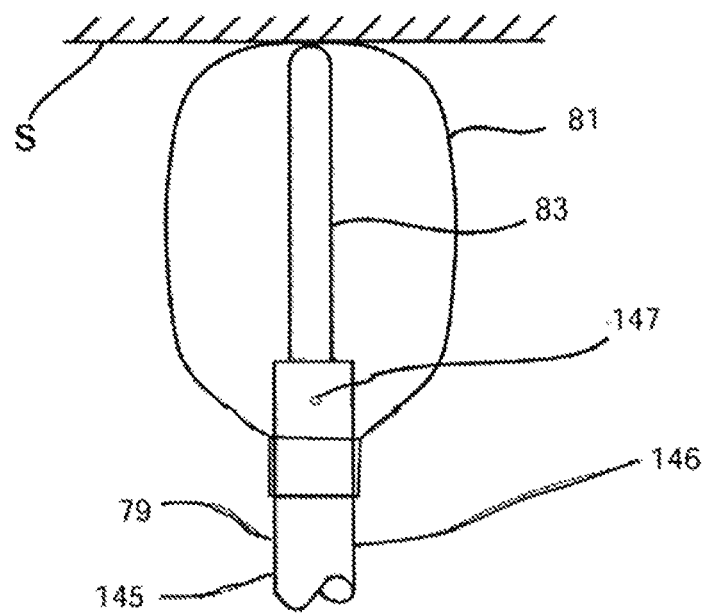
FIG. 6G is a view of the embodiment of FIG. 6E when pressed longitudinally against a tissue region for treatment.
Figure 6H:
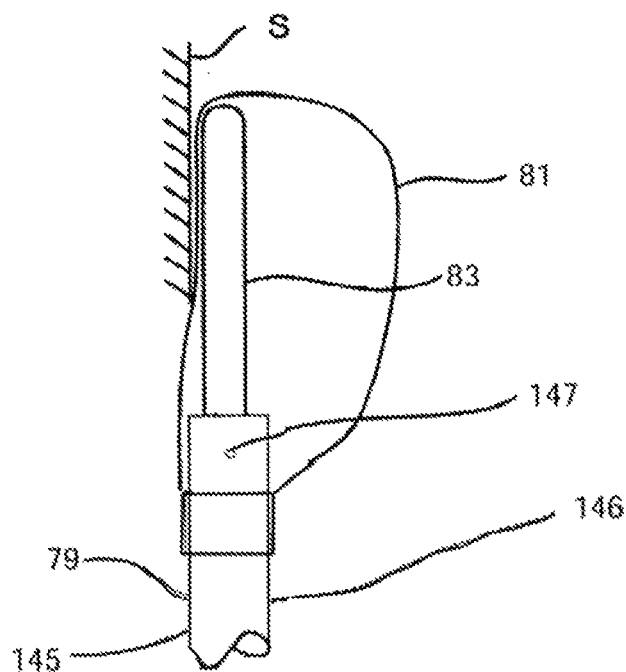
FIG. 6H is a view of the embodiment of FIG. 6E when pressed laterally against a tissue region for treatment.

FIG. 6F shows a side view of the embodiment of FIG. 6E illustrating how the structure 83 can be formed from a relatively flattened configuration relative to the inflated expandable structure 81. Because of the structural integrity of structure 83 and its relatively flattened profile, the structure 83 may provide for targeted treatment of the tissue when contacted by the device. FIG. 6G shows the side view of the inflated expandable structure 81 when pressed in a longitudinal direction by its distal tip against the underlying tissue surface S. The relative strength of the structure 83 provides for the ability to press the device against the tissue surface such that the remainder of the expandable structure 81 may maintain its inflated configuration to potentially insulate the other surrounding tissue regions. FIG. 6H likewise shows the device when the structure 83 is pressed laterally along its side against the tissue surface S such that the structure 83 lies flat. The contacted tissue region may be treated while the remainder of the surrounding tissue is potentially insulated by the expanded structure 81.

While the treatment end effector is designed for application along the tissue region defined by the cul-de-sac, the same end effector may be used in other regions of the nasal cavity as well. For instance, once the ablation is performed along the cul-de-sac, the end effector may then be moved to an adjacent tissue region, e.g., region immediately inferior to the cul-de-sac, and ablation treatment may be effected again. Additionally and/or alternatively, the end effector may also be used to further treat additional tissue regions, e.g., posterior aspect of the superior, middle, and/or inferior turbinates (any one, two, or all three regions). In either case, once the cul-de-sac has been ablated, the end effector may remain in place until the tissue region has thawed partially or completely before the end effector is moved to the adjacent tissue region for further treatment.

Once the treatment is completed, or during treatment itself, the tissue region may be assessed utilizing any number of mechanisms. For instance, the tissue region may be visually assessed utilizing an imager during and/or after ablation.

As described herein, the device may be utilized with a temperature sensor, e.g., thermistor, thermocouple, etc., which may be mounted along the shaft, within or along the expandable structure 81, along the structure 83, etc., to monitor the temperature not only of the cryogen but also a temperature of the tissue region as well under treatment.

Additionally and/or alternatively, the expandable structure 81 may also be vibrated while maintaining the structure 83 against the interior of the expandable structure 81 and the tissue region utilizing any number of vibrational actuators which may be mounted anywhere along the device as appropriate. The vibrations may be applied directly against the tissue region or, e.g., through a layer of gel to facilitate the vibrational contact with the tissue.

Additionally and/or alternatively, other biocompatible agents may be used in combination with the cryogenic treatment. For instance, in one variation, an anesthetic may be applied to the tissue region to be treated prior to or during the cryogenic treatment. This and other alternative features described may be utilized, not only with the variation shown and described in FIGS. 6E and 6F but with any other embodiments described herein.

Figure 7:
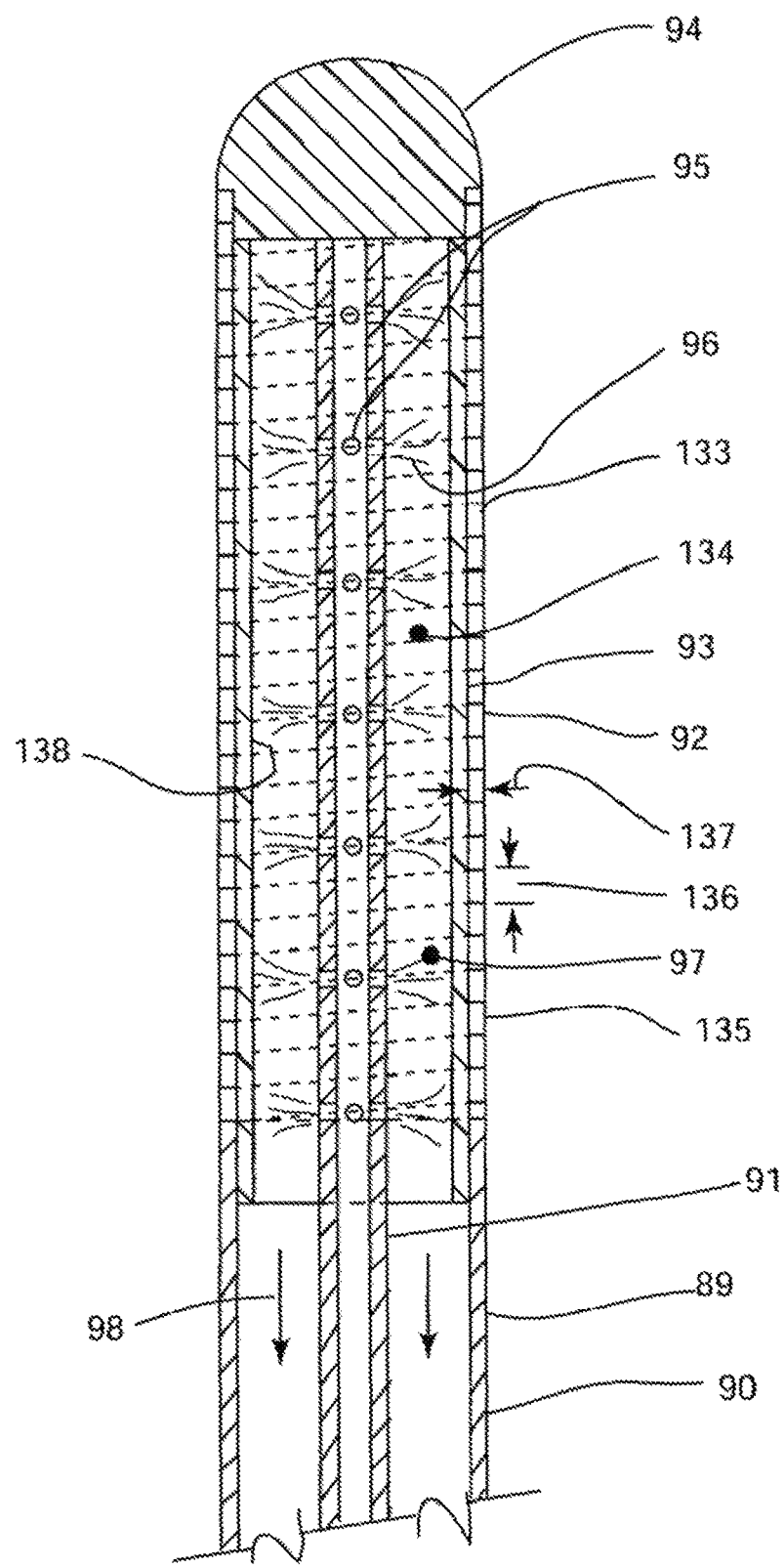
FIG. 7 is a cross sectional schematic view of the distal end of a surgical probe where the spring-like structure is configured as a closed cryogenic liquid evaporator.

FIG. 7 is a cross sectional schematic illustration of the distal end of a generic surgical probe 89, which represents the construction and functionality of previously described surgical probe end effectors described above. Depicted is the distal end of probe shaft 90, liquid cryogen supply line 91, wire coil 92, inner liner 93, end cap 94, metering orifices 95, liquid cryogen 96, liquid cryogen evaporation chamber 97, and cryogen exhaust path 98. Liquid cryogen evaporation chamber is defined by central channel 134 and inner liner 93 of wire coil 92, end cap 94 at its distal end, probe shaft 90 at its proximal end. Wire coil 92 may be welded to end cap 94 and probe shaft 90 as shown. Alternatively, adhesive may be used for assembly. Probe shaft 90 may be formed from a surgical grade stainless steel hypodermic tube with an outside diameter between: e.g., approximately 1 mm and 4 mm. Wire coil 92 comprises a tightly coiled flat wire with a coil pitch that approximates the axial thickness 136 of wire 135 as shown. Wire 135 may be a stainless steel wire, or may alternatively be a nickel titanium super elastic alloy wire. Wire 135 has an axial thickness 136 between, e.g., approximately 0.5 mm and 1.5 mm: and a radial thickness 137 between, e.g., approximately 0.1 mm and 0.5 mm. Wire 135 may alternatively be a round wire with a diameter between, e.g., approximately 0.25 mm and 1.0 mm.

Inner liner 93 is depicted being disposed on the inner wall of wire coil 92. Inner liner 93 is configured to provide a fluid tight seal of wire coil 92. Inner liner 93 may be a polymeric material such as polyethylene, or PTFE. Alternatively a polymeric line may be disposed on the outer surface 133 to provide a fluid tight seal of wire coil 92. Cryogen supply line 91 in fluidic communication with the supply of liquid cryogen in the liquid cryogen reservoir and liquid cryogen flow control valve in the surgical hand piece, not shown. Cryogen supply line 91 may be made from a thin walled tube with a high pressure rating, such as a polyimide tube. Cryogen supply line 91 delivers liquid cryogen 96 into liquid cryogen evaporation chamber 97 through metering orifice(s) 95. Liquid cryogen supply line 91 has an inner diameter between, e.g., approximately 0.2 mm and 0.8 mm, and a wall thickness between, e.g.: approximately 0.05 mm and 0.5 mm.

Metering orifices 95 are configured to comprise a distribution of fenestrations in the distal end of liquid cryogen supply line 91 as shown, and are configured to distribute liquid cryogen 96 into liquid cryogen evaporation chamber 97 in a substantially uniform manner. The diameter and number of metering orifices 95 are configured such that the flow of liquid cryogen 96 into liquid cryogen evaporation chamber 97 is sufficient to lower the temperature of outer surface 133 to between, e.g., approximately −20 Deg. C., and −50 Deg. C. during liquid cryogen evaporation in order to effect a cryo-ablation, while limiting the flow of liquid cryogen 96 into liquid cryogen evaporation chamber 97 so that substantially all liquid cryogen evaporates within liquid cryogen evaporation chamber 97. As depicted, liquid cryogen evaporation chamber 97 is an empty space. Alternatively, liquid cryogen evaporation chamber 97 may comprise a porous material configured to absorb the liquid cryogen 96 and prevent the liquid cryogen from leaving liquid cryogen evaporation chamber 97 while in a liquid state. Cryogenic gas leaves liquid cryogen evaporation chamber 97 through central channel 139, and is vented into the room.

Figure 8:
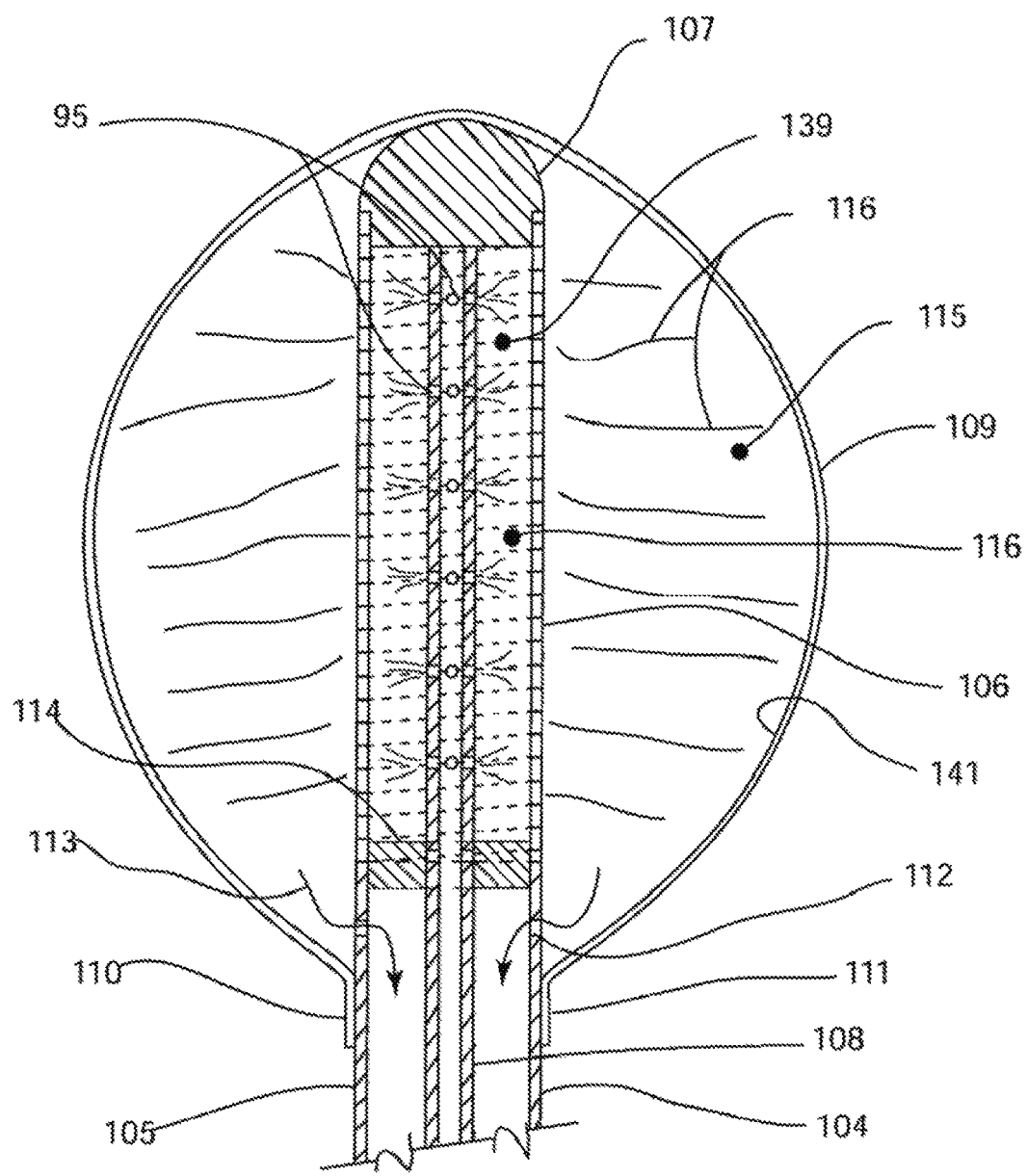
FIG. 8 is a cross sectional schematic view of the distal end of a surgical probe where the spring-like structure is encompassed by an expandable membranous structure with the membranous structure configured as a liquid cryogen evaporation chamber.

FIG. 8 is a cross sectional schematic illustration of the distal end of generic surgical probe 104 representing the construction and functionality of surgical probe embodiments 55, 68, and 79 previously described and depicted in FIGS. 4A and 48, FIGS. 5A through 5D, and FIGS. 6A through 6D, respectively. Depicted is the distal end of probe shaft 105, wire coil structure 106, end cap 107, liquid cryogen supply line 108, expandable membranous structure 109, in its expanded state, ostium 110, adhesive bond 111 between ostium 110 and probe shaft 105, cryogen gas exhaust vent 112, exhaust was flow path 113, pressure bulkhead 114, liquid cryogen evaporation chamber 115, and liquid cryogen 116. Wire coil 106, probe shaft 105, end cap 107, and cryogen supply line 108 are substantially similar to corresponding elements described in detail and depicted in FIG. 7, therefore, no further description is warranted. Expandable membranous structure 109, ostium 110, adhesive bond 111, cryogen gas exhaust vent 112, and exhaust gas flow path 113 are substantially similar to corresponding elements described in detail and depicted in FIGS. 4A, 4B, 5A through 5D, and 6A through 6D, therefore no further description is warranted. Liquid cryogen chamber 139 is defined by spring coil 106, end cap 107, and pressure bulkhead 114. Liquid cryogen 116 enters liquid, cryogen chamber 139 through liquid cryogen supply line 108, and through liquid cryogen ports 137. Wire coil 106 is configured to meter liquid cryogen 116 from liquid cryogen chamber 139 into liquid cryogen evaporation chamber 115 in a manner that sprays liquid cryogen 116 in the direction of interior surface 141 of expandable membranous structure 109 so that the liquid cryogen rapidly evaporates upon contact with inner surface 141. A perforated polymeric liner, not shown, disposed upon wire coil 106 may be used to provide proper metering and spatial distribution of liquid cryogen 116.

Figure 9:
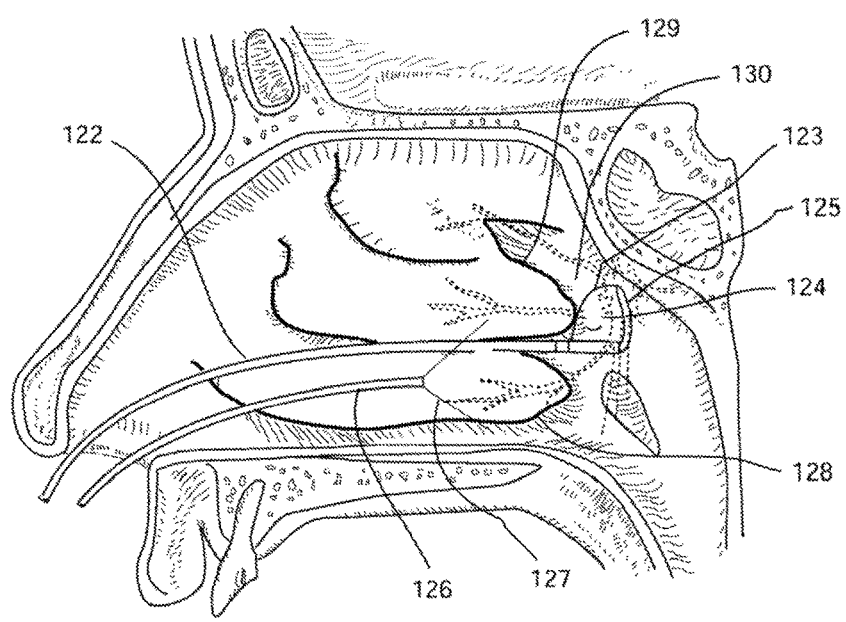
FIG. 9 is an internal lateral view of the nasal canal showing a surgical probe with the spring-like structure pressed against a lateral nasal wall in position for a cryo-ablation of a posterior nasal nerve function.
Figures 10A, 10B:
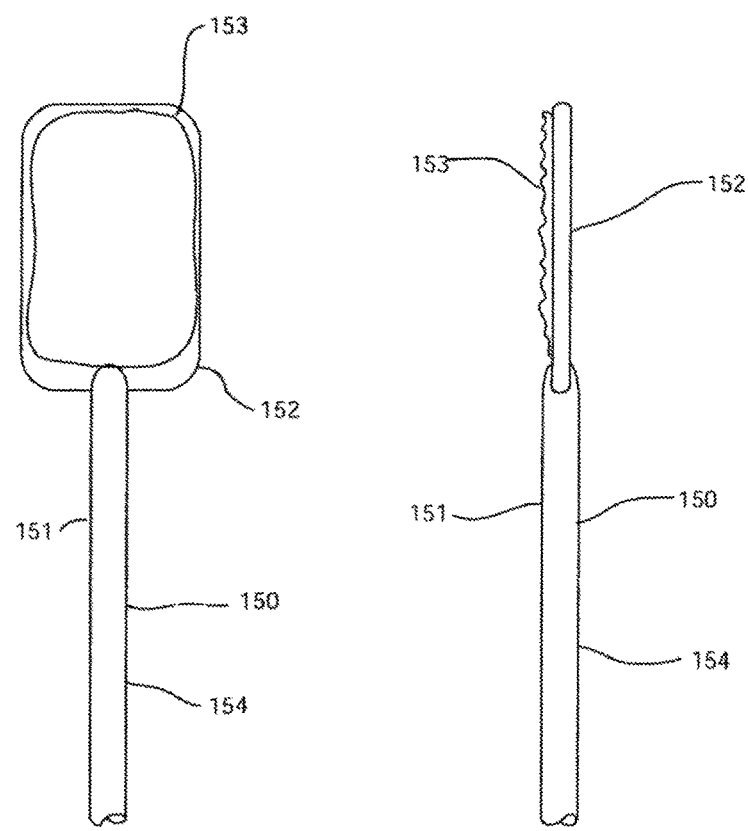
FIG. 10A is a front view illustration the distal end of a paddle balloon ablation probe with its expandable structure in its un-expanded state.
FIG. 10B is a side view illustration of FIG. 10A.
Figures 10C, 10D:
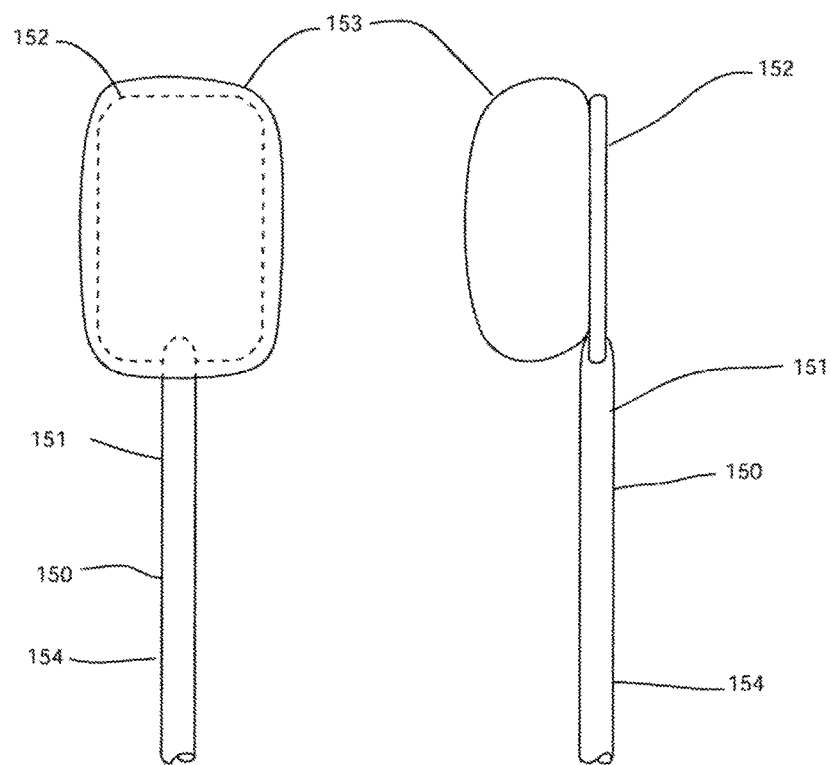
FIG. 10C is a front view illustration of the distal end of a paddle balloon ablation probe with its expandable structure in its expanded state.
FIG. 10D is a side view illustration of FIG. 10C.

FIG. 9 is an internal view of the nasal cavity showing surgical probe 148 comprising an expandable membranous structure 123, configured as a liquid cryogen evaporator in position for a cryo-ablation of at least one posterior nasal nerve associated with middle nasal turbinate 129, or inferior nasal turbinate 128. Probe shaft 122 is associated with a surgical hand piece, not shown. Endoscope 126, proximal end not shown, with field of view 127 is positioned to guide the correct surgical placement of spring-like structure 125, and expandable membranous structure 123 against lateral nasal wall 130 at region 124 posterior to the middle turbinate as shown. Expandable membranous structure 123 is depicted in an expanded state. Alternatively, an endoscopic imaging means may be incorporated into the surgical probe 148, along its shaft, which may comprise a CCD or CMOS imager FIGS. 10A thru 10D are schematic illustrations of the distal end 151 of alternative embodiment paddle balloon probe 150. Depicted is probe shaft 154, expandable structure 153, and paddle structure 152. FIG. 10A is a front view illustration of distal end 151 with expandable structure 153 in an un-expanded state. Expandable structure 153 is maintained in its un-expanded state during introduction to, and removal from the target region of the nasal anatomy. Suction may be applied by a suction means to maintain expandable structure 153 in its un-expanded state. FIG. 10B is a side view illustration of the distal end 151 of paddle balloon probe 150 with expandable structure 153 in its un-expanded state. FIG. 10C is a front view illustration of the distal end 151 of paddle balloon probe 150 with expandable structure 153 in its expanded or inflated state. FIG. 10D is a side view illustration of the distal end of paddle balloon probe 150 with expandable structure 153 in its expanded or inflated state. Paddle 152 is configured for access to middle meatus of the lateral nasal wall by means of insertion between the middle nasal turbinate and the inferior nasal turbinate, as illustrated in FIGS. 13A thru 13D below. Paddle structure 152 is a rounded rectangular shape as shown with a major dimension between approximately, e.g., 8 mm and 16 mm, and a minor dimension between approximately, e.g. 4 mm and 10 mm. The thickness of paddle structure 152 is between approximately, e.g. 1 mm and 3 mm. Paddle structure 152 is sufficiently rigid to access the middle meatus between the middle nasal turbinate and the inferior nasal turbinate, and is sufficiently flexible to avoid trauma to the nasal anatomy during use. Expandable structure 153 comprises a membrane that is bonded to paddle structure 152 in a manner that forms a air tight bladder as shown. Paddle balloon probe 150 is configured for introduction of a liquid cryogen into the bladder formed by paddle structure 152 and expandable structure 153, as well as to removed evaporated cryogen from the bladder with an exit to the room. The bladder formed by paddle structure 152 and expandable structure 153 is configured as cryogenic evaporation chamber, and the outer surface of expandable structure 153 is configured as a cryo-ablation surface. Expandable structure 153 is configured apply a force against the middle meatus of the lateral nasal wall between approximately, e.g. 20 grams and 200 grams. Expandable structure 153 is configured for expansion in reaction cryogen evaporation within. Liquid cryogen is introduced into the bladder through probe shaft 154, and evaporated cryogen gas is removed from the bladder and vented to the room trough probe shaft 154. The cryogenic ablation mechanisms and other features are similar to cryo-ablation probe embodiments described above and below.

Figures 11A, 11B:
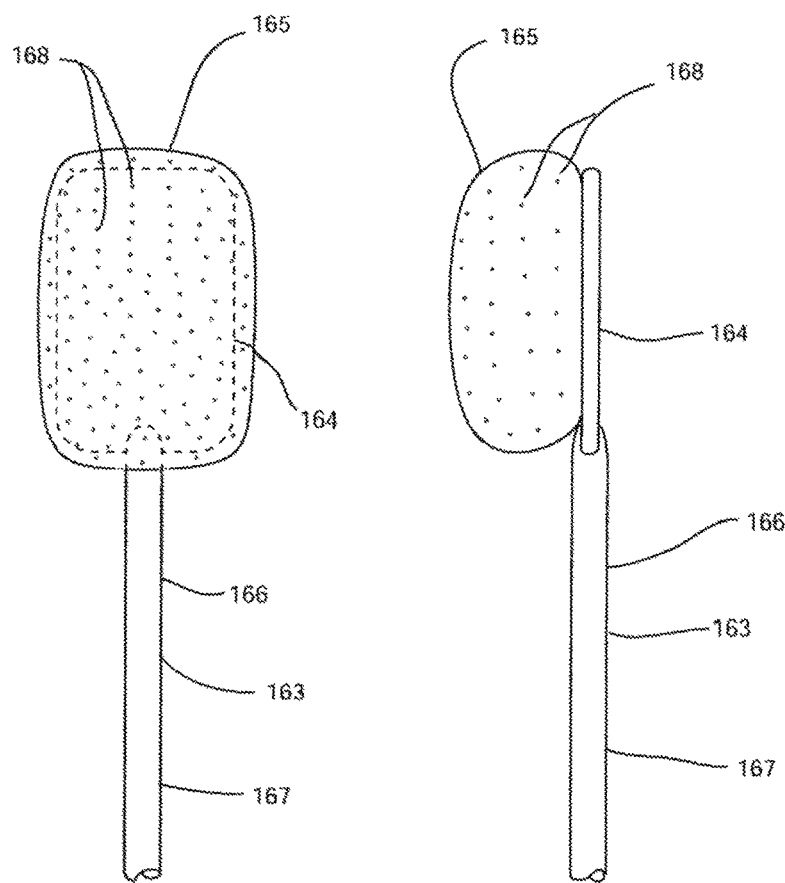
FIG. 11A is a front view illustration of the distal end of a paddle porous balloon ablation probe.
FIG. 11B is a side view illustration of FIG. 11A.

FIGS. 11A and 11B are schematic illustrations of the distal end 166 of paddle porous balloon probe 163, which is an alternative embodiment of paddle balloon probe 150. FIG. 11A is front view illustration, and FIG. 11B is a side view illustration. Paddle porous balloon probe 163 comprises probe shaft 167, porous expandable structure 165, and paddle structure 164. Porous expandable structure 165 is similar to expandable structure 153, described above, comprising a porous membrane versus an air tight membrane. Porous expandable structure 165 is configured for the venting of evaporated cryogen gas through the pores 168 from within the bladder formed by porous expandable structure 165 and paddle structure 164 into the patient's nostril in the immediate vicinity of the surface of the lateral nasal wall that is targeted for cryo-ablation. Venting the cold gas in the vicinity of the targeted lateral nasal wall enhances cooling effectiveness, while precluding the need to vent the evaporated cryogen gas through probe shaft 167, allowing the probe shaft to be smaller in caliber, and therefore less traumatic. The cryogenic ablation mechanisms and other features are similar to cryo-ablation probe embodiments described above and below.

Figures 12A, 12B:
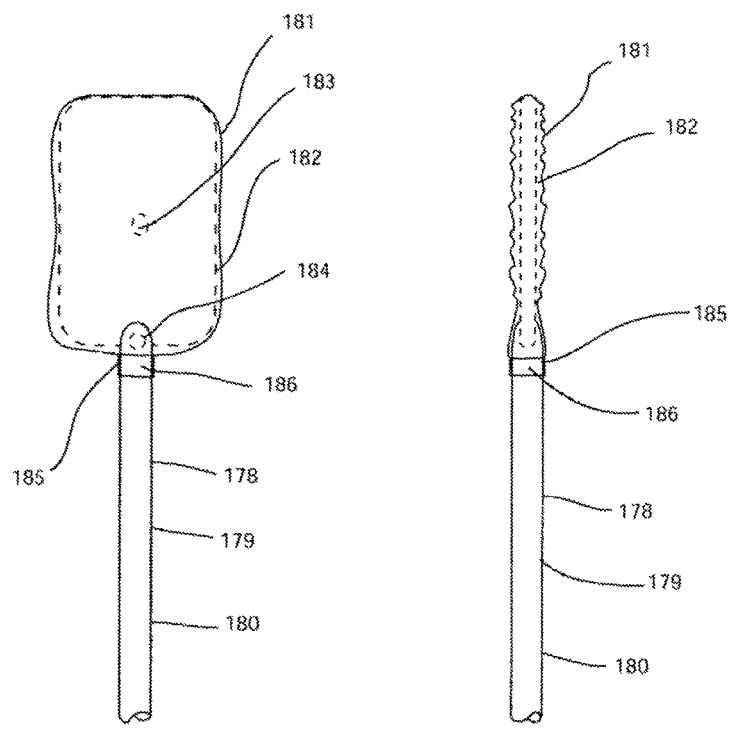
FIG. 12A is a front view illustration the distal end of a paddle double balloon ablation probe with its expandable structure in its un-expanded state.
FIG. 12B is a side view illustration of FIG. 12A.
Figures 12C, 12D:
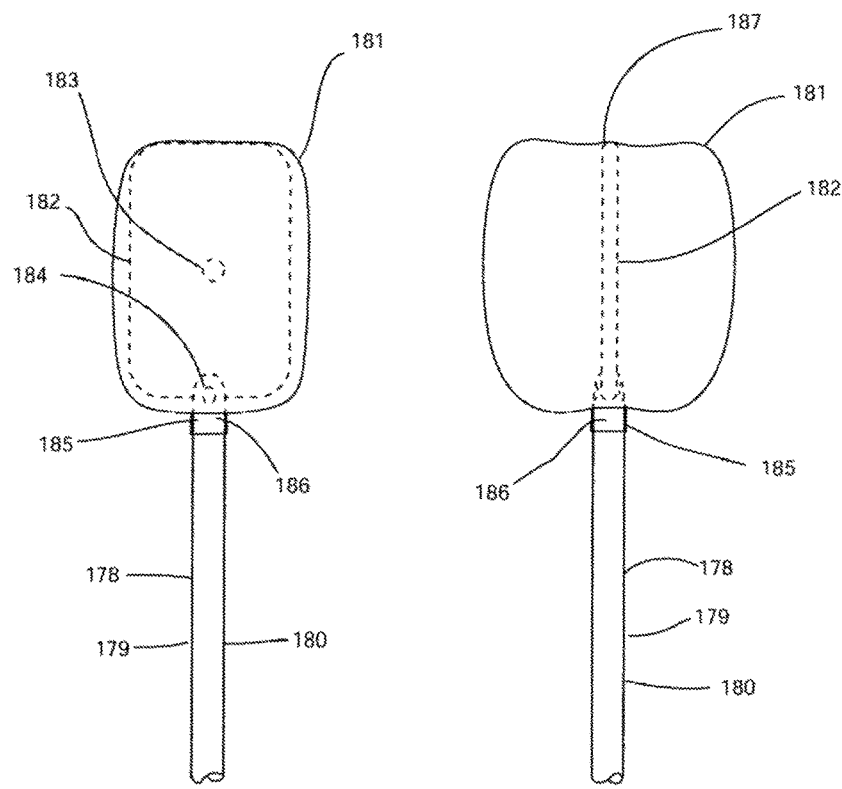
FIG. 12C is a front view illustration of the distal end of a paddle double balloon ablation probe with its expandable structure in its expanded state.
FIG. 12D is a side view illustration of FIG. 12C.

FIGS. 12A thru 12D are schematic illustrations of the distal end 179 of double balloon paddle probe 178. FIG. 12A is a front view illustration of double balloon paddle probe 178 with expandable structure 181 in its un-expanded state. FIG. 12B is a side view illustration of double balloon paddle probe 178 with expandable structure in its un-expanded state. FIG. 12C is a front view illustration of double balloon paddle probe 178 with expandable structure 181 in its expanded state. FIG. 12D is a side view illustration of double balloon paddle probe 178 with its expandable structure 181 in its expanded state. Double balloon paddle probe 178 comprises probe shaft 180, expandable structure 181, paddle structure 182, liquid cryogen port 183, and cryogen gas exhaust port 184. In this embodiment, expandable structure 181 encompasses paddle structure 182 and comprises a single ostium 185, and an adhesive bond 186 which forms an air tight seal of for expandable structure 181. The configuration and function of this embodiment substantially similar to the embodiment depicted in FIGS. 6A to 6H, with the difference being in this embodiment a paddle structure 182 is encompassed by expandable structure 181, versus a spring-like structure or a formed wire structure encompassed by an expandable structure as depicted in FIGS. 6A to 6H. Optionally, the distal inner edge of paddle structure 182 and be bonded to the interior of expandable structure 181 by adhesive bond 187.

Figure 13A:
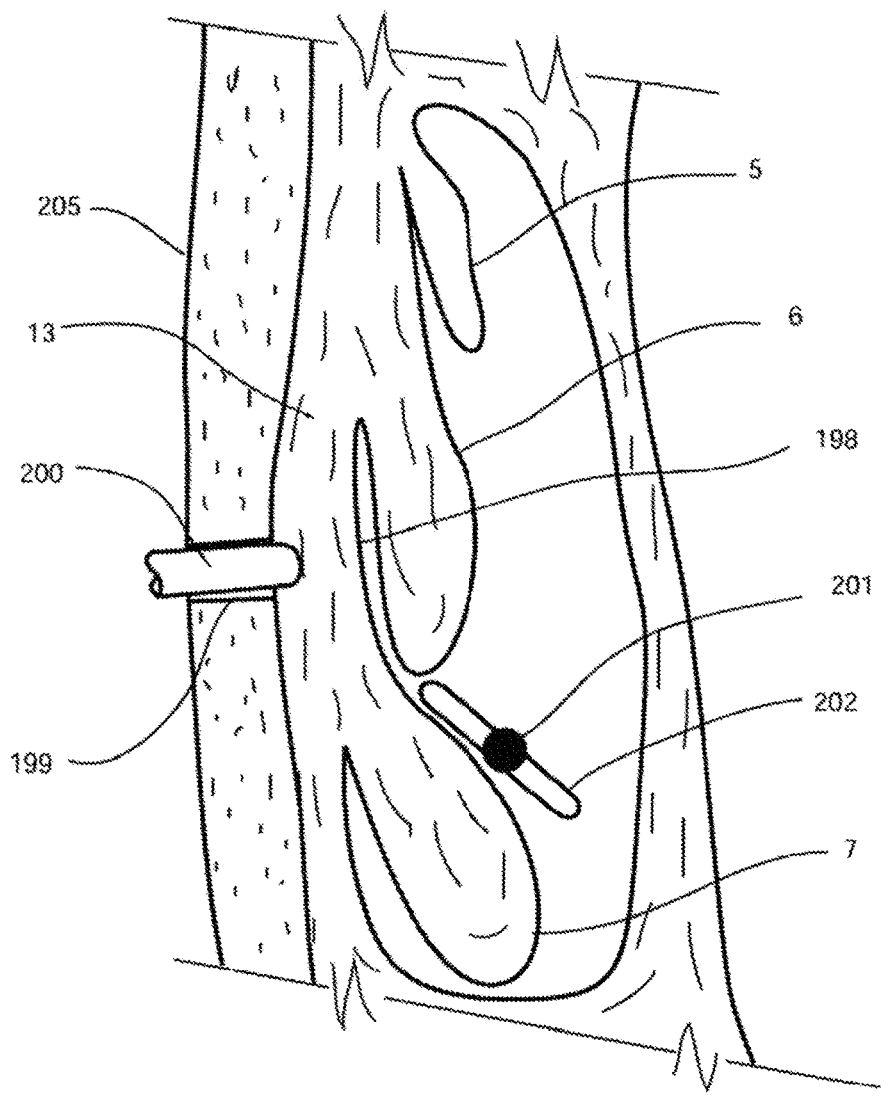
FIG. 13A through 13D are schematic sectional coronal illustrations of a nasal cavity depicting the surgical access to a middle meatus and cryogenic ablation of a sphenopalatine brand and foramen.
Figure 13B:
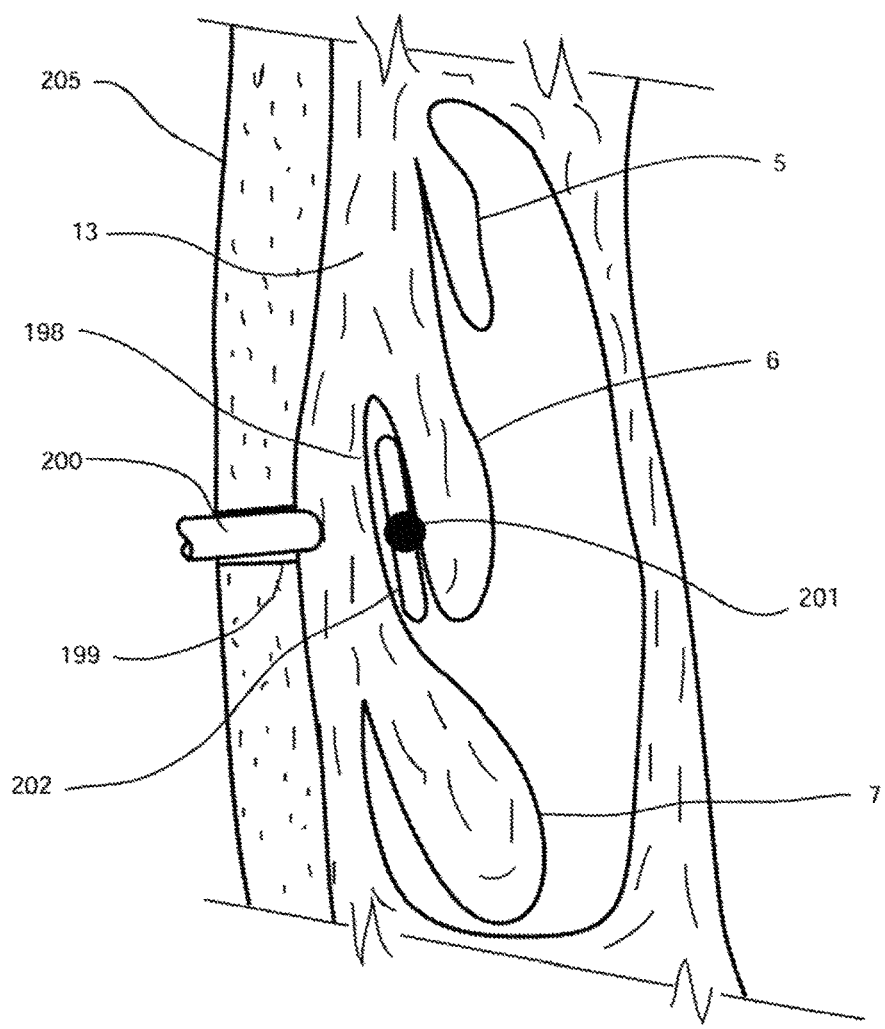
Figure 13C:
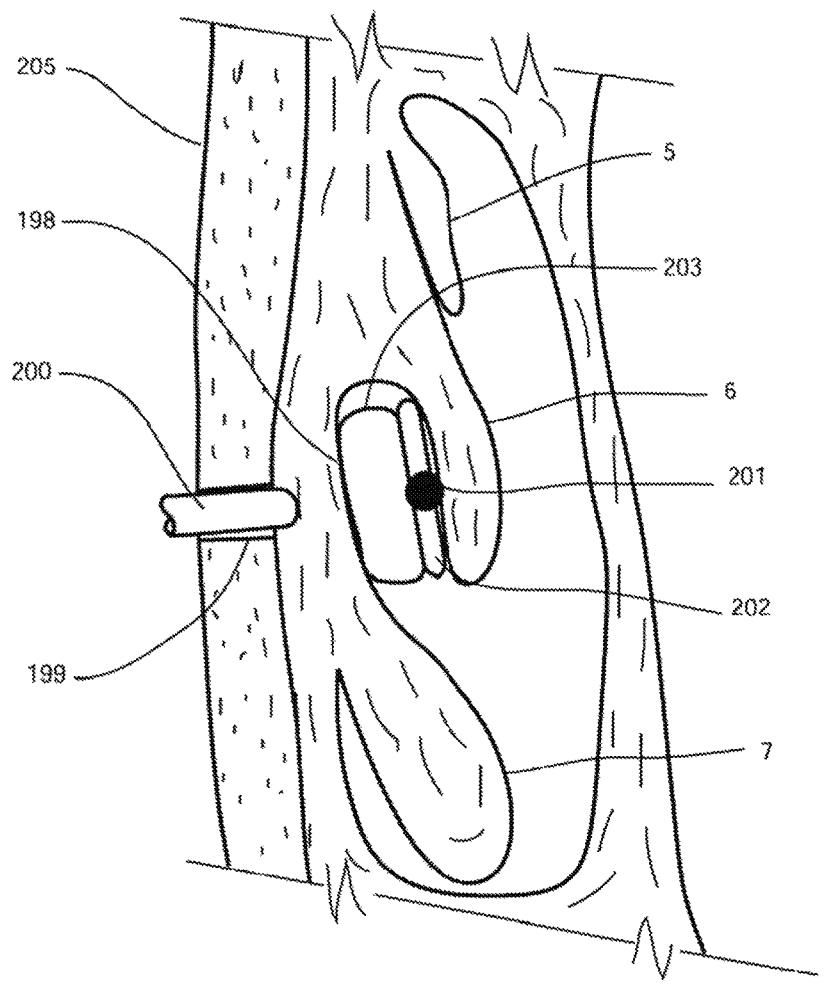
Figure 13D:
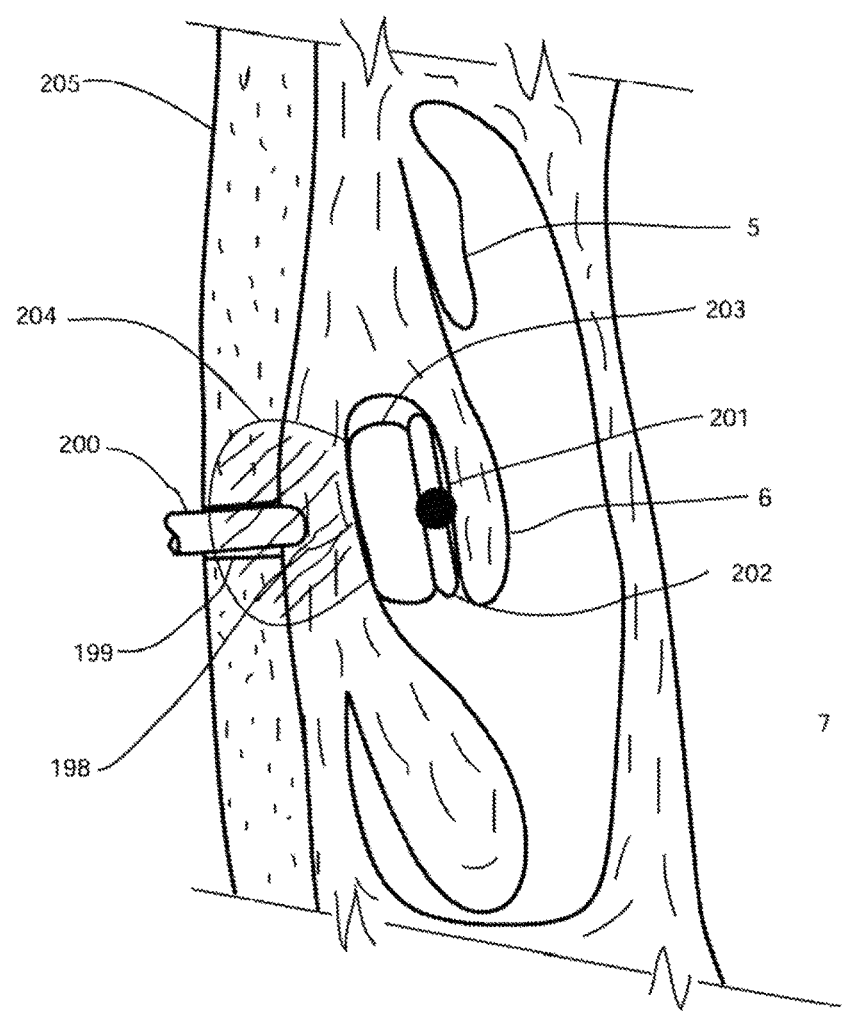

FIGS. 13A through 13D are schematic sectional coronal illustrations of the nasal cavity depicting ablation probe 201 access to the middle meatus 198 between the middle nasal turbinate 6 and inferior nasal turbinate 7. Ablation probe 201 is a generic representation any of the ablation probes disclosed here within that utilize and expandable structure. FIG. 13A depicts the thin edge of the distal end of ablation probe 201 being inserted into the thin gap between middle nasal turbinate 6 and inferior nasal turbinate 7. FIG. 13B depicts the distal structure of ablation probe 201 behind middle turbinate against the middle meatus 198 in position for an ablation. FIG. 13C depicts the initiation of ablation by activation of the flow of cryogenic liquid into the expandable structure 203 resulting in the inflation of the expandable structure 203 as shown. Please note, as depicted, the expandable structure is most similar to that depicted in FIGS. 10 and 11, but is not intended imply a preference for those embodiments over the other embodiments disclosed here within. FIG. 13D depicts the ablation zone 204 resulting from the application of a cryo-ablation of between approximately, e.g. 20 to 300 seconds. Following ablation, the probe may be removed following a thawing period that may be between approximately, e.g. 20 to 30 seconds. As depicted the sphenopalatine branch, comprising the sphenopalatine artery, sphenopalatine vein, and sphenopalatine nerve, and the sphenopalatine foramen are substantially encompassed by the zone of ablation 204. As previously described, and further described below, the targeted tissue may comprise other locations, including the proximity of accessory posterolateral nerves bounded by a sphenopalatine foramen superiorly, an inferior edge of an inferior turbinate inferiorly, a Eustachian tube posteriorly, or a posterior third of the middle and inferior turbinates anteriorly. Other anatomical targets may include the pterygomaxillary fossa, sphenopalatine ganglion, or vidian nerve.

Figure 14A:
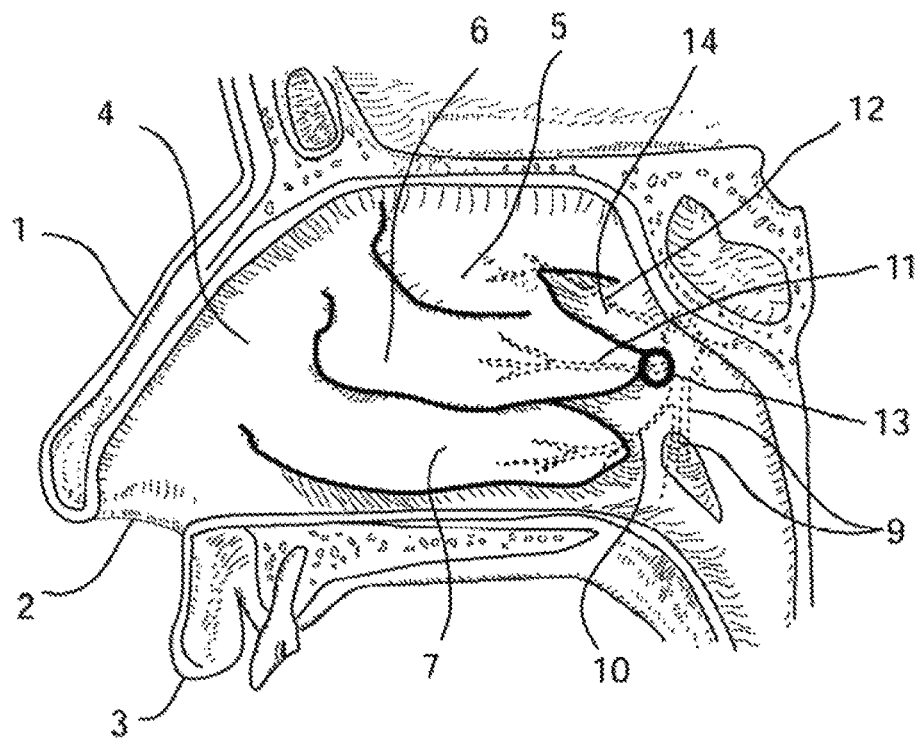
FIG. 14A is an internal lateral view of the nasal cavity showing an anatomical target for ablation of parasympathetic nervous function of the middle turbinate.
Figure 14B:
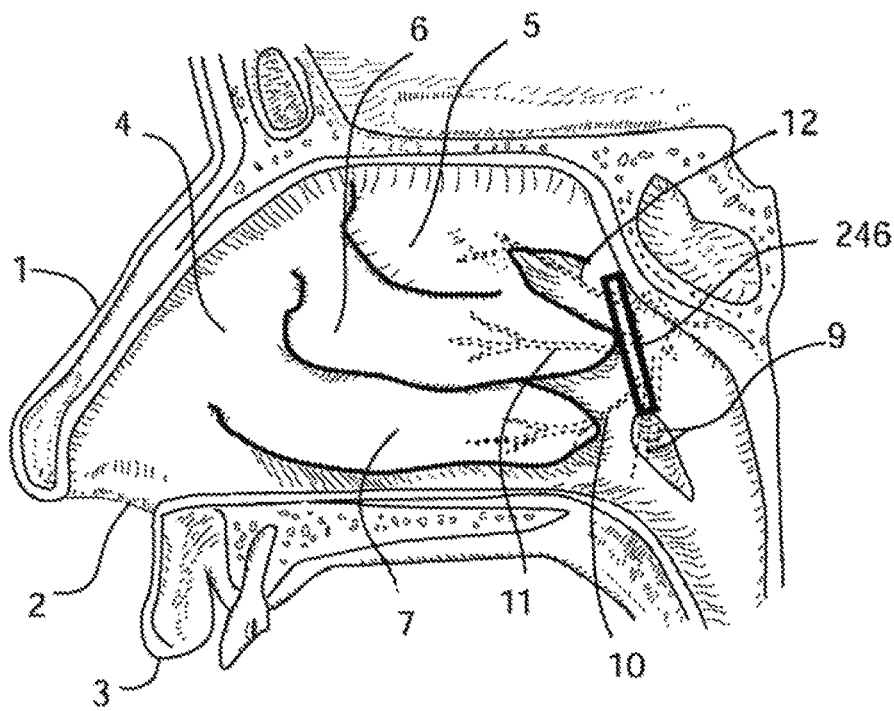
FIG. 14B is an internal lateral view of the nasal cavity showing, an anatomical target for ablation of posterior nasal nerves.
Figure 14C:
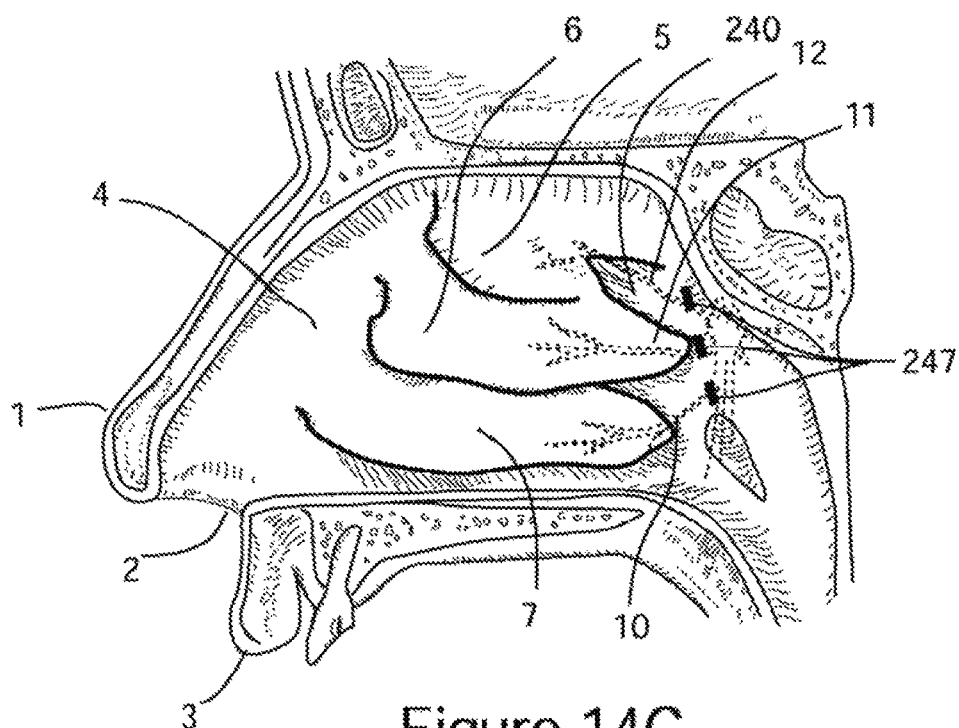
FIG. 14C is an internal lateral view of the nasal cavity showing an anatomical target for ablation of posterior nasal nerves using an intermittent line of ablation.

FIG. 14A is an internal lateral view of the nasal cavity showing target 228 for ablation of the parasympathetic nervous function of middle turbinate 6. Ablation target 228 is directly over the posterior superior lateral nasal branches 11 which innervate middle turbinate 6. Ablation target 228 may be circular as shown or non-circular, with a zone of ablative effect between 1 mm and 4 mm deep. FIG. 14B is an internal lateral view of the nasal cavity showing target 246 for ablation of parasympathetic nervous function of superior turbinate 5, middle turbinate 6, and inferior turbinate 7. Ablation target 246 is linier as shown and is directly over posterior inferior lateral nasal branch 10, which innervates inferior turbinate 7, posterior superior lateral nasal branch 11 which innervates middle turbinate 6, and superior lateral nasal branch 12 which innervates superior turbinate 5. The depth of ablative effect is ideally between 1 mm and 4 mm deep. FIG. 14C is an internal lateral view of the nasal cavity showing target 247 for ablation of parasympathetic nervous function of superior turbinate 5, middle turbinate 6, and inferior turbinate 7. Ablation target 246 is linier and segmented as shown with ablation segments directly over posterior inferior lateral nasal branch 10, which innervates inferior turbinate 7, posterior superior lateral nasal branch 11 which innervates middle turbinate 6, and superior lateral nasal branch 12 which innervates superior turbinate 5. The depth of ablative effect is ideally between 1 mm and 4 mm deep. FIG. 2D is an internal lateral view of the nasal cavity showing target 248 for ablation of the parasympathetic nervous function of middle turbinate 6. Ablation target 228 is directly over the posterior superior lateral nasal branches 11 which innervate middle turbinate 6. Ablation target 248 is oblong as shown and positioned between middle turbinate 6 and inferior turbinate 7 as shown, with a zone of ablative effect between 1 mm and 4 mm deep.

Figure 15A:
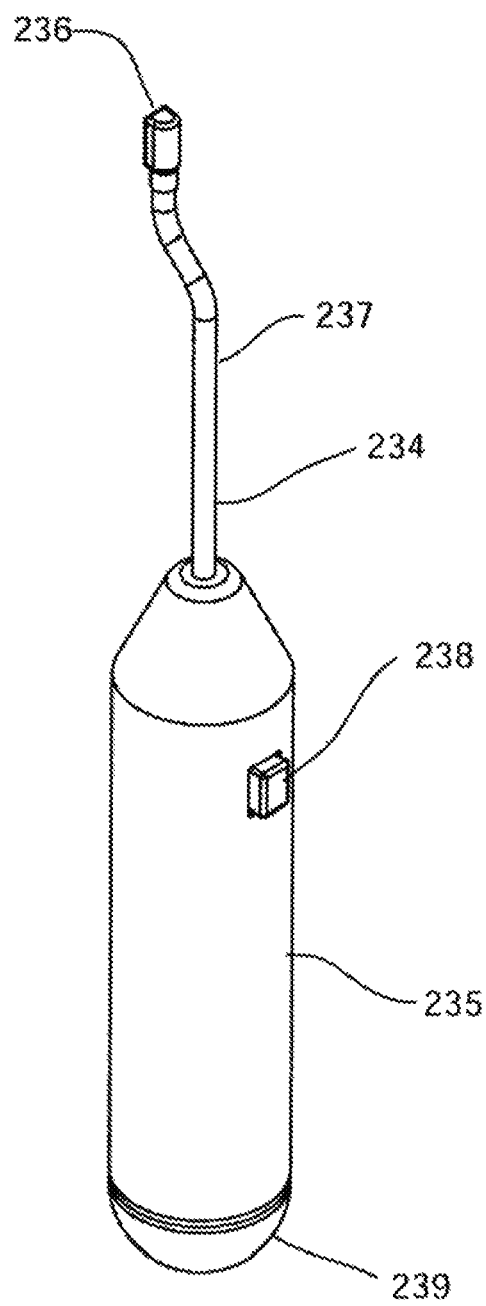
FIG. 15A is a schematic illustration of a cryosurgical probe configured for cryo-ablation of posterior nasal nerves comprising a spatula shaped cryosurgical tip.
Figure 15B:
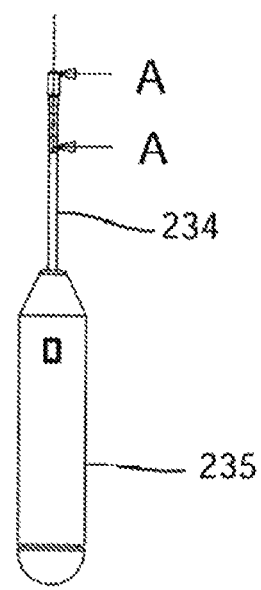
FIG. 15B defines a section view of the cryosurgical probe's cryosurgical tip.
Figure 15C:
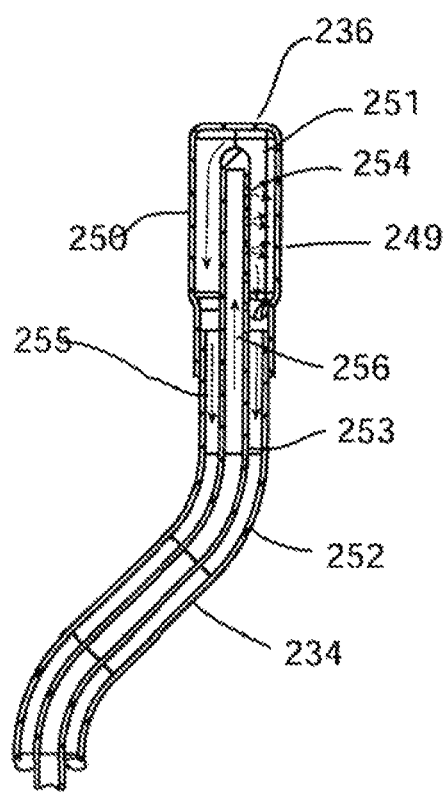
FIG. 15C is a cross sectional view of the cryosurgical probe's tip.

FIG. 15A is a schematic illustration of cryosurgical probe 234 configured for cryo-ablation of parasympathetic nervous function of a nasal turbinate(s) comprising a spatula shaped cryosurgical tip 236. Cryosurgical probe 234 comprises handle 235, probe shaft 237 cryosurgical tip 236 refrigerant cartridge cover 239, and refrigerant control push button 238. Handle 235 may comprise a receptacle, not shown, for receiving a refrigerant filled cartridge, not shown, which may comprise liquid carbon dioxide, which is used for evaporative cryogenic cooling within cryosurgical probe tip 236. Alternatively, the cartridge may comprise a compressed cryogenic gas which may comprise argon or nitrous oxide which is used for Joule-Thompson effect cryogenic cooling within cryosurgical probe tip 236. Those skilled in the art cryosurgical instrumentation are familiar with means for configuring cryosurgical probe 234 for evaporative cryogenic cooling or Joule-Thompson effect cryogenic cooling according to this invention, therefore, further detailed description relating to cryosurgical techniques are not warranted. Refrigerant control push button 238 is in mechanical communication with a valve which is configured to open when push button 238 is depressed by the operator causing the cryogen within the cartridge to flow into cryosurgical probe tip 236 through a conduit within probe shaft 237. Handle 235 further comprises a venting means, not shown for exhausting the expanded cryogen into the atmosphere. Probe shaft 237 is between approximately 2 mm and 6 mm in diameter, with a length between approximately 4 cm and 10 cm. FIG. 15B defines a section view of the cryosurgical probe 234 cryosurgical tip 236. FIG. 15C is a cross sectional view of the cryosurgical probe 234 distal end comprising probe shaft 237, refrigerant delivery tube 253, and probe tip 236. Cryogen delivery tube 253 traverses the length of probe shaft 237 in a coaxial relationship and is in fluidic communication with the cryogen cartridge in handle 235 through the cryogen control valve previously described. At the distal end of cryogen delivery tube 253 there is at least one lateral fenestration configured to direct the release of the pressurized cryogen 256 from cryogen delivery tube 253 into expansion chamber 251 of cryosurgical tip 236 in the direction of cryo-ablation surface 249 of cryosurgical tip 236. Cryo-ablation surface 249 is substantially flat. The opposing surface 250 to ablation surface 249 may be cylindrical as shown. By directing the release of cryogen towards ablation surface 249, ablation surface 249 achieves cryo-ablation temperatures between approximately −20 to −200 degrees centigrade, and opposing surface 250 remains warmer. The expanded cryogen 255 exits expansion chamber 251 through probe shaft 252 and is vented to atmosphere through handle 235 as previously described. Probe shaft 237, cryogen deliver tube 253, and cryosurgical tip 236 may fabricated from a stainless steel as is typical with cryosurgical probes, or may be fabricated with alternative materials as is familiar to those skilled in the art of cryosurgical probes. Probe shaft 237 may configured as shown with curvatures configured for nasal anatomy, or alternatively may be configured as described below.

Figure 16A:
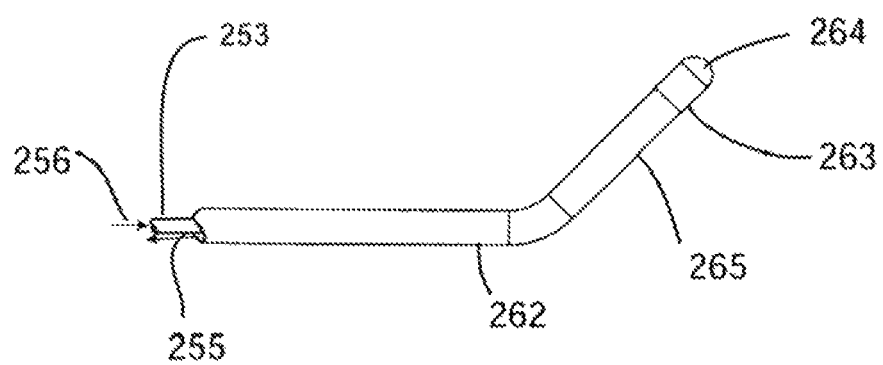
FIG. 16A and FIG. 16D are schematic illustration of the distal end of an alternative embodiment of the cryosurgical probe comprising a bullet shaped cryo-ablation element at the distal end of an angled shaft.
Figure 16B:
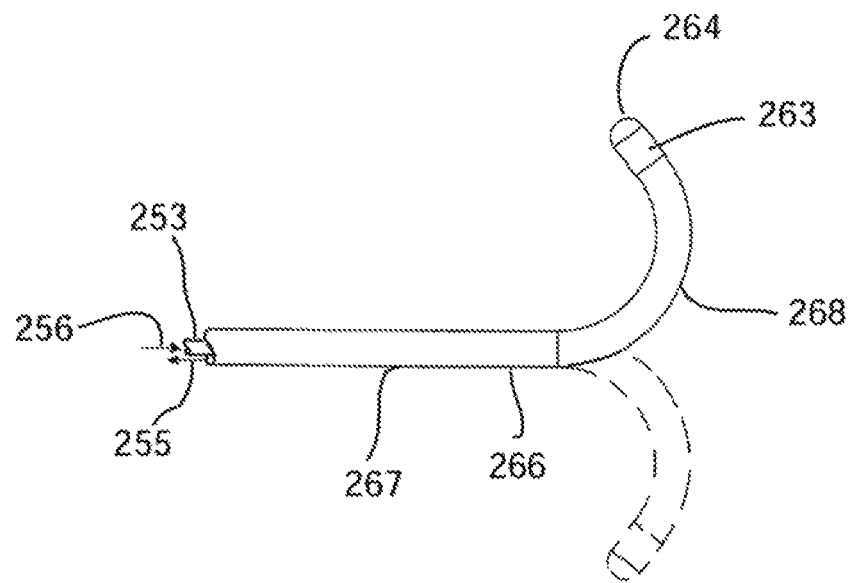
FIG. 16B is a schematic illustration of the distal end of an alternative embodiment of the cryosurgical probe comprising a bullet shaped cryo-ablation element at the distal end of a user deflectable probe shaft.
Figure 16C:
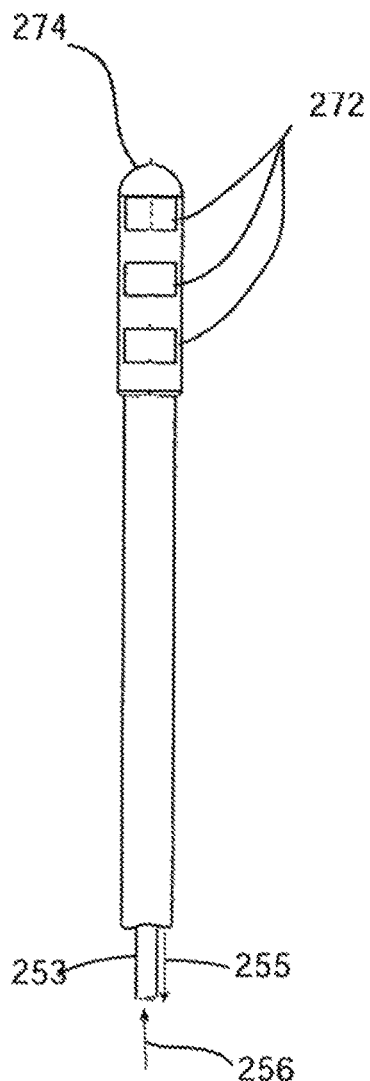
FIG. 16C is a schematic illustration of the distal end of an alternative embodiment of the cryosurgical probe where the cryo-ablation element is configured for producing multiple discrete cryo-ablations simultaneously.
Figure 16D:
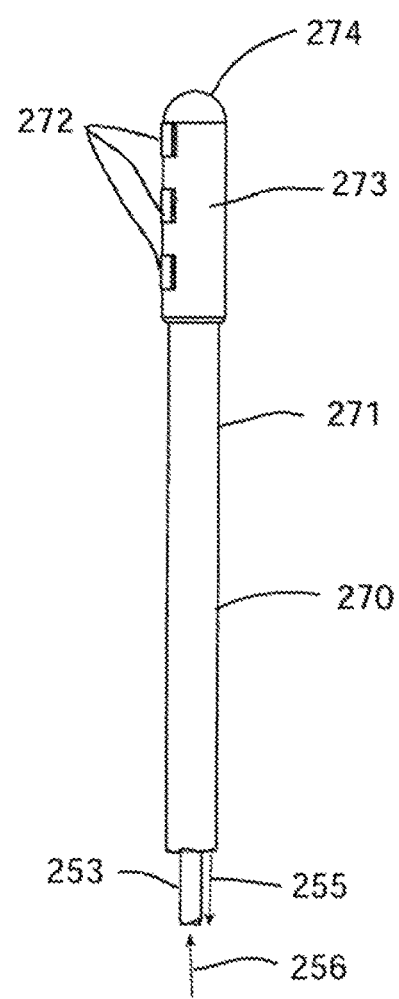

FIG. 16A is a schematic illustration of the distal end of an alternative embodiment 262 of the cryosurgical probe comprising a bullet shaped cryo-ablation element 263 at the distal end of angled probe shaft 265. In this embodiment pressurized cryogen is released through an orifice in an axial direction into the expansion chamber in the direction cryo-ablation surface 264. The diameter of shaft 265 is between approximately 2 mm and 6 mm, and the angle of shaft 265 is between approximately 30 and 60 degrees, and the point of bend is between 1 cm and 3 cm from the distal end of ablation element 263. FIG. 16B is a schematic illustration of the distal end of an alternative embodiment 266 of the cryosurgical probe comprising a bullet shaped cryo-ablation element 263 at the distal end of a user deflectable probe shaft 267. Deflectable probe shaft 267 comprises distal deflectable segment 268 and a substantially rigid non-deflectable proximal segment 269. Probe shaft 267 diameter is between approximately 2 mm and 6 mm. The border between deflectable distal segment 268 and proximal non-deflectable segment is between approximately 1 cm and 3 cm from the distal end of ablation element 263. The angle of deflection may be between approximately 60 to 120 degrees and may be configured for deflection in one direction, or in two directions as shown. The deflection means comprises at least one pull wire housed within probe shaft 267 and a deflection actuator disposed in the vicinity of the proximal end of probe 266. Those skilled in the art deflectable tipped surgical probes are familiar means for creating a deflectable tipped cryosurgical probe according to this invention. FIGS. 16C and 16D are schematic illustrations of the distal end of an alternative embodiment 270 of the cryosurgical probe where the cryo-ablation element 274 is configured for producing multiple discrete cryo-ablations simultaneously. Cryo ablation element 274 comprises an expansion chamber, not shown, discrete lateral cryo-ablation surfaces 272, surrounded by thermal insulation 273. Ablation element 274 comprises a hollow bullet shaped metallic structure with lateral protrusions in the surface forming cryo-ablation surfaces 272, with a thermal insulating material covering all remaining external surfaces of ablation element 274 as shown. As with cryo-surgical probe 234, cryogen is released from cryogen delivery tube in a lateral direction towards cryo-ablation surfaces 272.

Figure 17A:
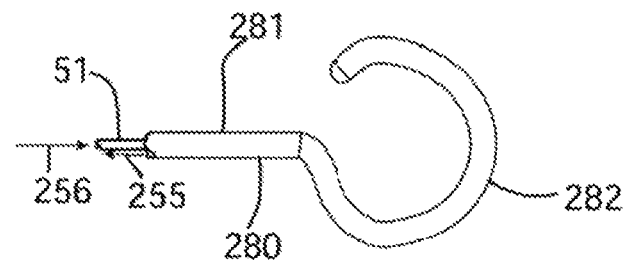
FIG. 17A is a schematic illustration of the distal end of an alternative embodiment of the cryosurgical probe comprising a semi-circular cryo-ablation element.
Figure 17B:
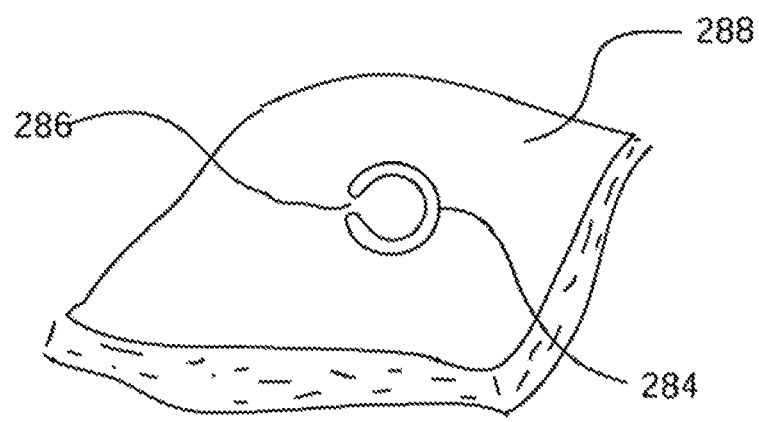
FIG. 17B is a schematic illustration of the ablation morphology resulting from use of the semi-circular cryo-ablation element.
Figure 17C:
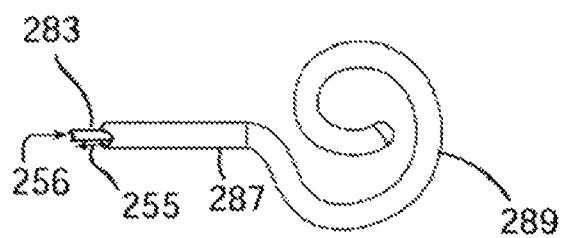
FIG. 17C is a schematic illustration of the distal end of art alternative embodiment of the cryosurgical probe comprising a spiraled cryo-ablation element.

FIG. 17A is a schematic illustration of the distal end of an alternative embodiment 280 of the cryosurgical probe comprising a semi-circular cryo-ablation element 282. Cryo-ablation element 282 comprises a continuation of probe shaft 281 formed in a semi-circle as shown. Within the semi-circular section cryogen delivery tube 283 comprises an array of lateral fenestration in the one axial direction relative to semi-circular form, making the corresponding surface of the ablation element 282 the cryo-ablation surface. FIG. 17B is a schematic illustration of the ablation 284 morphology in the nasal mucosa 288 resulting from use of the semi-circular ablation element 282. The gap 286 in the ablation provides blood perfusion to the mucosa encompassed by the ablation providing a reduction in tissue sloughing as the result of the ablation, as well as a reduction in the chance of infection, and a reduction of patient discomfort. FIG. 17C is a schematic illustration of the distal end of an alternative embodiment 287 of the cryosurgical probe comprising a spiraled cryo-ablation element.

Figure 18A:
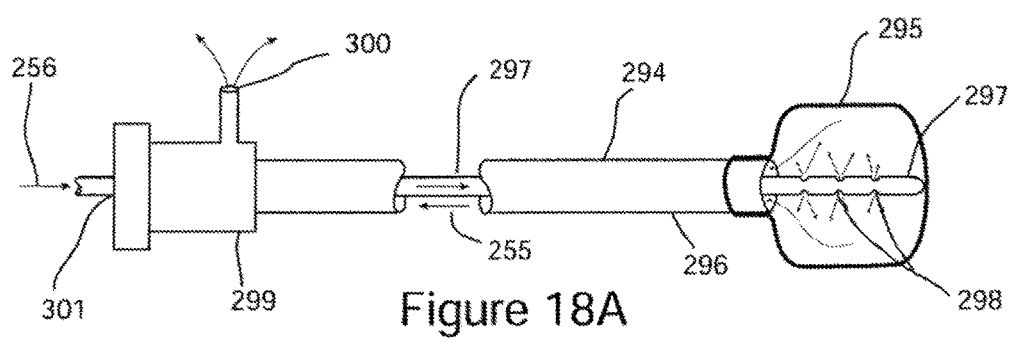
FIG. 18A is a schematic illustration of cryo-ablation balloon probe configured for cryo-ablation of posterior nasal nerves.
Figure 18B:
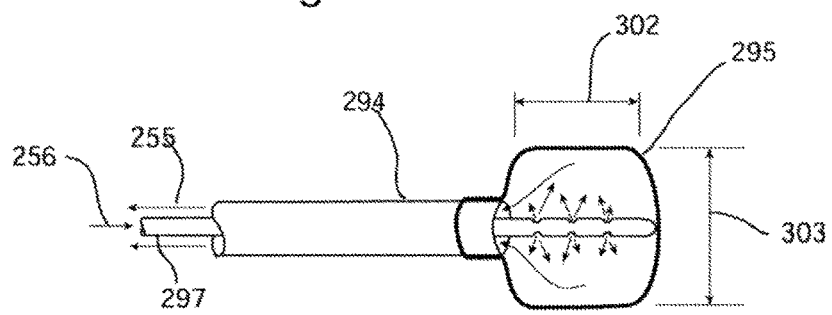
FIG. 18B is a schematic illustration of the distal end of the cryo-ablation balloon probe detailing the geometry of the cryo-ablation balloon.
Figure 18C:
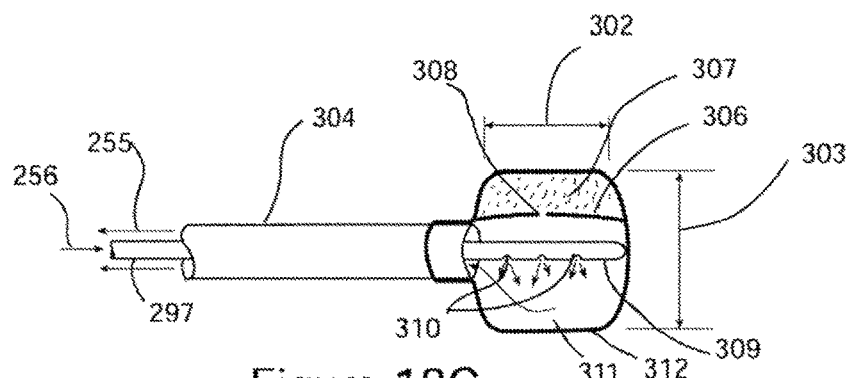
FIG. 18C is a schematic illustration of an alternate embodiment of the cryo-ablation balloon probe comprising an insulating chamber within the cryo balloon structure.
Figure 18D:
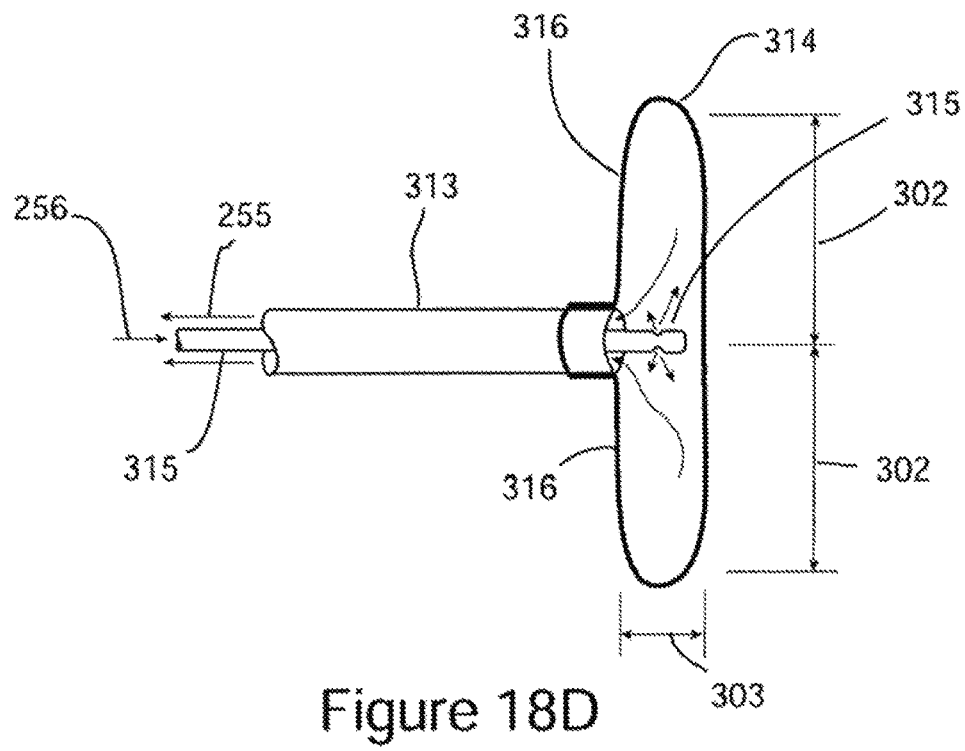
FIG. 18D is a schematic illustration of the distal end of an alternative embodiment of the cryo-ablation balloon probe comprising a tee shaped cryo-ablation balloon.
Figure 18E:
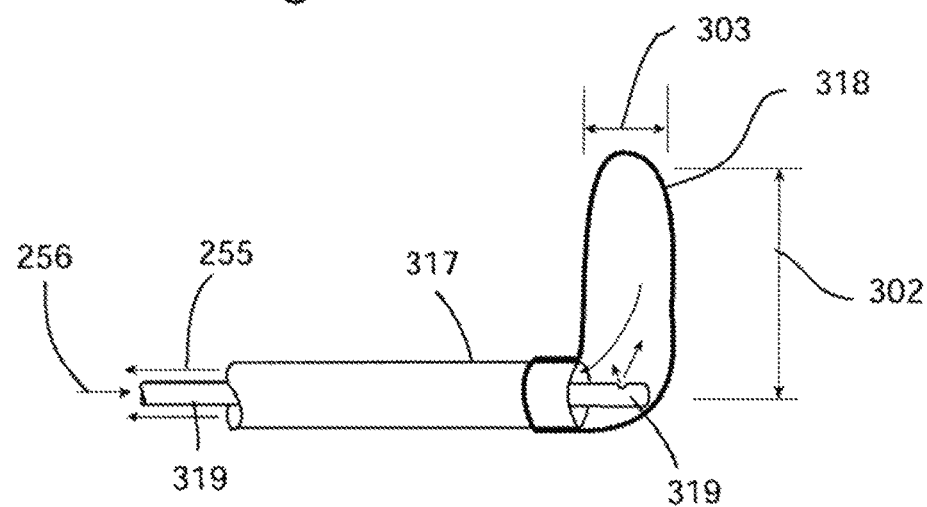
FIG. 18E is a schematic illustration of the distal end of an alternative embodiment of the cryo-ablation balloon probe comprising a "J" shaped cryo-ablation balloon.

FIG. 18A is a schematic illustration of cryo-ablation balloon probe 294 configured for cryo-ablation of parasympathetic nervous function of a nasal turbinate(s). Cryo-ablation balloon probe 294 comprises balloon 295, probe shaft 296, cryogen delivery tube 297, with lateral fenestrations 298 disposed on the distal end of cryogen delivery tube 297 within balloon 295 as shown. Cryo-ablation balloon probe 294 further comprises proximal hub 299 with cryogen exhaust port 299, cryogen supply port 301. Probe shaft 296 may be rigid or flexible. Balloon 295 functions as a cryogen expansion chamber for either a cryogenic evaporation cooling process or a Joules-Thompson effect cooling process. Pressurized cryogen 256 is delivered to the interior of balloon 295 through cryogen delivery tube 297 wider pressure. Cryogen 256 exits cryogen delivery tube 297 through lateral fenestrations 298 as shown, in the radial direction towards the wall of balloon 295. The radial wall of balloon 295 is the cryo-ablation surface. Expanded cryogen 255 exits balloon 295 through probe shaft 296, and is vented to atmosphere through exhaust port 300. Exhaust port 300 may comprise a pressure relief valve, which creates a back pressure to inflate balloon 295 at a predetermined pressure. Cryogen supply port 301 is configured to connect cryogen supply tube 297 to a source of cryogen. Proximal hub 299 may be configured as a handle, and comprise a cryogen control valve. FIG. 18B is a schematic illustration of the distal end of the cryo-ablation balloon probe detailing the geometry of the cryo-ablation balloon. The length 302 of balloon 295 is between approximately 3 mm and 20 mm, and the diameter 303 of balloon 295 is between 1 mm and 5 mm. FIG. 18C is a schematic illustration of an alternate embodiment 304 of the cryo-ablation balloon probe 294 comprising an insulating chamber 307 within the cryo balloon 305 structure. Insulating chamber 307 is formed by membrane 306 as shown. Fenestration 308 is a small opening in communication between expansion chamber 311 and insulating chamber 307, which allows insulation chamber to inflate with expanded cryogen gas 255 in a substantially static manner providing thermal insulation to the surface of balloon 305 adjacent to insulation chamber 307. Lateral fenestrations 310 direct pressurized cryogen 301 towards the wall of balloon 305 opposite of insulation chamber 307 forming cryo-ablation surface 312. The length 302 of balloon 305 is between approximately 3 mm and 20 mm, and the diameter of balloon 305 is between approximately 1 mm and 6 mm. FIG. 18D is a schematic illustration of the distal end of an alternative embodiment 313 of the cryo-ablation balloon probe 294 comprising a tee shaped cryo-ablation balloon 314. The length 302 of balloon 314 is between approximately 3 mm to 20 mm, and the diameter of balloon 303 is between approximately 1 mm and 6 mm. Cryogen delivery tube 315 is configured to direct pressurized cryogen down the horns 316 of balloon 314 as shown. FIG. 18E is a schematic illustration of the distal end of an alternative embodiment 317 of the cryo-ablation balloon probe 294 comprising a "J" shaped cryo-ablation balloon 318. The length 302 of balloon 318 is between approximately 3 mm and 20 mm, and the diameter 303 of balloon 318 is between approximately 1 mm and 6 mm. Cryogen delivery tube 319 is configured to direct pressurized cryogen 256 laterally into the "J" as shown.

Figure 19A:
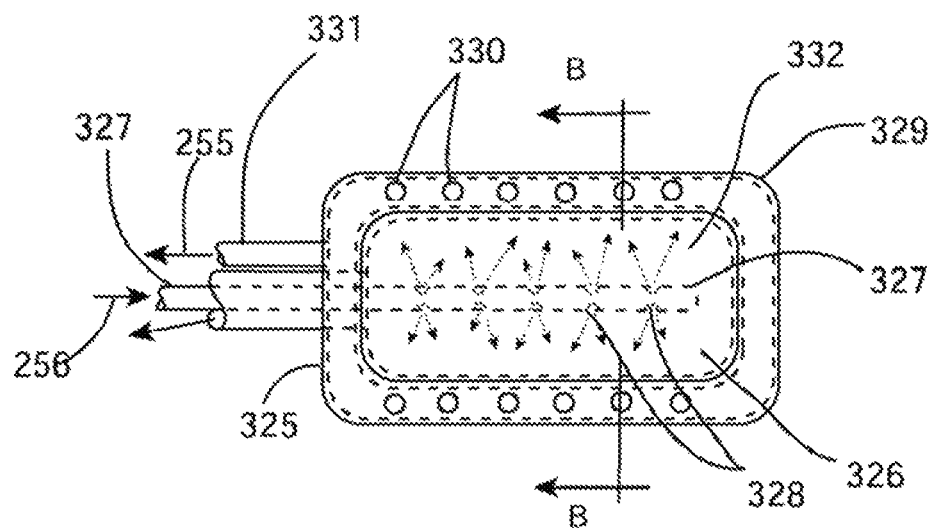
FIG. 19A is a schematic illustration of the distal end of an alternate embodiment a cryo-ablation probe comprising a cryo-ablation element with suction stabilization.
Figure 19B:
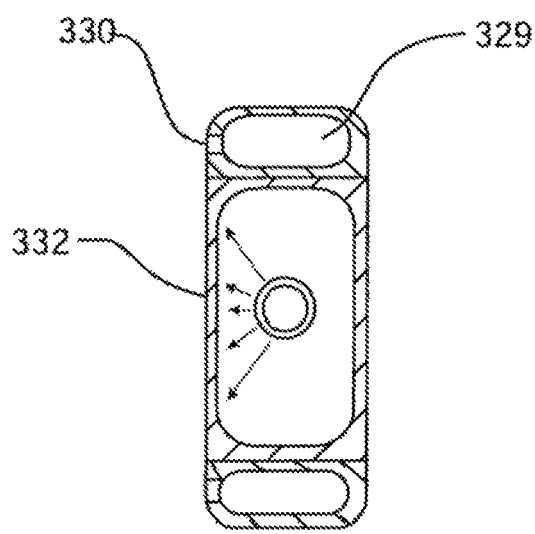
FIG. 19B is a cross sectional view of the distal end of the alternative embodiment showing the configuration of the cryo-ablation element and the suction stabilization means.

FIG. 19A is a schematic illustration of the distal end of an alternate embodiment 325 of cryo-ablation probe 294 comprising a cryo-ablation element 326 with suction stabilization. FIG. 19B is a cross sectional view of the distal end of the alternative embodiment 325 showing the configuration of the cryo-ablation element 326 and the suction stabilization means.

Ablation element 326 is surrounded by suction chamber 329 as shown. Suction chamber 329 is in fluidic communication with a suction source, not shown, by suction tube 331. Suction ports 330 are oriented in the same direction as cryo-ablation surface 332 and are configured to provide suction attachment to the tissue when cryo-ablation surface 332 is placed into contact with the nasal mucosa in the ablation target zone. Probe shaft 325, cryogen delivery tube 327, and lateral fenestrations 328 have similar function those previously described.

Figure 20A:
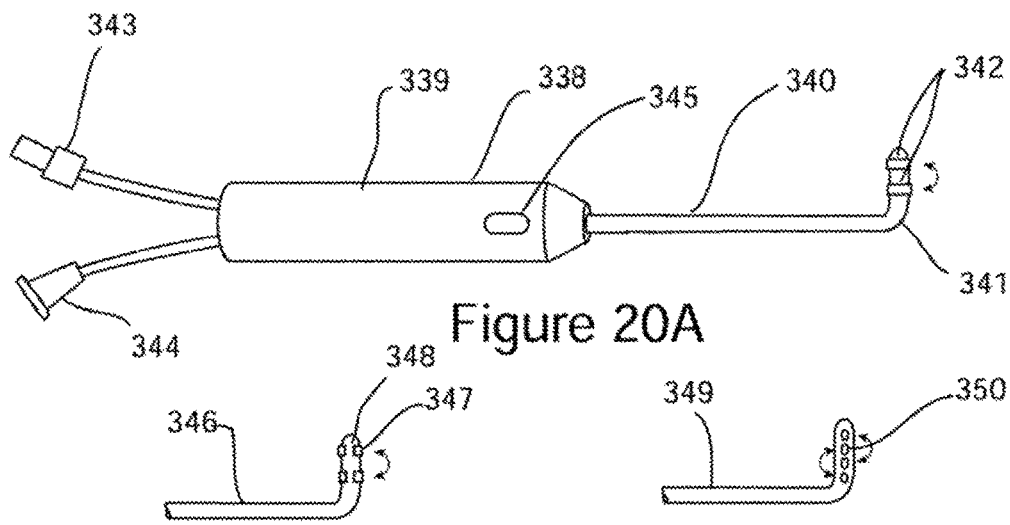
FIG. 20A is a schematic illustration of a radiofrequency (RF) ablation probe configured for ablation of the posterior nasal nerves with a bi-polar ring electrode ablation element on an "J" shaped distal probe shaft.
Figure 20B:
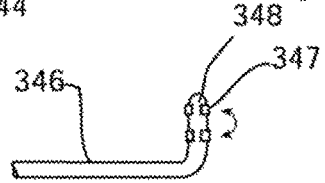
FIG. 20B is a schematic illustration of the distal end of an alternative embodiment of an RF ablation probe comprising a bi-polar ring electrode ablation element on an "J" shaped distal probe shaft.
Figure 20C:
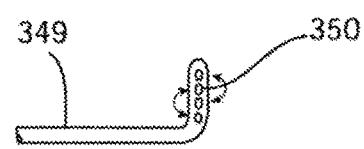
FIG. 20C is a schematic illustration of an alternative embodiment of the distal end of an RF ablation probe comprising a bi-polar electrode ablation element on an "J" shaped distal probe shaft with the electrodes disposed in a lateral array.
Figure 20D:
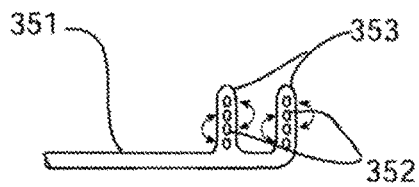
FIG. 20D is a schematic illustration of an alternative embodiment of the distal end of an RF ablation probe comprising a bi-polar electrode ablation element on a "U" shaped distal probe shaft with the electrodes disposed in a lateral array.
Figure 20E:
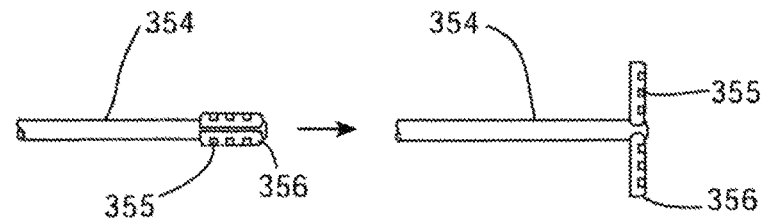
FIG. 20E is a schematic illustration of the distal end of an alternative embodiment of an RF ablation probe comprising a bi-polar electrode ablation element on a user deployable "T" shaped structure.

FIG. 20A is a schematic illustration of radiofrequency (RF) ablation probe 338 configured for ablation of the parasympathetic nervous function of a nasal turbinate(s) with a bi-polar ring electrode ablation element 342 on an "J" shaped distal probe tip 341. RF ablation probe 338 comprises handle 339, probe shaft 340, "J" shaped probe tip 341, bipolar ring electrode pair 342, RF activation switch 345, electrical connector 343, and fluid connector 344. Those skilled in the art of RF ablation probes are familiar with the many possible configurations and construction techniques for RF electrodes and probes that are within the scope of this invention, therefore detailed description of the illustrated, electrode configurations described below, and their construction techniques is not warranted. Electrical connector 343 is configured for connection to a radiofrequency energy generator, for which there are many commercially available. Fluid connector 344 is configured for connection to source of liquid irrigant. Fluid connector 344 may be in fluidic communication with at least one fluid irrigation port located the vicinity of the RF ablation electrode, and is embodiment specific. RF activation switch 345 allows the user to activate the RF ablation and terminate the RF ablation. Probe shaft 340 is between approximately 2 mm to 6 mm in diameter, and between approximately 4 cm and 10 cm long, but could be longer. The length of "J" tip 341 is between approximately 0.5 cm and 1.5 cm. Ring the spacing between RF electrode pair 342 is between approximately 2 mm and 6 mm. FIG. 20B is a schematic illustration of the distal end of an alternative embodiment 346 of RF ablation probe 338 comprising a bi-polar segmented ring electrode ablation element on an "J" shaped distal probe shaft. The gap 348 shown in the ring electrode is on the side opposite of the side configured for RF ablation. The gap 348 in the ring electrodes protect the nasal septum during RF ensuring that RF energy is only applied to the lateral nasal wall at the ablation target. FIG. 20C is a schematic illustration of alternative embodiment 349 of the distal end of RF ablation probe 338 comprising a bi-polar electrode ablation element 350 on a "J" shaped distal probe shaft with the electrodes disposed in a lateral array. FIG. 20D is a schematic illustration of alternative embodiment 351 of the distal end of RF ablation probe 338 comprising a bi-polar electrode ablation element 352 on a "U" shaped distal probe shaft 353 with the electrodes disposed in a lateral array. FIG. 20E is a schematic illustration of the distal end of alternative embodiment 354 of RF ablation probe 338 comprising a bi-polar electrode ablation element 355 on a user deployable "T" shaped structure 356. Element 356 is comprised of two halves which can alternately be collapsed and deployed as in FIG. 20E. The two halves of the electrode structure 356 are pivoted to allow them to move laterally relative to the catheter shaft 354. Electrodes 355 can operate in a mono polar, bipolar or multipolar fashion as known in the art.

Figure 21A:
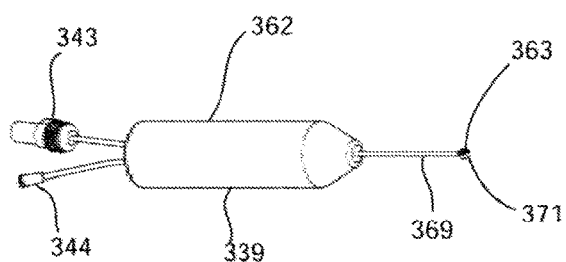
FIG. 21A is a schematic illustration of an RF ablation probe configured for ablation of posterior nasal nerves comprising an array of RF ablation electrodes disposed on a planar surface and a fluid irrigation means associated with the electrodes.
Figure 21B:
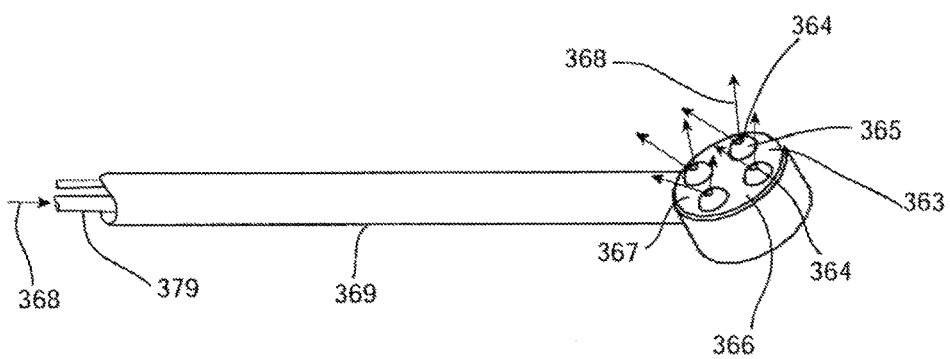
FIG. 21B is a schematic illustration of the distal end of the RF ablation probe showing the arrangement of the ablation electrodes and the associated fluid irrigation means.

FIG. 21A is a schematic illustration of alternative embodiment 362 to RF ablation probe 338 configured for ablation of the parasympathetic nervous function of a nasal turbinate(s) comprising an array of RF ablation electrodes 363 disposed on a planar surface with a fluid irrigation means associated with the electrodes. FIG. 21B is a schematic illustration of the distal end of the RF ablation probe 362 showing the arrangement of the ablation electrode array 363 and the associated fluid irrigation means. Alternative embodiment 362 comprises distal probe tip 119, probe shaft 369, handle 339, fluid connector 344, and electrical connector 343. Electrode array 363 comprises two or more dome shaped electrodes 365, that are electrically configured into a bipolar pair, meaning that if there are 4 electrodes 365, then two of the electrodes are connectable to one pole of an RF generator, and the second two electrodes are connectable to the opposite pole of the RF generator, etc. Electrodes 365 are dome shaped and protrude from planar surface 366. A fluid port 364 is associated with each electrode 365. All fluid ports are in fluidic communication with fluid connector 344. Fluid ports 364 are configured to irrigate the surface of the nasal mucosa that is contact with electrodes 365 to provide cooling of the mucosa and the electrodes 365, to minimize thermal injury to the surface of the mucosa, and to prevent sticking of the electrodes to the surface of the mucosa. Probe tip 371 is between approximately 4 mm and 8 mm in diameter, and between approximately 3 mm to 8 mm thick. The number of electrodes 365 of electrode array 363 may be between 2 and approximately 10.

Figure 22A:
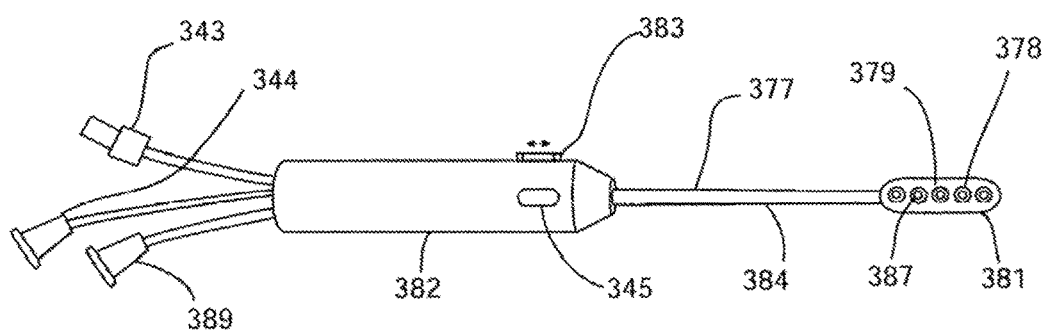
FIG. 22A is a schematic illustration of an alternative RF ablation probe comprising, an electrode array disposed on a planar surface; a fluid irrigation means associated electrodes, and a deployable needle configured for injecting a liquid into a sub-mucosal space.
Figure 22B:
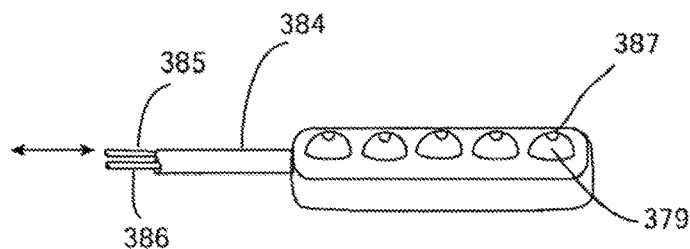
FIG. 22B is a schematic illustration of the distal end of the alternative embodiment RF ablation probe showing the arrangement of the ablation electrodes and the associated fluid irrigation means.
Figure 22C:
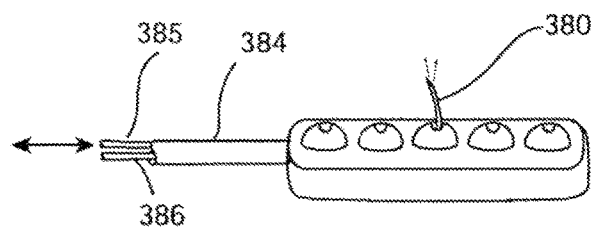
FIG. 22C is a schematic illustration of the distal end of the alternative embodiment RF ablation probe showing the arrangement of the ablation electrodes and the associated fluid irrigation means with the needle deployed.

FIG. 22A is a schematic illustration of an alternative embodiment 377 of RF ablation probe 362 comprising a linear electrode array 378 disposed on a planar surface; a fluid irrigation ports 387 associated electrodes 379, and a deployable needle 380 configured for injecting a liquid into a sub-mucosal space. FIG. 22B is a schematic illustration of the distal end of the alternative embodiment 377 RF ablation probe showing the arrangement of the ablation electrodes 379 and the associated fluid irrigation ports 387. FIG. 22C is a schematic illustration of the distal end of the alternative embodiment 377 RF ablation probe showing the arrangement of the ablation electrodes 379 and the associated fluid irrigation ports 387 with the needle 380 deployed. The function, of domed electrodes 379, fluid ports 387, electrical connector 343, fluid connector 344, RF activation switch 345, handle 382, and shaft 384 all function in essentially the same manner as described for prior embodiment 362. This embodiment has a linear electrode array 378, and a deployable needle configured for injecting a liquid into the sub-mucosal space where the liquid may comprise an anesthetic. Needle actuator 383 provides the user a means actuating needle 380. Fluid connector 389 is in fluidic communication with needle 380, through needle shaft 385, and is configured with a female luer connector for mating with a syringe, not shown. Shaft 384 contains needle shaft 385, electrical cable 386, and provides a conduit for irrigation fluid, not shown.

Figure 23A:
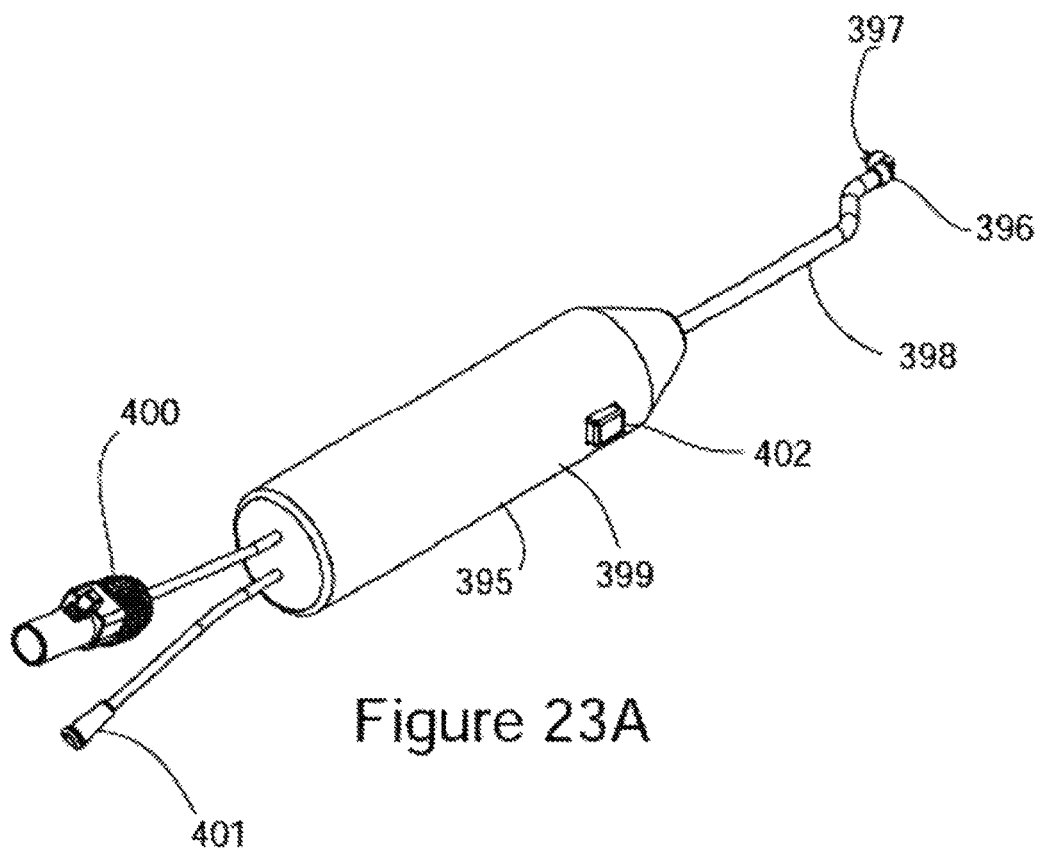
FIG. 23A is a schematic illustration of an RF interstitial needle ablation probe configured for interstitial ablation of the parasympathetic nervous function of a nasal turbinate(s).
Figure 23B:
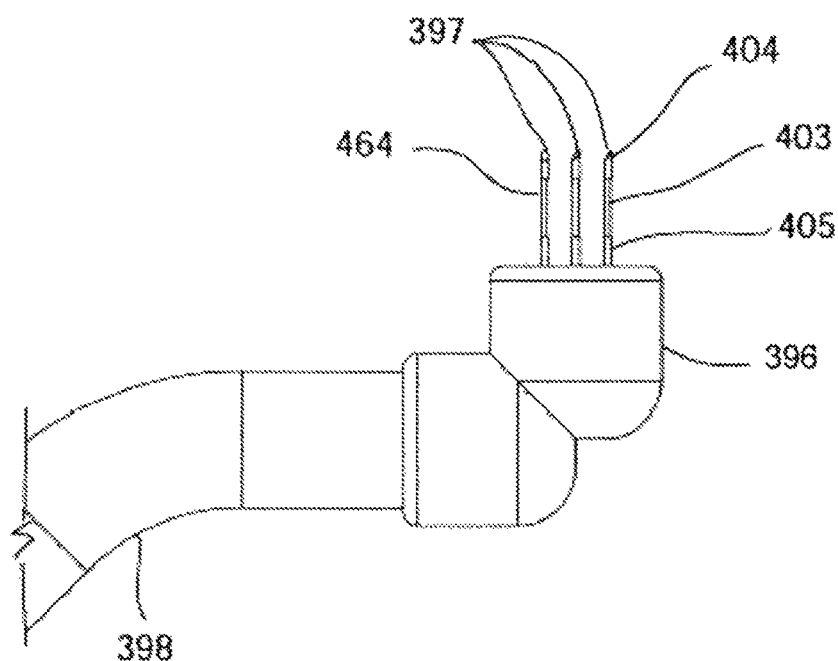
FIG. 23B is a schematic illustration of the distal end of the RF interstitial needle ablation probe.

FIG. 23A is a schematic illustration of an RF interstitial needle ablation probe 395 configured for interstitial ablation of a posterior nasal nerve. FIG. 23B is a schematic illustration of the distal end 396 of the RF interstitial needle ablation probe 395. RF interstitial needle probe 395 comprises distal tip 396, probe shaft 398, handle 399, electrical connector 400, fluid connector 401, RF activation switch 402. Distal tip 396 comprises interstitial needle electrode array 397, which comprises more than one interstitial needle 464 Handle, 399, RF activation switch 402, electrical connector 400, and probe shaft 398 function in a manner previously described. Fluid port 401 is in fluidic communication with at least one RF ablation needle 464, with the at least one RF ablation needle 464 being hollow and configured for injecting a liquid into the nasal sub-mucosal space. Each RF ablation needle 464 has a proximal electrically insulating coating 405, and a distal electrically insulating coating 404, forming RF electrode surface 403. Proximal insulator 405, and distal insulator 404 are configured for limiting the ablation effects to the sub-mucosal space, which will be described in further detail below. Interstitial needle electrode array 397 may be configured as a mono-polar electrode array, or a bipolar electrode array. Interstitial needle electrode array 397 may be configured as a linear array, a circular array, a triangular array, or any other geometric form. Interstitial needle electrode array 397 may comprise two or more RF ablation needles 464. RF ablation needles 464 are between approximately 18 and 28 gauge, and between approximately 3 mm and 10 mm long.

Figure 24A:
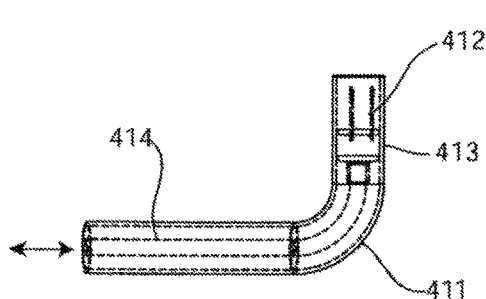
FIG. 24A is a cross sectional view of the distal end of an RF interstitial needle ablation comprising a deployable and retractable array of RF ablation needles configured for lateral deployment showing the needle array retracted.
Figure 24B:
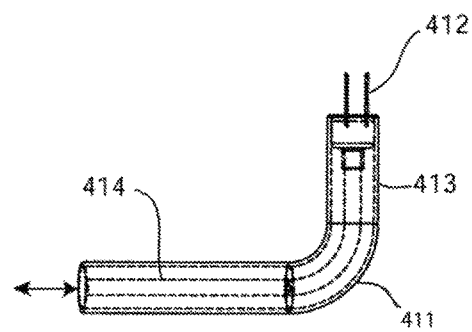
FIG. 24B is a cross sectional view of the distal end of an RF interstitial needle ablation comprising, a deployable and retractable array of RF ablation needles configured for lateral deployment showing the needle array deployed.
Figure 24C:
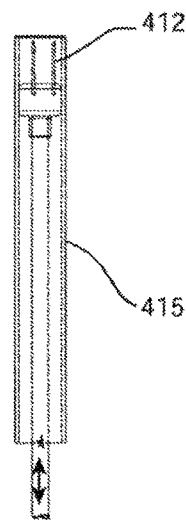
FIG. 24C is a cross sectional view of the distal end of an RF interstitial needle ablation comprising a deployable and retractable array of RF ablation needles configured for axial deployment showing the needle array retracted.
Figure 24D:
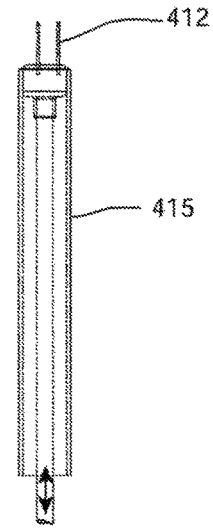
FIG. 24D is a cross sectional view of the distal end of an RI interstitial needle ablation comprising a deployable and retractable array of RF ablation needles configured for axial deployment showing the needle array deployed.

FIG. 24A is a cross sectional view of the distal end of an alternative embodiment 411 to RF interstitial needle ablation probe 395 comprising a deployable and retractable array of RF ablation needles 412 configured for lateral deployment showing the needle array retracted. FIG. 24B is a cross sectional view of the distal end of an alternative embodiment 411 of RF interstitial needle ablation probe 395 comprising a deployable and retractable array of RF ablation needles configured for lateral deployment, showing the needle array deployed interstitial needle array 412 is housed in a hollow sheath with a "J" tip 413 as shown. Linear actuator shaft 414 is in mechanical communication with a user actuator lever at the proximal end not shown. Linear actuator shaft 414 is moved in the distal direction to deploy needle array 412, and moved in the proximal direction to retract needle array 412 as shown. FIG. 24C is a cross sectional view of the distal end of an alternative embodiment 415 of RF interstitial needle ablation probe 395 comprising a deployable and retractable array of RF ablation needles configured for axial deployment showing the needle array retracted. FIG. 24D is a cross sectional view of the distal end of an alternative embodiment 415 of RF interstitial needle ablation probe 395 comprising a deployable and retractable array of RF ablation needles configured for axial deployment showing the needle array deployed.

Figure 25A:
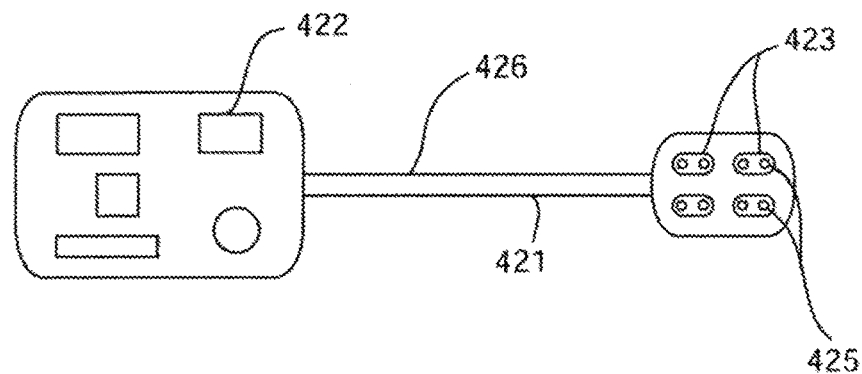
FIG. 25A is a schematic illustration of an integrated flexible circuit configured for use with an RF ablation probe comprising an RF energy source and control circuits at one end, and an RF ablation electrode array at the opposite end.
Figure 25B:
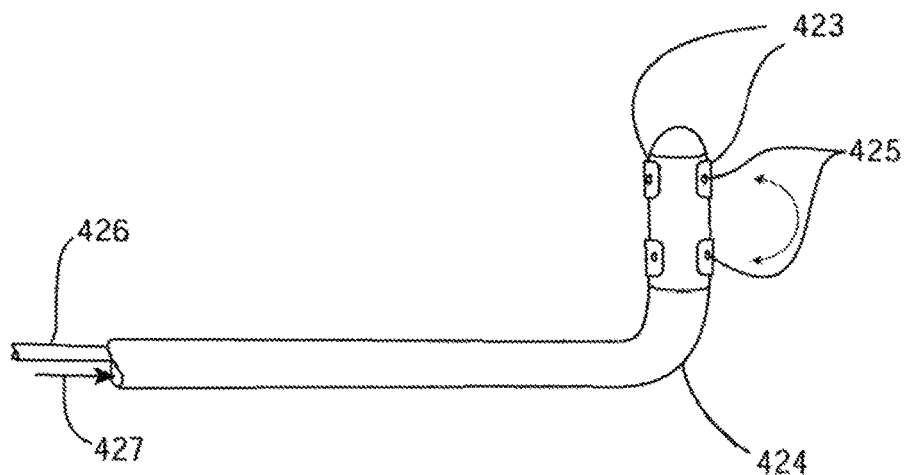
FIG. 25B is a schematic illustration of the RF ablation electrode array of the flexible circuit mounted on the distal shaft of an RF ablation probe that is configured for ablation of posterior nasal nerves.

FIG. 25A is a schematic illustration of an integrated flexible circuit 421 configured for use with an RF ablation probe comprising an RF energy source and control circuits 422 at one end, and an RF ablation electrode array 423 at the opposite end, connected by electrical conduits 426. FIG. 25B is a schematic illustration of the RF ablation electrode array 423 of the flexible circuit mounted on the distal shaft of an RF ablation probe that is configured for ablation of the parasympathetic nervous function of a nasal turbinate. Also shown are optional fluid ports associated with the RF ablation electrode array as shown, with irrigation fluid 427 supplied to irrigation ports 425 through distal shaft 424.

Figure 26A:
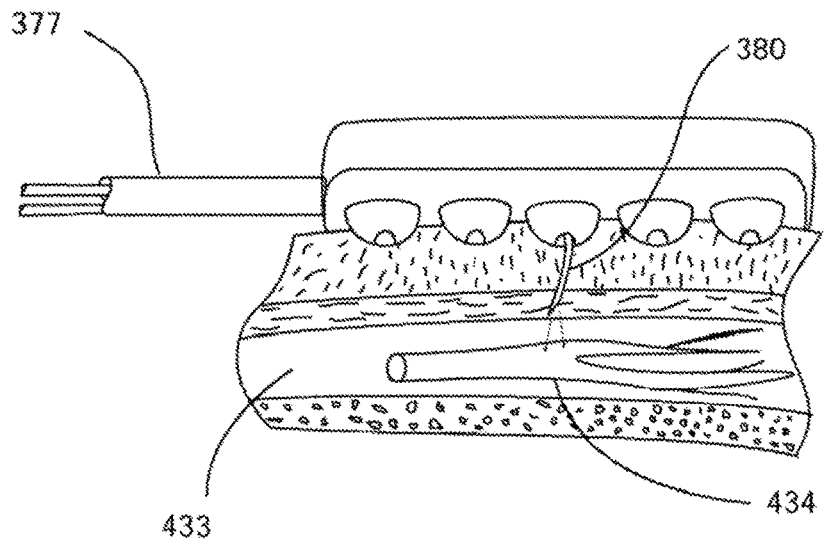
FIG. 26A is an in situ schematic illustration of the RF ablation probe depicted in FIGS. 22A through 22C showing the needle injecting an anesthetic into the sub-mucosal space prior to an RF ablation of posterior nasal nerves.
Figure 26B:
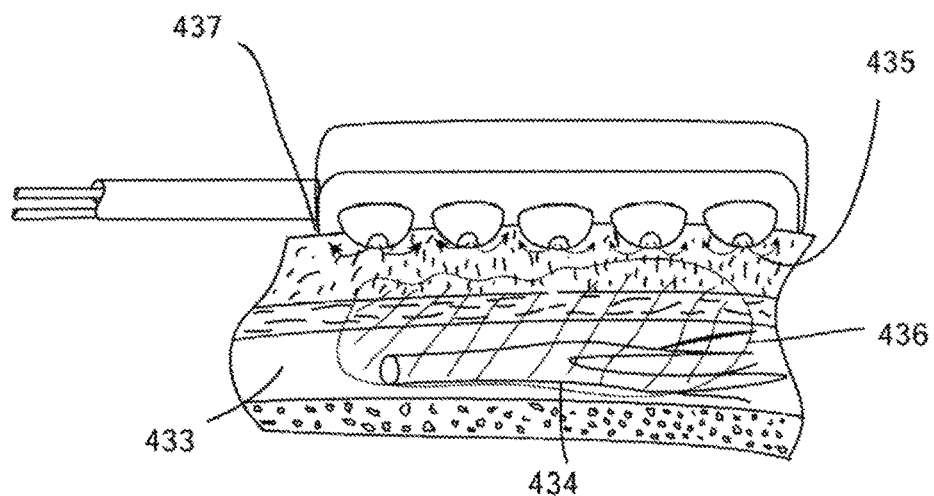
FIG. 26B is an in situ schematic illustration of the resulting ablation.

FIG. 26A is an in situ schematic illustration of the RF ablation probe 377 depicted in FIGS. 10 through 10C showing needle 380 injecting an anesthetic into the submucosal space 433 prior to an RF ablation of the posterior nasal nerve 434. FIG. 26B is an in situ schematic illustration of the resulting RF ablation 436 showing the ablation zone 436 encompassing posterior nasal nerve 434, and residing below the mucosal surface 437 due to the cooling effect of liquid irrigant 435.

Figure 27:
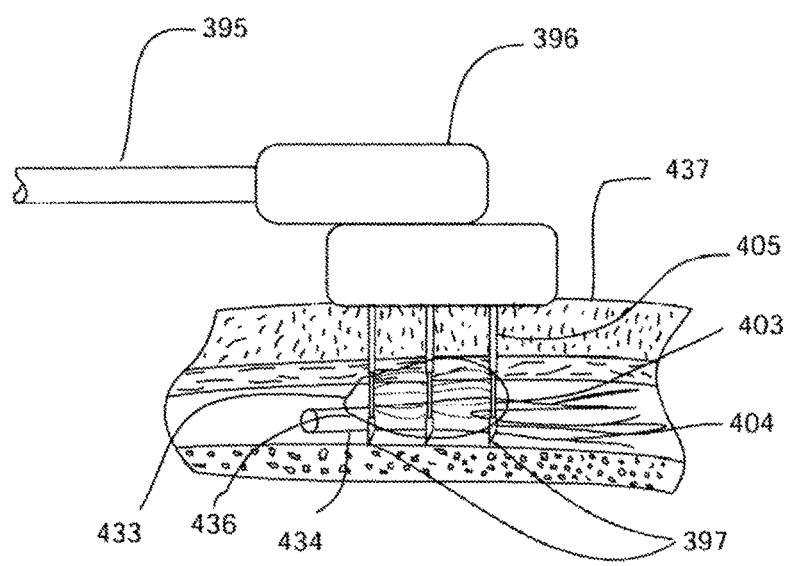
FIG. 27 is an in situ schematic illustration of an ablation of posterior nasal nerves using the RF interstitial needle ablation probe depicted in FIGS. 23A and 23B.

FIG. 27 is an in situ schematic illustration of an RF ablation of the parasympathetic nerve of a posterior nasal nerve 434 using the RF interstitial needle ablation probe 395 depicted in FIGS. 11A and 11B showing ablation zone 436 encompassing posterior nasal nerve 434 and residing below the mucosa surface 437 due to the arrangement of needle electrode surface(s) 403 and needle insulation zones 404 & 405.

Figure 14D:
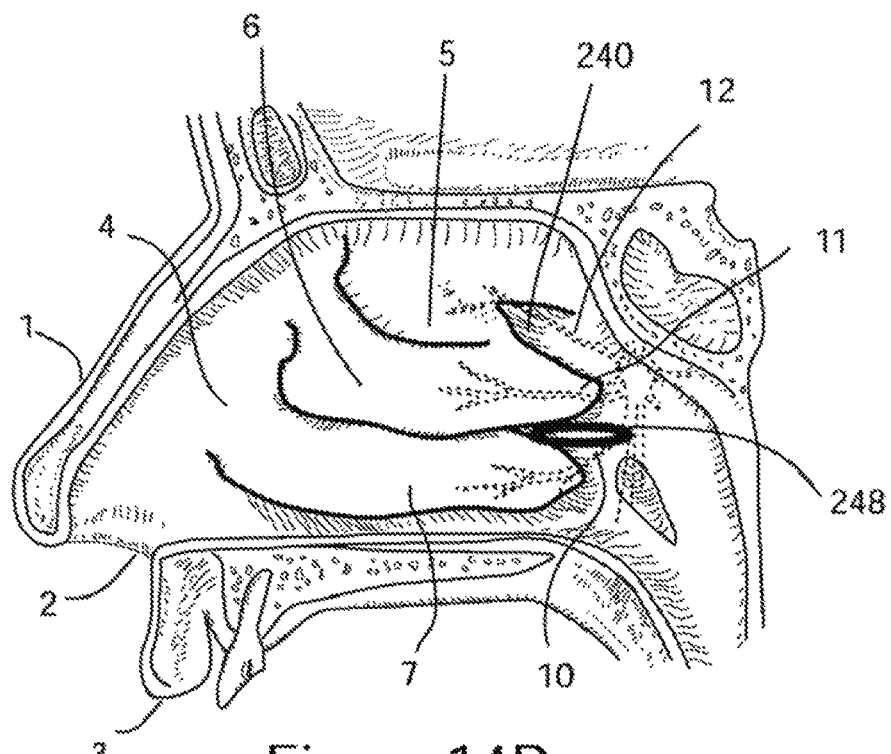
FIG. 14D is an internal lateral view of the nasal cavity showing an anatomical target for ablation of posterior nasal nerves.
Figure 28:
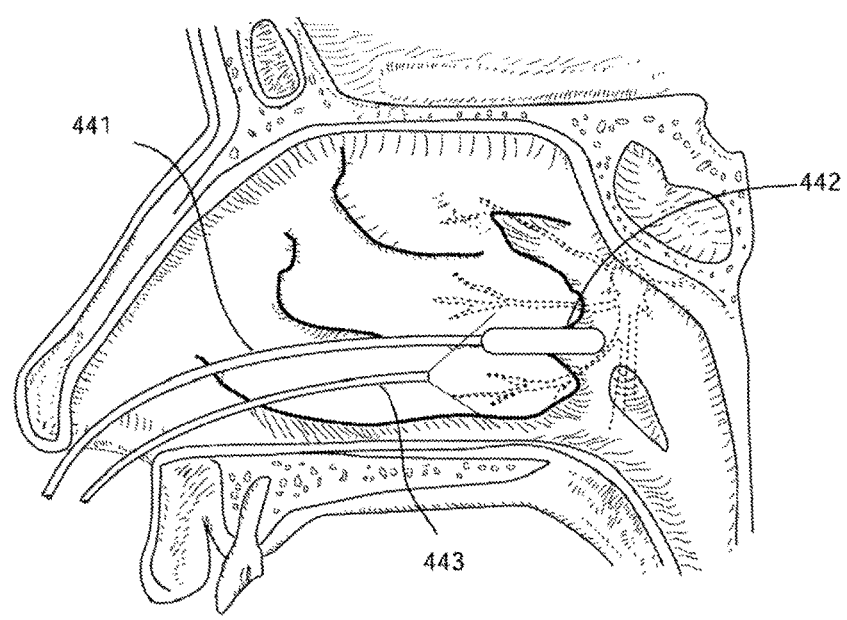
FIG. 28 is an in situ illustration of the ablation of the posterior nasal nerves at the ablation target depicted in FIG. 14D.

FIG. 28 is an in situ illustration of the ablation of the posterior nasal nerve depicted in FIG. 14D. Generic ablation device 441 is shown with cylindrical ablation element 442, which could be a cryo ablation element, an RF ablation element, or some other type of thermal ablation element. Also shown is endoscope 443, which provides the surgeon an image for positioning ablation element 442 at the target location, and a means for monitoring the ablation.

Figure 29:
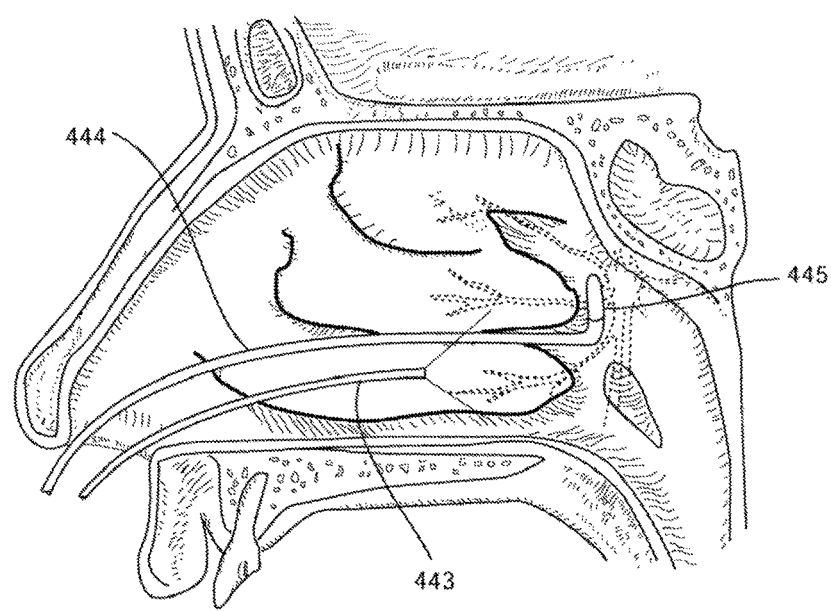
FIG. 29 is an in situ illustration of the ablation of the posterior nasal nerves at the ablation target depicted in FIG. 24A.

FIG. 29 is an in situ illustration of the ablation of the posterior nasal nerve of a nasal turbinate at the ablation target depicted in FIG. 14B. Generic ablation device 441 is shown with cylindrical ablation element 442, which could be a cryo ablation element, an RF ablation element, or some other type of thermal ablation element. Also shown is endoscope 443, which provides the surgeon an image for positioning ablation element 442 at the target location, and a means for monitoring the ablation.

Figure 30:
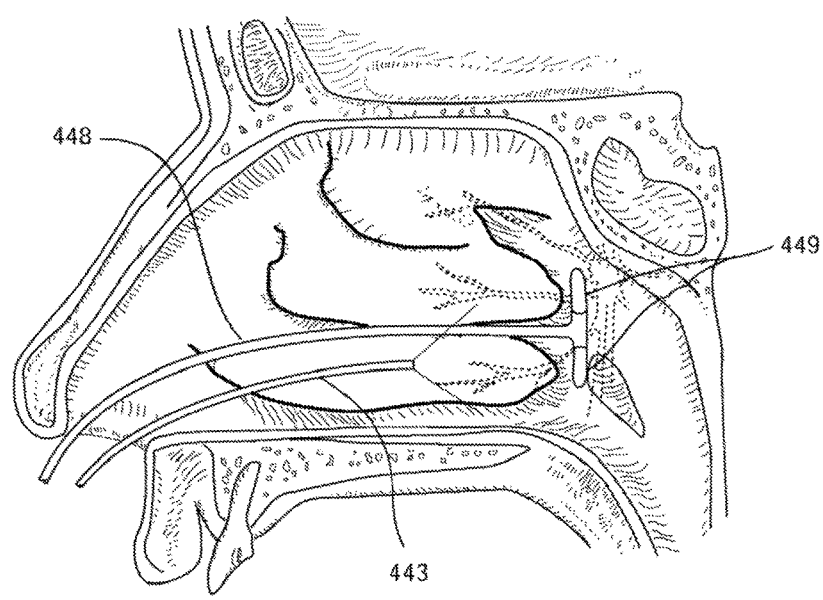
FIG. 30 is an in situ illustration of the ablation of the posterior nasal nerves at the ablation target area depicted in FIG. 14B.

FIG. 30 is an in situ illustration of the ablation of the posterior nasal nerve using a generic "T" tipped ablation device 448. Generic "T" tipped ablation device 448 is shown with ablation elements 449, which could be cryo ablation elements, RF ablation elements, or some other type of thermal ablation elements. Also shown is endoscope 443, which provides the surgeon an image for positioning ablation element 442 at the target location, and a means for monitoring the ablation.

Figure 31A:
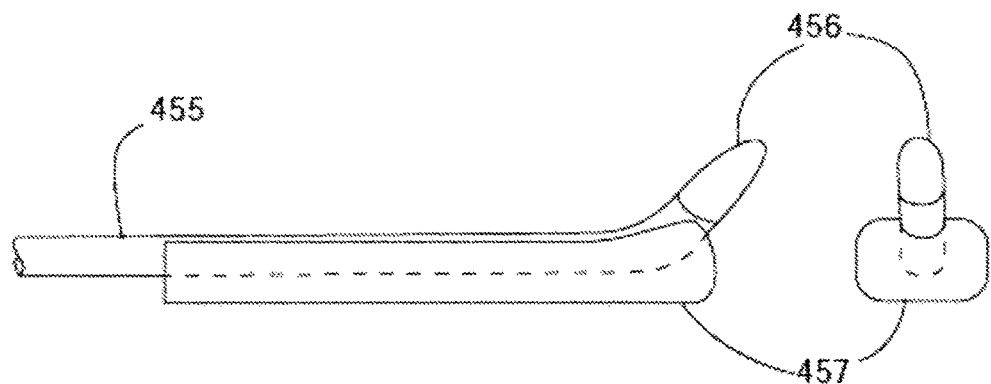
FIG. 31A is a schematic illustration of the ablation probe and an insulated probe guide configured to protect the nasal septum from thermal injury during an ablation of the posterior nasal nerves.
Figure 31B:
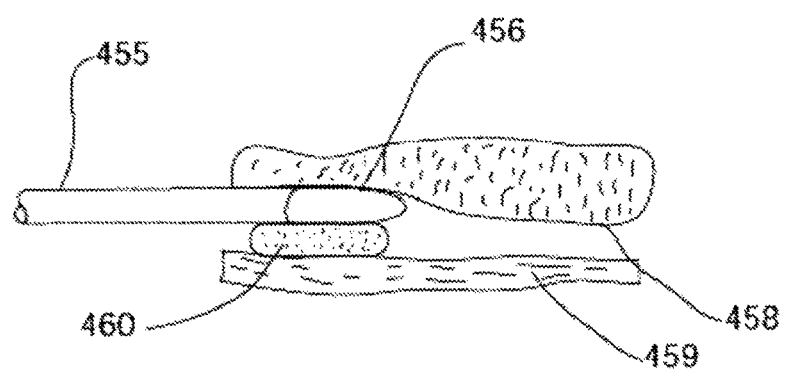
FIG. 31B is an in situ illustration of an ablation probe configured for ablation of the posterior nasal nerves which comprises an insulating structure configured to protect the nasal septum.
Figure 31C:
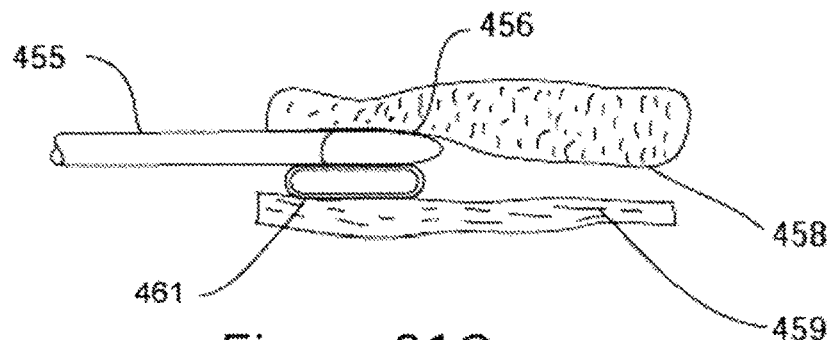
FIG. 31C is an in situ illustration of an ablation probe configured for ablation of the parasympathetic nervous function of posterior nasal nerves which comprises a space creating structure configured to protect the nasal septum.

FIG. 31A is a schematic illustration of generic ablation probe 455 and an insulated probe guide 457 configured to protect the nasal septum from thermal injury during an ablation of the parasympathetic nervous function of a nasal turbinate(s). Probe guide 457 is configured to press ablation element 456 of probe 455 against the lateral all of a nasal cavity 458 and create a thermally insulative space between the lateral wall of the nasal cavity 458 and the nasal septum 459 as shown in FIGS. 31B and 31C. Probe guide 457 may be fabricated from foam material, or any other suitable thermally insulative material. FIG. 31B is an in situ illustration of generic ablation probe 437 configured for ablation of the posterior nasal nerve which comprises an insulating structure 460 configured to protect the nasal septum 459 from thermal injury. Structure 460 may comprise an inflatable balloon. FIG. 31C is an in situ illustration of generic ablation probe 455 configured for ablation of the parasympathetic nervous function of a nasal turbinate(s) which comprises a space creating structure 461 configured to protect the nasal septum 459 from thermal injury. Structure 461 may comprise a deployable wire structure or surgical basket structure.

What is claimed is:

1. A method for treating nerve tissue within a nasal cavity of a patient, the method comprising:
    advancing a treatment delivery portion of an energy-based treatment device into a nostril of the patient;
    contacting a mucosal surface of the nasal cavity with the treatment delivery portion; and
    delivering an energy-based treatment from the treatment delivery portion to treat the nerve tissue underlying the mucosal surface, wherein the delivering of the energy-based treatment comprises delivering energy in a form selected from the group consisting of ultrasound, radiofrequency, and electrical energy.

2. The method of claim 1, wherein the delivering of the energy-based treatment to treat the nerve tissue underlying the mucosal surface comprises ablating the nerve tissue.

3. The method of claim 1, wherein the delivering of the energy-based treatment comprises delivering radiofrequency energy from a first electrode on a tissue contact surface to a second electrode on the tissue contact surface.

4. The method of claim 3, wherein the first electrode and second electrode comprise dome shaped electrodes on the tissue contact surface, and wherein contacting the mucosal surface comprises contacting the dome shaped electrodes on the tissue contact surface with the mucosal surface.

5. The method of claim 1, further comprising measuring energy-based treatment delivery using a thermocouple disposed in a vicinity of the treatment delivery portion.

6. The method of claim 1, wherein the delivering of the energy-based treatment to treat the nerve tissue underlying the mucosal surface comprises ablating the nerve tissue such that at least one symptom of rhinitis is reduced.

7. The method of claim 1, wherein the nerve tissue comprises a posterior nasal nerve, a branch of a vidian nerve, a parasympathetic nerve, a greater palatine nerve, a maxillary nerve, a sphenopalatine ganglion nerve, or a posterolateral nerve.

8. The method of claim 1, wherein the delivering of the energy-based treatment comprises delivering bipolar radiofrequency energy.

9. The method of claim 1, wherein the treatment delivery portion comprises a plurality of electrodes and the delivering of the energy-based treatment comprises delivering radiofrequency energy.

10. The method of claim 9, wherein the plurality of electrodes comprise eight electrodes arranged in two lateral arrays.

11. The method of claim 1, further comprising adjusting a shape of the treatment delivery portion of the energy-based treatment device to increase contact with the mucosal surface or pressure against the mucosal surface.

12. The method of claim 11, wherein the treatment delivery portion comprises an expandable structure having bipolar electrode elements and adjusting the shape of the treatment delivery portion comprises expanding the bipolar electrode elements away from a longitudinal axis of the energy-based treatment device.

13. A method for treating nerve tissue within a nasal cavity of a patient, the method comprising: advancing a treatment delivery portion of an energy-based treatment device into a nostril of the patient; contacting a mucosal surface of the nasal cavity with the treatment delivery portion; delivering an energy-based treatment from the treatment delivery portion to treat the nerve tissue underlying the mucosal surface wherein the delivering of the energy-based treatment to treat the nerve tissue underlying the mucosal surface comprises ablating the nerve tissue such that rhinorrhea is reduced; and wherein the delivering of the energy-based treatment comprises delivering bipolar radiofrequency energy.

14. The method of claim 13, further comprising adjusting a shape of the treatment delivery portion of the energy-based treatment device.

15. The method of claim 14, wherein the treatment delivery portion comprises an expandable structure and adjusting the shape of the treatment delivery portion comprises inflating the expandable structure from a deflated configuration into an expanded configuration against the mucosal surface.

16. A method for treating nerve tissue within a nasal cavity of a patient, the method comprising:
advancing a treatment delivery portion of an energy-based treatment device into a nostril of the patient, wherein the advancing the treatment delivery portion of the energy-based treatment device into the nostril of the patient comprises positioning the treatment delivery portion relative to a tissue region surrounded by a middle nasal turbinate, an inferior nasal turbinate, and a lateral nasal wall;
contacting a mucosal surface of the nasal cavity with the treatment delivery portion;
adjusting a shape of the treatment delivery portion of the energy-based treatment device; and
delivering an energy-based treatment from the treatment delivery portion to treat the nerve tissue underlying the mucosal surface.

17. The method of claim 16, wherein the delivering of the energy-based treatment to treat the nerve tissue underlying the mucosal surface comprises ablating the nerve tissue.

18. The method of claim 16, wherein the delivering of the energy-based treatment comprises delivering energy in a form selected from the group consisting of ultrasound, radiofrequency, electrical, and thermal energy.

19. The method of claim 16, wherein the delivering of the energy-based treatment comprises applying cryotherapy.

20. The method of claim 19, wherein the applying the cryotherapy comprises ablating the nerve tissue.

21. The method of claim 16, wherein the delivering of the energy-based treatment to treat the nerve tissue underlying the mucosal surface comprises ablating the nerve tissue such that at least one symptom of rhinitis is reduced.

22. The method of claim 16, further comprising measuring energy-based treatment delivery using a thermocouple disposed in a vicinity of the treatment delivery portion.

23. The method of claim 16, wherein the delivering of the energy-based treatment comprises delivering bipolar radiofrequency energy.

24. The method of claim 16, wherein the treatment delivery portion comprises an expandable structure and adjusting the shape of the treatment delivery portion comprises inflating the expandable structure from a deflated configuration into an expanded configuration against the mucosal surface.

25. A method for treating nerve tissue within a nasal cavity of a patient, the method comprising:
advancing a treatment delivery portion of an energy-based treatment device into a nostril of the patient;
contacting a mucosal surface of the nasal cavity with the treatment delivery portion;
adjusting a shape of the treatment delivery portion of the energy-based treatment device, wherein the treatment delivery portion comprises an expandable structure and adjusting the shape of the treatment delivery portion comprises inflating the expandable structure from a deflated configuration into an expanded configuration against the mucosal surface; and
delivering an energy-based treatment from the treatment delivery portion to treat the nerve tissue underlying the mucosal surface.

26. The method of claim 25, wherein the inflating comprises introducing a cryogenic fluid into the expandable structure, wherein evaporation of the cryogenic fluid inflates the expandable structure into the expanded configuration.

27. The method of claim 25, wherein the contacting the mucosal surface comprises positioning a member extending within the expandable structure into contact against the mucosal surface through the expandable structure.

* * * * *